United States Patent
Walensky et al.

(10) Patent No.: US 8,921,323 B2
(45) Date of Patent: Dec. 30, 2014

(54) METHODS AND COMPOSITIONS FOR MODULATING BCL-2 FAMILY POLYPEPTIDES

(75) Inventors: Loren D. Walensky, Chestnut Hill, MA (US); Nico Tjandra, Rockville, MD (US); Evripidis Gavathiotis, Boston, MA (US); Motoshi Suzuki, Rockville, MD (US); Gregory Bird, Pelham, NH (US)

(73) Assignees: Dana Farber Cancer Institute, Inc., Boston, MA (US); The United States of America, as Represented by the Secretary, Department of Health and Human Services, Washington, DC (US)

(*) Notice: Subject to any disclaimer, the term of this patent is extended or adjusted under 35 U.S.C. 154(b) by 489 days.

(21) Appl. No.: 12/680,098

(22) PCT Filed: Sep. 26, 2008

(86) PCT No.: PCT/US2008/011500
§ 371 (c)(1),
(2), (4) Date: Jul. 6, 2010

(87) PCT Pub. No.: WO2009/042237
PCT Pub. Date: Apr. 2, 2009

(65) Prior Publication Data
US 2010/0286057 A1 Nov. 11, 2010

Related U.S. Application Data

(60) Provisional application No. 61/124,221, filed on Apr. 14, 2008, provisional application No. 60/995,545, filed on Sep. 26, 2007.

(51) Int. Cl.
*A61K 38/00* (2006.01)
*C07K 14/00* (2006.01)
*G01N 33/50* (2006.01)
*C07K 14/47* (2006.01)

(52) U.S. Cl.
CPC ........ *G01N 33/5079* (2013.01); *G01N 2510/00* (2013.01); *G01N 33/5011* (2013.01); *C07K 14/4747* (2013.01); *G01N 33/5035* (2013.01)
USPC ........ 514/19.3; 514/18.9; 514/21.4; 530/326; 530/350

(58) Field of Classification Search
USPC ................ 514/18.9, 21.4, 19.3; 530/326, 350
See application file for complete search history.

(56) References Cited

U.S. PATENT DOCUMENTS

| | | | |
|---|---|---|---|
| 7,723,469 B2 * | 5/2010 | Walensky et al. | 530/317 |
| 2002/0052316 A1 | 5/2002 | Shore et al. | |
| 2005/0191696 A1 | 9/2005 | Goldmakher et al. | |
| 2005/0250680 A1 * | 11/2005 | Walensky et al. | 514/9 |
| 2012/0082636 A1 * | 4/2012 | Walensky et al. | 424/78.17 |

FOREIGN PATENT DOCUMENTS

| | | |
|---|---|---|
| WO | 95/05750 A1 | 3/1995 |
| WO | 2005/044839 A2 | 5/2005 |
| WO | 2006/034454 A1 | 3/2006 |

OTHER PUBLICATIONS

Cartron et al. (Molecular Cell, vol. 16, 807-818, Dec. 3, 2004).*
Bowie et al. (Science 1990; 247: 1306-1310).*
Burgess et al. (Journal of Cell Biology 1990; 111: 2129-2138,).*
Lazar et al. (Molecular and Cellular Biology, 1988, 8: 1247-1252).*
Skolnick et al. (Trends in Biotechnology 2000; 18: 34-39).*
Luque et al. (Biochemistry. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Gura (Science, 1997, 278:1041-1042).*
Kaiser (Science, 2006, 313: 1370).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
W. Jahnke et al., "Second-Site NMR Screening with a Spin-Labeled First Ligand", J. Am. Chem. Soc., vol. 22, pp. 7394-7395 (2000).

* cited by examiner

*Primary Examiner* — Mark Halvorson
*Assistant Examiner* — Yan Xiao
(74) *Attorney, Agent, or Firm* — Fish & Richardson P.C.

(57) ABSTRACT

The present invention is based, at least in part, on the identification of a novel active site on BCL-2 family polypeptide such as BAX, which when bound by a compound, modifies the activity of the BCL-2 family polypeptide.

2 Claims, 26 Drawing Sheets

Figure 1 BCL-2 family members share conserved BCL-2 homology (BH) domains.

Fig 2 (A) Synthesis of a hydrocarbon-stapled peptides of the BCL-2 family polypeptide BH3 domain. (B) Chemical toolbox of SAHB compounds, with examples of two i, i+4 staple locations. Conserved residues are highlighted in yellow. Note that staple locations can be anywhere in peptide sequences.

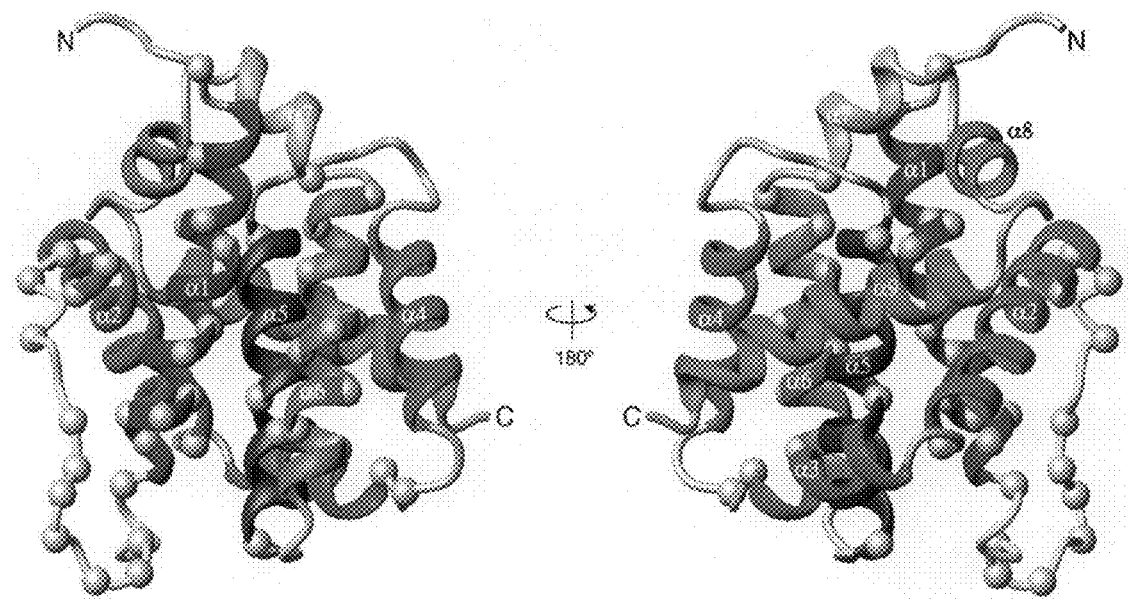

B

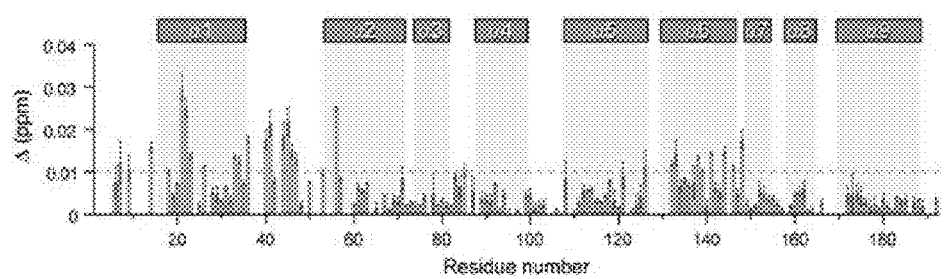

FIGURE 3 (a) A ribbon diagram representing the BAX structure with gray spheres indicating those residues affected by BIM SAHB binding, as determined by NMR analysis of $^{15}$N-labeled BAX upon BIM SAHB titration. (b) Chemical shift changes are plotted as a function of the residue number of BAX. Residues with significant backbone amide chemical shift change (>0.01 ppm) are colored orange.

Figure 4. (a) Surface diagram illustrating the BAX binding site. (b) NMR analysis of the BIM SAHB-BAX interaction demonstrates a new binding site for BH3-mediated BAX activation. BIM SAHB engages BAX at a structural location that is distinct from the canonical BH3 binding site identified for anti-apoptotic proteins.

FIGURE 5

SEQ ID NO:1

HUMAN BAX PRIMARY AMINO ACID SEQUENCE

MDGSGEQPEGGGPTSSEQIMKTGALLLQGFIQDRAERMGEQPEELDPVPQDASTKKL
SECLKRIGDELDSNMELQRMIAAEESPREVFFRVAADMFSDGNFNWGRVVALFYFA
KLLLKALCTKVPELIRTIMGWTLDFLRERLLGWIQDQGGWDGLLSYFGTPTWQTVTIFV
AGVLTASLTIWKKMG

RESIDUES AT BIM SAHB INTERACTION SITE: YELLOW
ADDITIONAL RESIDUES AFFECTED BY BIM SAHB BINDING: RED

FIGURE 5 Primary amino acid sequence of BAX, highlighting key residues in alpha helices 1 and 6, the loop between alpha helices 1 and 2, and select residues in helices 2 and 4 of BAX that participate in forming the novel binding site for activator SAHBs, such as BIM SAHB. Alpha helices 1-9 are underlined sequentially, and alpha helices 1 and 6 are bolded.

FIGURE 6A
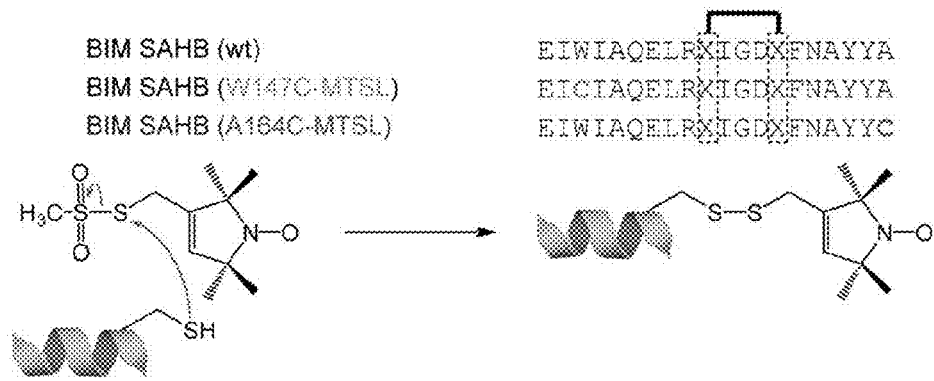
FIGURE 6B-D
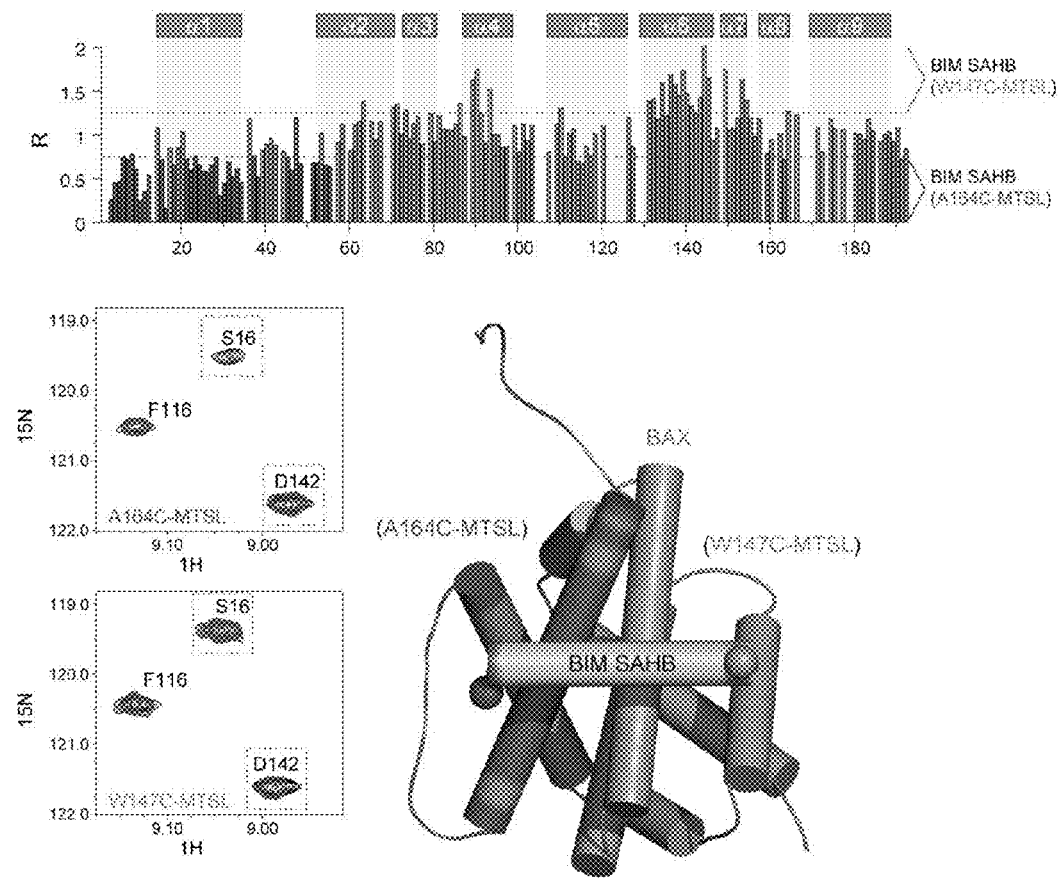

FIGURE 6E

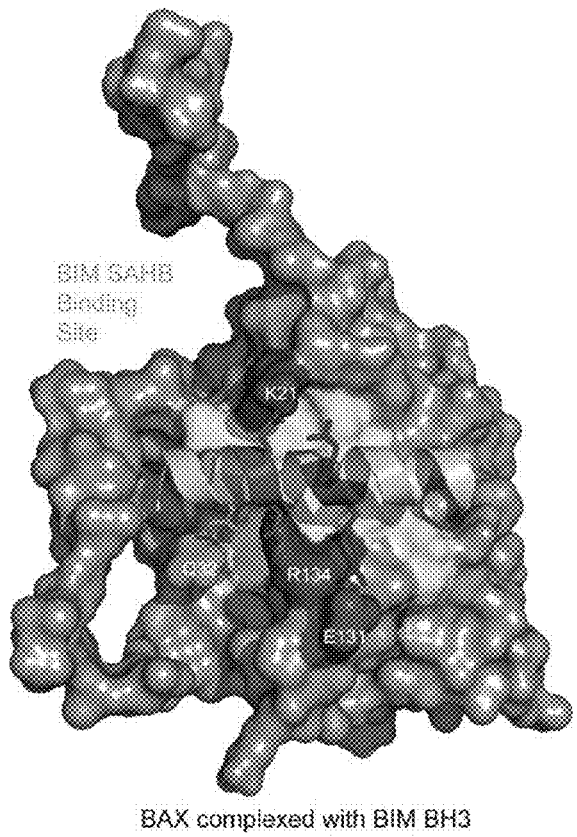

BAX complexed with BIM BH3

Figure 6. Orientation of BIM SAHB at the novel BAX binding site. (a) BIM SAHB was mutated to position a cysteine residue at either the N- or C-terminus of the peptide and paramagnetically-labeled derivatives generated by reacting the installed thiol group with MTSL to incorporate a nitroxide spin label. (b) A ratio plot of BAX crosspeak intensity ratios (BIM SAHB$_{W147C-MTSL}$[$I_{ox}/I_{red}$]/ BIM SAHB$_{A164C-MTSL}$[$I_{ox}/I_{red}$]) versus residue number highlights BAX residues maximally impacted by the respective MTSL labels. (c) Correlation spectra demonstrate that BAX α1 residues (e.g. Ser16) are primarily affected in PRE experiments that compare oxidized (red) and reduced (black) forms of BIM SAHB$_{(A164C-MTSL)}$ (top panel) whereas BAX α6 residues (e.g. D142) are impacted in the corresponding BIM SAHB$_{(W147C-MTSL)}$ studies (bottom panel). (d) The calculated structure generated using the PRE-derived intermolecular distances from both MTSL incorporation sites converged to orient BIM SAHB approximately 90 degrees relative to α-helices 1 and 6, with the N- to C-terminus directionality disposed right to left. (e) Calculated structure of the complex between the novel interaction site on BAX and BIM BH3.

FIGURE 7 Structural comparison of BCL-2 polypeptides highlights morphologic homology to the novel BAX binding site at the interfaces of α-helices 1, 6 and adjacent to the region of the flexible loop between α-helices between 1 and 2.

FIGURE 8
EXAMPLES OF BIM SAHBs

N-term includes: acetyl, FITC-βAla, biotin, propargyl, myristoyl, myristoyl-Lys(FITC), FITC-Lys(myristoyl)
C-term includes: amide, carboxylate

| | |
|---|---|
| hBIM BH3 | EIWIAQELRRIGDEFNAYYARR (SEQ ID NO:3) |
| mBIM BH3 | IRIAQELR*IGD*FNETYTRR |
| mBIM SAHB$_{A2}$ | IRIAQELR*IGD*FNETYTRR |
| mBIM SAHB$_{A2}$ | EIRIAQELR*IGD*FNETYT |
| BIM SAHB$_{A1}$(G→E) | IWIAQELR*IED*FNAYYARR |
| BIM SAHB$_{A1}$(L,D→A,A) | IWIAQEAR*IGA\*FNAYYARR |
| BIM SAHB$_{A1}$(G→S) | IWIAQELR*ISD*FNAYYARR |
| BIM SAHB$_{A1}$(E→R) | IWIAQRLR*IGD*FNAYYARR |
| BIM SAHB$_{A1}$(R→D) | IWIAQELD\*IGD*FNAYYARR |
| BIM SAHB$_{A1}$(E,R→R,D) | IWIAQRLD\*IGD*FNAYYARR |
| BIM SAHB$_{A1}$(W→R) | IRIAQELR*IGD*FNAYYARR |
| BIM SAHB$_{A1}$(A→E) | IWIAQELR*IGD*FNEYYARR |
| BIM SAHB$_{A1}$(Y→T) | IWIAQELR*IGD*FNATYARR |
| BIM SAHB$_{A1}$(A→T) | IWIAQELR*IGD*FNAYYTRR |
| BIM SAHB$_{A2}$(G→E) | EIWIAQELR*IED*FNAYYA |
| BIM SAHB$_{A2}$(L,D→A,A) | EIWIAQEAR*IGA\*FNAYYA |
| BIM SAHB$_{A2}$(G→S) | EIWIAQELR*ISD*FNAYYA |
| BIM SAHB$_{A2}$(E→R) | EIWIAQRLR*IGD*FNAYYA |
| BIM SAHB$_{A2}$(R→D) | EIWIAQELD\*IGD*FNAYYA |
| BIM SAHB$_{A2}$(E,R→R,D) | EIWIAQRLD\*IGD*FNAYYA |
| BIM SAHB$_{A2}$(W→R) | EIRIAQELR*IGD*FNAYYA |
| BIM SAHB$_{A2}$(A→E) | EIWIAQELR*IGD*FNEYYA |
| BIM SAHB$_{A2}$(Y→T) | EIWIAQELR*IGD*FNATYA |
| BIM SAHB$_{A2}$(A→T) | EIWIAQELR*IGD*FNAYYT |
| BIM SAHB$_{A2}$(I→E) | EIWIAQELR*EGD*FNAYYA |
| BIM SAHB$_{A2}$(E→R) | RIWIAQELR*IGD*FNAYYA |
| BIM SAHB$_{A2}$(D→R) | EIWIAQELR*IGR\*FNAYYA |
| BIM SAHB$_{A2}$(N→R) | EIWIAQELR*IGD*FRAYYA |
| BIM SAHB$_{A2}$(N→E) | EIWIAQELR*IGD*FEAYYA |
| BIM SAHB$_{A2}$(D,N→R,E) | EIWIAQELR*IGR\*FEAYYA |
| BIM SAHB$_{A2}$(D,N→R,R) | EIWIAQELR*IGR\*FRAYYA |
| BIM SAHB$_{B1}$ | I*IAQ*LRRIGDEFNAYYARR |
| BIM SAHB$_{B2}$ | EI*IAQ*LRRIGDEFNAYYA |
| BIM SAHB$_{B2}$(E→K) | EI*IAQ*LRRIGDKFNAYYA |
| BIM SAHB$_{C1}$ | IW*AQE*RRIGDEFNAYYARR |
| BIM SAHB$_{C2}$ | EIW*AQE*RRIGDEFNAYYA |
| BIM SAHB$_{D1}$ | IWI*QEL*RIGDEFNAYYARR |
| BIM SAHB$_{D2}$ | EIWI*QEL*RIGDEFNAYYA |
| BIM SAHB$_{E1}$ | IWIAQELRRIGD*FNA*YARR |
| BIM SAHB$_{E2}$ | EIWIAQELRRIGD*FNA*YA |
| BIM SAHB$_{F1}$ | IWIA*ELR*IGDEFNAYYARR |
| BIM SAHB$_{F2}$ | EIWIA*ELR*IGDEFNAYYA |
| BIM SAHB$_{G1}$ | IWIAQELRRIGDEF*AYY*RR |
| BIM SAHB$_{G2}$ | EIWIAQELRRIGDEF*AYY* |

FIGURE 8-Continued

Derivatives include cysteine-based incorporation of MTSL
and lysine-based incorporation of DOTA:

```
BIM SAHB_A2 (W→C/K)      EI(C/K)IAQELR*IGD*FNAYYA
BIM SAHB_A2 (A→C/K)      EIWI(C/K)QELR*IGD*FNAYYA
BIM SAHB_A2 (G→C/K)      EIWIAQELR*I(C/K)D*FNAYYA
BIM SAHB_A2 (Y→C/K)      EIWIAQELR*IGD*FNA(C/K)YA
BIM SAHB_A2 (Y→C/K)      EIWIAQELR*IGD*FNAY(C/K)A
BIM SAHB_A2 (A→C/K)      EIWIAQELR*IGD*FNAYY(C/K)
```

*Sites for hydrocarbon stapling

FIGURE 9
EXAMPLES OF BID SAHB Derivatives
N-term includes: acetyl,FITC-βAla, biotin, propargyl, myristoyl, myristoyl-Lys(FITC), FITC-Lys(myristoyl)
C-term includes: amide, carboxylate

```
hBID BH3              ESQEDIIRNIARHLAQVGDEMDRSI  (SEQ ID NO: 4)
mBID BH3              ESQEEIIHNIARHLAQIGDEBDHNI
BID SAHB_A1               DIIRNIARHLA*VGD*BDRSI
mBID SAHB_A1              EIIHNIARHLA*IGD*BDHNI
BID SAHB_A2           ESQEDIIRNIARHLA*VGD*BDRSI
mBID SAHB_A2          ESQEEIIHNIARHLA*IGD*BDHNI
BID SAHB_A1(G→E)          DIIRNIARHLA*VED*BDRSI
BID SAHB_A1(G→S)          DIIRNIARHLA*VSD*BDRSI
BID SAHB_A1(L,D→A,A)      DIIRNIARHAA*VGA*BDRSI
BID SAHB_A1(B,D→A,A)      DIIRNIARHLA*VGD*AARSI
BID SAHB_A1(G→E)          DIIRNIARHLA*VAD*BDRSI
```

* Sites for hydrocarbon stapling

FIGURE 10
EXAMPLES OF PUMA SAHB Derivatives
N-term includes: acetyl, FITC-βAla, biotin, propargyl
C-term includes: amide, carboxylate

```
hPUMA BH3              EQWAREIGAQLRRMADDLNAQYER (SEQ ID NO:5)
PUMA SAHB_A1           QWAREIGLQAR*BAD*LNAQY
PUMA SAHB_A1(L,D→A,A)  QWAREIGAQAR*BAA*LNAQY
PUMA SAHB_A1(G→E)      QWAREIGLQAR*BED*LNAQY
PUMA SAHB_A1(R→D)      QWAREIGLQAD*BAD*LNAQY
PUMA SAHB_A2           EQWAREIGLQAR*BAD*LNAQY
PUMA SAHB_A3           EQWAREIGLQAR*BAD*LNAQYE
PUMA SAHB_B1           QW*REI*LQARRBADDLNAQY
PUMA SAHB_B3           EQW*REI*LQARRBADDLNAQYE
PUMA SAHB_B1(R→D)      QW*REI*LQADRBADDLNAQY
PUMA SAHB_B3(R→D)      EQW*REI*LQADRBADDLNAQYE
PUMA SAHB_B1(D→R)      QW*REI*LQARRBARDLNAQY
PUMA SAHB_B3(D→R)      EQW*REI*LQARRBARDLNAQYE
```

\* Sites for hydrocarbon stapling

FIGURE 11

BIM, BID, and PUMA SAHB derivatives for covalent capture including point mutants for specificity analyses
N-term: acetyl, FITC-βAla, biotin, propargyl, myristoyl, myristoyl-Lys(FITC), FITC-Lys(myristoyl)
C-term includes: amide, carboxylate

BIM:

| | |
|---|---|
| BIM SAHB$_{A1}$Bpa-1 | IUIAQELR*IGD*FNAYYARR |
| BIM SAHB$_{A1}$Bpa-2 | IWIAQELR*IGD*UNAYYARR |
| BIM SAHB$_{A1}$Bpa-3 | IWIAQELR*IGD*FNAUYARR |
| BIM SAHB$_{A1}$Bpa-4 | IWIAQELR*IGD*FNAYUARR |
| BIM SAHB$_{A1}$Bpa-5 | IRIAQELR*IGD*FNAYUARR |
| BIM SAHB$_{A1}$Bpa-6 | IWIAQELR*IGD*FNEYUARR |
| BIM SAHB$_{A1}$Bpa-7 | IWIAQELR*IGD*FNATUARR |
| BIM SAHB$_{A1}$Bpa-8 | IWIAQELR*IGD*FNAYUTRR |
| BIM SAHB$_{A1}$Bpa-9 | IWIAQELD*IGD*FNAYUARR |
| BIM SAHB$_{A1}$Bpa-10 | IWIAQRLR*IGD*FNAYUARR |
| BIM SAHB$_{A1}$Bpa-11 | IWIAQRLD*IGD*FNAYUARR |
| BIM SAHB$_{A2}$Bpa-1 | EIUIAQELR*IGD*FNAYYA |
| BIM SAHB$_{A2}$Bpa-2 | EIWIAQELR*IGD*UNAYYA |
| BIM SAHB$_{A2}$Bpa-3 | EIWIAQELR*IGD*FNAUYA |
| BIM SAHB$_{A2}$Bpa-4 | EIWIAQELR*IGD*FNAYUA |
| BIM SAHB$_{A2}$Bpa-5 | EIRIAQELR*IGD*FNAYUA |
| BIM SAHB$_{A2}$Bpa-6 | EIWIAQELR*IGD*FNEYUA |
| BIM SAHB$_{A2}$Bpa-7 | EIWIAQELR*IGD*FNATUA |
| BIM SAHB$_{A2}$Bpa-8 | EIWIAQELR*IGD*FNAYUT |
| BIM SAHB$_{A2}$Bpa-9 | EIWIAQELD*IGD*FNAYUA |
| BIM SAHB$_{A2}$Bpa-10 | EIWIAQRLR*IGD*FNAYUA |
| BIM SAHB$_{A2}$Bpa-11 | EIWIAQRLD*IGD*FNAYUA |

BID:

| | |
|---|---|
| BID SAHB$_{A1}$ Bpa-1 | UDIIRNIARHLA*VGD*BDRSI |
| BID SAHB$_{A1}$ Bpa-2 | DIIRUIARHLA*VGD*BDRSI |
| BID SAHB$_{A1}$ Bpa-3 | DIIRNIARHLA*VGD*UDRSI |
| BID SAHB$_{A1}$ Bpa-4 | DIIRNIARHLA*VGD*BDRUI |
| BID SAHB$_{A1}$ Bpa-5 | DIIRNIARHLA*VGD*BDRSU |

PUMA:

| | |
|---|---|
| PUMA SAHB$_{A1}$ Bpa-1 | UQWAREIGLQAR*BAD*LNAQY |
| PUMA SAHB$_{A1}$ Bpa-2 | QUAREIGLQAR*BAD*LNAQY |
| PUMA SAHB$_{A1}$ Bpa-3 | QWARUIGLQAR*BAD*LNAQY |
| PUMA SAHB$_{A1}$ Bpa-4 | QWAREIGLQAR*BAD*UNAQY |
| PUMA SAHB$_{A1}$ Bpa-5 | QWAREIGLQAR*BAD*LNAUY |
| PUMA SAHB$_{A1}$ Bpa-6 | QWAREIGLQAR*BAD*LNAQU |

BIM, BID, and PUMA SAHBs and their derivatives and mutants developed for covalent capture of binding targets. U = Bpa, but could also represent other crosslinkable moieties known in the art.
* Sites for hydrocarbon stapling Figure 12. BIM SAHB directly initiates BAX oligomerization *in vitro* as demonstrated by (a) size exclusion chromatography-based monitoring of the monomer-oligomer states and (b) 6A7 antibody-based recognition of activated BAX with increasing BIM SAHB-BAX ratios.

FIGURE 12 continued. Specific and high potency BIM SAHB-induced direct BAX activation as assessed by (c) an *in vitro* FITC-dextran liposomal release assay and (d) mitochondrial cytochrome *c* release.

FIGURE 13. Specificity of BIM SAHB-induced BAX activation: Point Mutagenesis.
(a) A panel of BIM SAHB compounds mutated at its interaction surface with BAX. (b) Point mutagenesis of BIM SAHB abrogates its capacity to oligomerize wild-type BAX and (c) trigger BAX-mediated cytochrome c release. (c) BAX K21E and R134E mutagenesis impairs BIM SAHB-induced BAX oligomerization.

FIGURE 13A

BIM SAHB (wt)     EIWIAQELRXIGDXFNAYYA
BIM SAHB (R153D)  EIWIAQELDXIGDXFNAYYA
BIM SAHB (I155E)  EIWIAQELRXEGDXFNAYYA
BIM SAHB (D157R)  EIWIAQELRXIGRXFNAYYA

FIGURE 13B

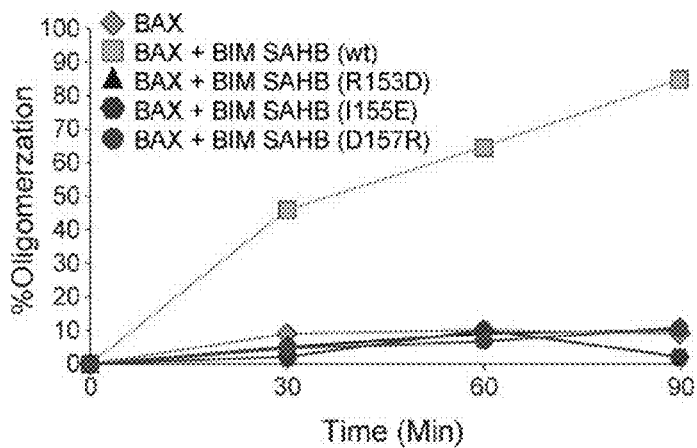

FIGURE 14D

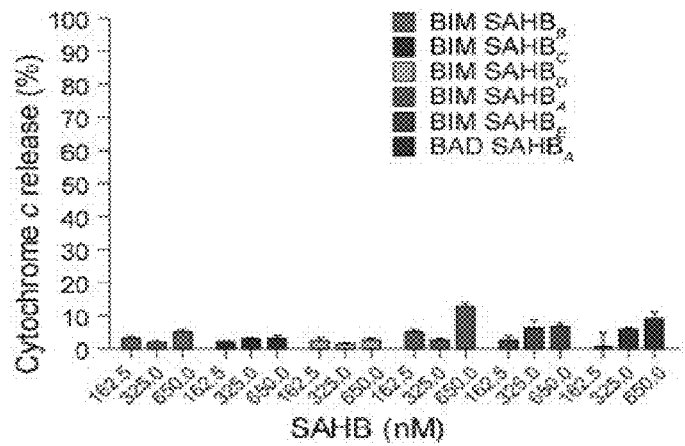

FIGURE 14. Specificity of BIM SAHB-induced BAX activation: Staple Scan.
(a) A panel of BIM SAHB compounds with differential i, i+4 staple positions. (b) Replacement of core hydrophobic residues I148 and L152 by a hydrocarbon staple localized to the hydrophobic interaction surface of BIM SAHB selectively impaired BAX oligomerization. Localization of hydrocarbon staples along the non-interacting surface of the BIM BH3 α-helix uniformly preserved BIM SAHB-induced BAX oligomerization. Despite having the identical staple position as BIM SAHB$_A$, BAD SAHB$_A$ did not induce BAX oligomerization. (c) Correspondingly, BIM SAHBs A, B, D, and E triggered BAX-mediated cytochrome c release, whereas BIM SAHB$_C$ and BAD SAHB$_A$ had little to no effect, respectively. (d) Control experiment demonstrating that SAHB-induced mitochondrial cytochrome c release is BAX-dependent.

FIGURE 15

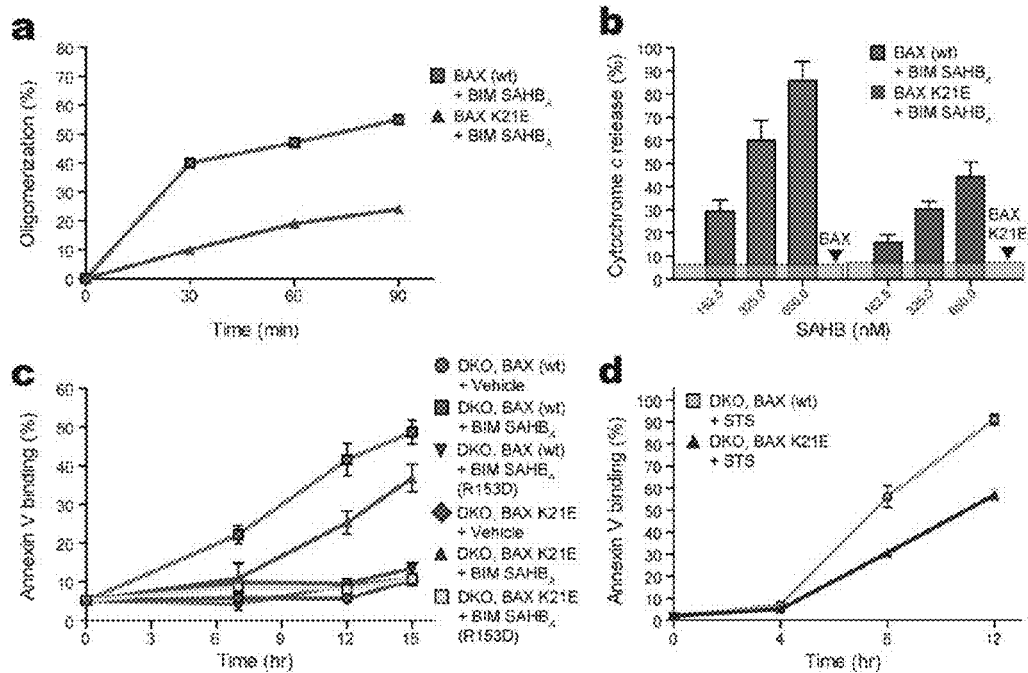

Fig 15 Mutagenesis of the BAX Interaction Site Impairs Activation and BAX-mediated Apoptosis. (a) BAX K21E mutagenesis impaired BIM SAHB$_A$-induced BAX oligomerization and (b) reduced BAX-mediated cytochrome c release. (c) Bax$^{-/-}$Bak$^{-/-}$ MEFs reconstituted with wild-type BAX underwent apoptosis in response to BIM SAHB$_A$ but not BIM SAHB$_{A(R153D)}$, as assessed by annexin-V binding. Bax$^{-/-}$Bak$^{-/-}$ MEFs reconstituted with BAX$_{K21E}$ demonstrated a blunted apoptotic response to BIM SAHB$_A$. (d) Staurosporine (STS)-induced apoptosis of BAX-reconstituted DKO MEFs was likewise reduced by K21E mutagenesis. Error bars indicate the mean of at least triplicate values ± s.d.

FIGURE 16 BAX SAHBs modeled after BAX and BAX BH3 and BAX ☐-helix 9, designed to modulate BAX oligomerization.

FIGURE 16A
BAX BH3 SAHBs

```
BAX BH3 WT        QDASTKKLSECLKRIGDELDSN (SEQ ID NO:12)
BAX SAHB_A        QDASTKKLSECLK*IGD*LDSN
BAX SAHB_B        QDASTK*LSE*LKRIGDELDSN
BAX SAHB_B(R→D)   QDASTK*LSE*LDRIGDELDSN
BAX SAHB_B(D→R)   QDASTK*LSE*LKRIGRELDSN
BAX SAHB_C        QDASTKK*SEC*KRIGDELDSN
BAX SAHB_D        QDASTKKL*ECL*RIGDELDSN
```

FIGURE 16B
BAX Helix 9 SAHBs

```
BAX_H9 WT         TWQTVTIFVAGVLTASLTIWKK (SEQ ID NO:14)
BAX_H9 SAHB_A1    TWQTVTIFVA*VLT*SLTIWKK
BAX_H9 SAHB_A2    TWQTVTDFVA*VLT*SLTIWKK
BAX_H9 SAHB_A3    TWETVTDFVA*CLT*SLTIWKK
BAX_H9 SAHB_A4    TWETVTDFVA*VLT*SLRIWKK
BAX_H9 SAHB_B1    TWQTVT*FVA*VLTASLTIWKK
BAX_H9 SAHB_B2    TWQTVT*FVA*VLTDSLTIWKK
BAX_H9 SAHB_B3    TWETVT*FVA*VLTDSLTIW
BAX_H9 SAHB_B4    TWETVT*FVA*VLTDSLRIWKK
```

*Sites for hydrocarbon stapling

FIGURE 17
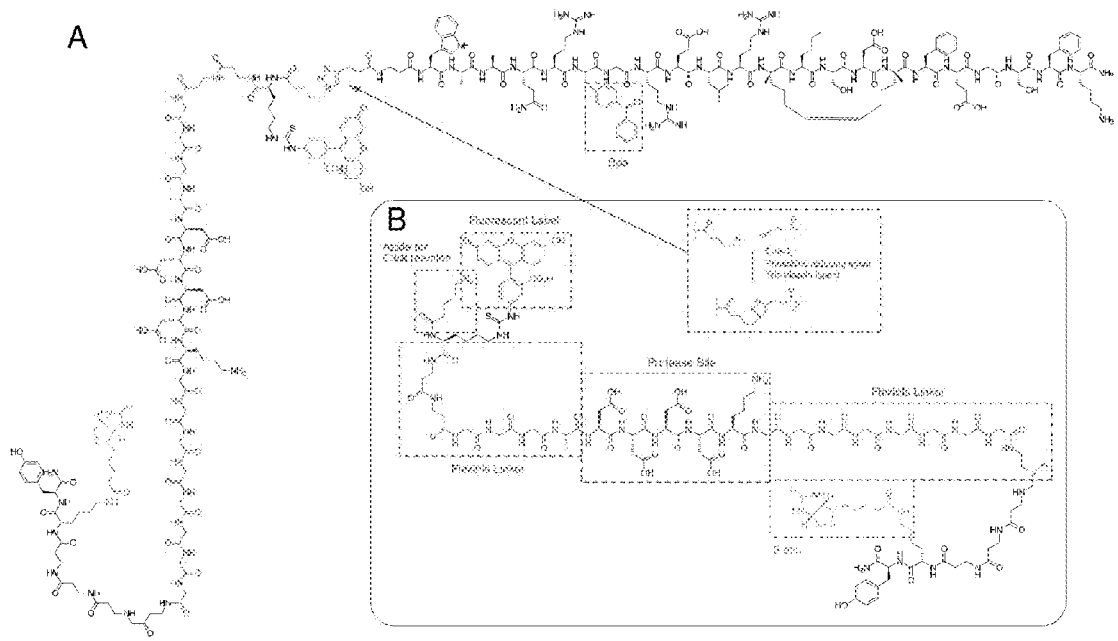
Fig 17 Chemical design of polyfunctional SAHB compound for covalent capture of physiologic targets. Bpa moiety can be substituted for other crosslinkable/intercalating moieties.
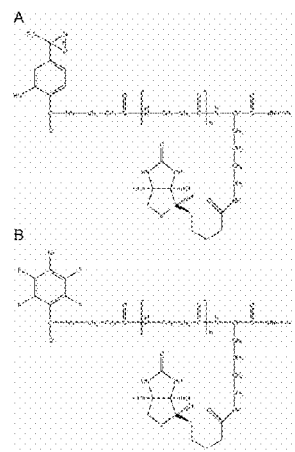
Fig 18 SAHBs derivatized with photo-labile carbene (A) and nitrene (B) generating functionalities.

FIGURE 20A

Human BIM-SEQ ID NO:2

BIML

MAKQPSDVSSECDREGRQLQPAERPPQLRPGAPTSLQTEPQDRSPAPMSCDKSTQTPSP
PCQAFNHYLSAMASMRQAEPADMRPEIWIAQELRRIGDEFNAYYARRVFLNNYQAAEDH
PRMVILRLLRYIVRLVWRMH

Leu92
Gly96
Asp97

BIMEL --SEQ ID NO:9

MAKQPSDVSSECDREGRQLQPAERPPQLRPGAPTSLQTEPQGNPEGNHGGEGDSCPHGS
PQGPLAPPASPGPFATRSPLFIFMRRSSLLSRSSSGYFSFDTDRSPAPMSCDKSTQTPS
PPCQAFNHYLSAMASMRQAEPADMRPEIWIAQELRRIGDEFNAYYARRVFLNNYQAAED
HPRMVILRLLRYIVRLVWRMH

Leu152
Gly156
Asp157

Human BID-SEQ ID NO:6

MDCEVNNGSSLRDECITNLLVFGFLQSCSDNSFRRELDALGHELPVLAPQWEGYDELQT
DGNRSSHSRLGRIEADSESQEDIIRNIARHLAQVGDSMDRSIPPGLVNGLALQLRNTSR
SEEDRNRDLATALEQLLQAYPRDMEKEKTMLVLALLLAKKVASHTPSLLRDVFHTTVNF
INQNLRTYVRSLARNGMD

Leu90
Gly94
Asp95

Human PUMA-SEQ ID NO:7

PUMA-α

MARARQEGSSPEPVEGLARDGPRPFPLGRLVPSAVSCGLCEPGLAAAPAAPTLLPAAYL
CAPTAPPAVTAALGGSRWPGGPRSRPRGPRDGQPSLSLAEQHLESPVPSAPGALAGG
PTQAAPGVRGEEEQWAREIGAQLRRMADDLNAQYERRRQEEQQRHRPSPWRVLYNLIMG
LLPLPRGHRAPEMEPN

Leu141

FIGURE 20A-CONTINUED

Ala145
Asp146

PUMA-β  SEQ ID NO:10

MKFGMGSAQACPCQVPRAASTTWVPCQICGPQPSLSLAEQHLESPVPSAPGALAGGPTQ
AAPGVRGEEEQWAREIGAQLRRMADDLNAQYERRRQEEQQRHRPSPWRVLYNLIMGLLP
LPRGHRAPEMEPN

Leu79
Ala83
Asp84

Human BCL-2 SEQ ID NO:8

BCL-2-α

MAHAGRTGYDNREIVMKYIHYKLSQRGYEWDAGDVGAAPPGAAPAPGIFSSQPGHTPHP
AASRDPVARTSPLQTPAAPGAAAGPALSPVPPVVHLTLRQAGDDFSRRYRRDFAEMSSQ
LHLTPFTARGRFATVVEELFRDGVNWGRIVAFFEFGGVMCVESVNREMSPLVDNIALWM
TEYLNRHLHTWIQDNGGWDAFVELYGPSMRPLFDFSWLSLKTLLSLALVGACITLGAYL
GHK

Leu97
Gly101
Asp102

BCL-2-β  SEQ ID NO:11

MAHAGRTGYDNREIVMKYIHYKLSQRGYEWDAGDVGAAPPGAAPAPGIFSSQPGHTPHP
AASRDPVARTSPLQTPAAPGAAAGPALSPVPPVVHLTLRQAGDDFSRRYRRDFAEMSSQ
LHLTPFTARGRFATVVEELFRDGVNWGRIVAFFEFGGVMCVESVNREMSPLVDNIALWM
TEYLNRHLHTWIQDNGGWVGALGDVSLG

Leu97
Gly101
Asp102

FIGURE 20b

Conserved residues among BIM, PUMA, and BAX BH3 domains at alpha-helical interaction surface:

```
BIM BH3     EIWIAQELRRIGDEFNAYYARR
PUMA BH3    EQWAREIGAQLRRMADDLNAQYER
BAX BH3     QDASTKKLSECLKRIGDELDSNMELQR
```

Yellow: amino acid identity
Blue: conserved change

Consensus (SEQ ID NO:13):
I/L A/S/G X X L K/R R I/M/V D D/E L/F N/D A/S X Y/M

METHODS AND COMPOSITIONS FOR MODULATING BCL-2 FAMILY POLYPEPTIDES

RELATED APPLICATIONS

This application is the National Phase Application of PCT/US2008011500 (WO2009/042237), filed on Sep. 26, 2008 which claims the benefit of U.S. Provisional Application Nos. 60/995,545, filed on Sep. 26, 2007 and 61/124,221, filed on Apr. 14, 2008. The entire teachings of the above applications are incorporated herein by reference.

STATEMENT OF U.S. GOVERNMENT INTEREST

Funding for the present invention was provided in part by support from the Intramural Research Program of the National Heart Lung and Blood Institute, a component of the U.S. National Institutes of Health. Accordingly, the Government of the United States may have certain rights in and to the invention.

BACKGROUND

BCL-2 family protein interactions regulate apoptosis, an orchestrated set of events designed to rid the body of damaged or unwanted cells, and a process critical for normal development and organism homeostasis (Adams, J. M., and Cory, S. (1998), Science 281, 1322-1326; Danial, N. N., and Korsmeyer, S. J. (2004), Cell 116, 205-219). Whereas multidomain anti-apoptotic proteins such as BCL-2 guard against cell death, multidomain pro-apoptotic proteins such as BAX constitute a gateway to cell death through mitochondrial damage. Multidomain apoptotic proteins display sequence conservation in up to four BCL-2 homology (BH) domains, yet the "BH3-only" subset of pro-apoptotic proteins displays homology only to the third BH domain. The BH3-only proteins function as death sentinels situated throughout the cell, poised to transmit signals of cell injury to multidomain members. Depending on the nature of apoptotic stimuli and cellular context, the BH3-only protein's death signal will either be neutralized by anti-apoptotic proteins or delivered, directly or indirectly, to the mitochondrial executioners BAX and BAK. When activated, these pro-apoptotic multidomain members induce permeabilization of the outer mitochondrial membrane, enabling released mitochondrial factors to activate caspases, which irreversibly execute the death program (Green, D. R. (2005). Cell 121, 671-674).

Structural studies have demonstrated the insertion of BH3 ligands into the hydrophobic groove formed by the juxtaposition of BH1, BH2 and BH3 domains of anti-apoptotic multidomain members (Day, C. L., et al. (2005), J Biol Chem 280, 4738-4744; Denisov, A. Y., (2003), J Biol Chem 278, 21124-21128; Liu, X., et al. (2003), Immunity 19, 341-352). Recent work has uncovered the binding specificities of BH3-only members for their anti-apoptotic partners and the structural basis for these selectivities (Certo, M., Moore, et. Al. (2006), Cancer Cell 9, 351-365.; Chen, L., et al. (2005); Mol Cell 17, 393-403). BH3-only proteins antagonize anti-apoptotic proteins through these direct interactions, and thereby decreases anti-apoptotic inhibition of BAX/BAK and/or competitively displace bound BH3-only members that are capable of direct activation of BAX/BAK. BH3-only proteins that exclusively engage anti-apoptotic proteins to exert their pro-apoptotic activity (e.g. BAD) have thus been termed "sensitizers"(Letai, A., et al. (2002), Cancer Cell 2, 183-192) or "derepressors" (Kuwana, T., et al. (2005)1 Mol Cell 17, 525-535).

Recent yeast two-hybrid, immunoprecipitation, and biochemical studies support a role for select BH3-only members, including BID and BIM, in direct activation of BAX. (Carton, P. F., et al. Mol Cell 16, 807-818 (2004); Harada, H., et al. PNAS USA 101, 15313-15317 (2004); Marani, M., et al. Mol Cell Biol 22, 3577-3589 (2002); Walensky, L. D., et al. Mol Cell 24, 199-210 (2006); Wang, K., et al. Genes Dev 10, 2859-2869. (1996). However, the inability to measure a direct binding affinity between the BH3 domain of these "activator" BH3-only proteins and native BAX protein, and the requirement of up to 50 micromolar dosing of activating BH3 peptides to trigger BAX activation in vitro (Kuwana, T., et al. (2005). Mol Cell 17, 525-535; Kuwana, T., et al. (2002). Cell 111, 331-342), have led to uncertainty about the existence of a BH3-mediated direct BAX/BAK activation pathway. In fact, the lack of binding and structural data to support such interactions has led to the hypothesis that the pro-apoptotic potency of presumed activator peptides, such as BIM BH3, may instead reflect their ability to effectively neutralize all anti-apoptotic proteins tested to date.

SUMMARY OF THE INVENTION

The present invention is directed to methods, kits and compositions for modulating the activity of BCL-2 family polypeptides (e.g., BAX) by targeting a new regulatory site on BCL-2 family proteins. The methods and compounds of the invention are useful for treating and/or preventing disorders characterized by the deregulation of one or more polypeptides of the BCL-2 family, including conditions of premature cell death (e.g. diabetes, neurodegenerative disease, heart attach, stroke), or pathologic cell survival (e.g. autoimmune disease, cancer). Further, the methods and compounds of the present invention are also useful in the treatment of non-BCL-2 related disorders associated with excessive cellular proliferation or excessive cellular death (e.g., apoptosis). The present invention is based, at least in part, on the identification of a novel active site on a BCL-2 family polypeptide such as BAX, which when bound by a compound, modifies the apoptotic activity of the BCL-2 family polypeptide.

In a first aspect, the invention is directed to a method for identifying a compound which modulates the activity of a BCL-2 family polypeptide. The method includes contacting a BCL-2 family polypeptide with a compound which binds to an active site in the polypeptide and detecting a modulated activity of the polypeptide, thereby identifying a BCL-2 family polypeptide modulator.

In a further aspect, the invention is directed to a method for identifying a compound which activates or inhibits the apoptotic activity of a BCL-2 family polypeptide, such as BAX. The method includes, for example, contacting the BAX polypeptide with a compound which modulates (e.g., activates) BAX when bound to one or more of amino acid residues including Glu17, Met20, Lys21, Thr22, Ala24, Leu25, Leu27, Gln28, Gly29, Ile31, Gln 32, Asp 33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg 147 of a BAX active site, and detecting activation or inhibition of the biological activity of BAX, thereby identifying a BAX activator or inhibitor.

In yet another aspect, the invention is directed to a method for identifying a candidate modulator of a BCL-2 family polypeptide. The method entail using a three dimensional structure (e.g., interaction template) of an active site of the BCL-2 family polypeptide, and employing the three dimensional structure to select a BCL-2 family polypeptide candidate modulator from a group of compounds. A compound is identified as a candidate modulator when it binds to the active site of the BCL-2 family polypeptide.

In a further aspect, the invention is directed to a method for identifying a candidate compound which activates or inhibits the apoptotic activity of a BCL-2 family polypeptide, such as BAX. For example, the method includes: providing a three dimensional structure of an active site of the BAX polypeptide, simulating a binding interaction between the active site and a compound; and determining whether the compound binds to one or more BAX residues including Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg 147 of the active site. A compound is identified as a candidate compound when it is capable of binding to one or more of the amino acid residues of the active site.

In yet another aspect, the present invention is directed to a method for treating or preventing a BCL-2 related disorder in an individual. The method involves administering to an individual in need thereof, a pharmacologically effective dose of a compound that binds to an active site of the BCL-2 family polypeptide to either activate or inhibit its apoptotic or other disease-related activity.

In yet a further embodiment, the invention is directed to a method of treating or preventing a disorder of deregulated apoptosis (e.g., hyperpoliferative disorder, diabetes) in an individual, by activating or inhibiting the apoptotic activity of a BAX polypeptide. The method entails administering to an individual in need thereof, a pharmacologically effective dose of a BH3 polypeptide, or chemical mimetic thereof, which binds to one or more amino acid residues including Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg 147 of the active site of BAX so as to activate or inhibit the apoptotic activity of the BAX polypeptide.

In another aspect, the invention is directed to a compound for treating or preventing a BCL-2 related disorder in an individual. The compound modulates the activity of a BCL-2 family polypeptide when bound to an active site of the BCL-2 family polypeptide.

In a further aspect, the invention is directed to a compound for treating or preventing a disorder of deregulated apoptosis (e.g., hyperpoliferative disorder, diabetes) in an individual. The compound is a BH3 polypeptide or chemical mimetic thereof that activates or inhibits the pro-apoptotic activity of a BAX polypeptide when bound to one or more amino acid residues including Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1.

In yet another aspect, the invention is directed to a composition having a BIM BH3 polypeptide having the amino acid sequence represented in FIG. 8. In yet another aspect, the invention is directed to a composition having a BIM BH3 polypeptide having an amino acid sequence which is at least 40% identical to that of SEQ ID NO:3 and which includes interacting residues Ile148, Ala149, L152, Arg153, Arg154, Ile155, Gly156, Asp157, Glu158, Asn160, Ala161, Tyr163, or conserved amino acid substitutions thereof. In yet another aspect, the invention is directed to a composition having 40% identity to alternative BH3 polypeptides that bind the active site on BAX, such as the BH3 domains of BID, PUMA, and/or BAX.

In another aspect, the invention is directed to using the sequence and three dimensional structure of the BAX activation site to identify homologous regulatory sites in the other BCL-2 family members. For example, based upon three dimensional structural similarities or alignment of polypeptide sequences, regions homologous to the BAX activation site would be identified and then tested for the capacity of an interacting compound to modulate the apoptotic activity the BCL-2 polypeptides.

In another aspect, the invention is directed to a BH3 SAHB polypeptide that includes one or more crosslinkable moieties and methods of use thereof. For example, the crosslinkable BH3 SAHBs can be used in methods for identifying an active site on a target polypeptide. The method includes incubating the target polypeptide with a BH3 SAHB polypeptide comprising a covalent crosslinkable moiety, crosslinking the BH3 SAHB polypeptide to the target polypeptide, and identifying the intercalation site of the BH3 SAHB polypeptide to the target polypeptide.

In still another aspect, the invention is directed to kits containing any of the above compounds and instructions for use.

BRIEF DESCRIPTION OF THE DRAWINGS

FIG. 3a is a ribbon diagram representing the BAX structure showing the helices α1-α9. The $C^\alpha$ atoms of BAX residues affected by BIM SAHB binding are shown as grey spheres. The view on the right panel is a 180° rotation from that on the left panel, showing that the residues affected by BIM SAHB are mostly on the one side of the protein structure. All ribbon diagrams of the protein structure were produced using MOLMOL. FIG. 3b documents the chemical shift changes of backbone amides in $^{15}N$-labeled BAX upon BIM SAHB titration. Chemical shift changes are plotted as a function of the residue number of BAX. Residues with significant backbone amide chemical shift change (>0.01 ppm) are colored orange.

FIG. 5 illustrates one embodiment of the full-length BAX amino acid sequence (SEQ ID NO:1) illustrating residues that comprise the BIM SAHB interaction site (highlighted in yellow) and additional residues (highlighted in red) that are affected by conformational changes and/or other interactions upon BIM SAHB binding.

FIG. 6 Orientation of BIM SAHB at the novel BAX binding site. (a) BIM SAHB was mutated to position a cysteine residue at either the N- or C-terminus of the peptide and paramagnetically-labeled derivatives generated by reacting the installed thiol group with MTSL to incorporate a nitroxide spin label. (SEQ ID NOs: 35-37, respectively in order of appearance) (b) A ratio plot of BAX crosspeak intensity ratios (BIM SAHB$_{W147C-MTSL}$[I$_{ox}$/Ir$_{ed}$]/BIM SAHB$_{A164C-MTSL}$[Iox/I$_{red}$]) versus residue number highlights BAX residues maximally impacted by the respective MTSL labels. (c) Correlation spectra demonstrate that BAX α1 residues (e.g. Ser16) are primarily affected in PRE experiments that compare oxidized (red) and reduced (black) forms of BIM SAHB$_{(A164C-MTSL)}$ (top panel) whereas BAX α6 residues (e.g. D142) are impacted in the corresponding BIM SAHB$_{(W147C-MTSL)}$ studies (bottom panel). (d) The calculated structure generated using the PRE-derived intermolecular distances from both MTSL incorporation sites converged to orient BIM SAHB approximately 90 degrees relative to α-helices 1 and 6, with the N- to C-terminus directionality disposed right to left. (e) Calculated structure of the complex between the novel interaction site on BAX and BIM BH3.

FIG. 8 illustrates numerous BIM SAHB polypeptides (SEQ ID NOs: 3 and 38-86, respectively in order of appearance).

FIG. 9 illustrates numerous BID SAHB polypeptides (SEQ ID NOs: 4 and 87-96, respectively in order of appearance).

FIG. 10 illustrates numerous PUMA SAHB polypeptides (SEQ ID NOs: 5 and 97-108, respectively in order of appearance).

FIG. 11 illustrates numerous BIM, BID and PUMA SAHB derivatives that can be used in crosslinking assays. U=Bpa but can represent any other known crosslinkable moieties (SEQ ID NOs: 109-148, respectively in order of appearance).

FIG. 15 illustrates that mutagenesis of the BAX interaction site impairs BAX oligomerization (a), BAX-mediated cytochrome c release (b), and both BIM SAHB (c) and staurosporine-induced (d) apoptosis of BAX-reconstituted Bax$^{-/-}$Bak$^{-/-}$ mouse embryo fibroblasts.

FIG. 16 illustrates examples of (a) BAX BH3 SAHBs (SEQ ID NOs: 12 and 150-155, respectively in order of appearance)and (b) BAX helix 9 SAHBs (SEQ ID NOs: 14and 156-163, respectively in order of appearance).

FIG. 17 depicts the chemical design of polyfunctional SAHB compounds for covalent capture of physiologic targets.

FIG. 18 illustrates SAHBs derivatized with a photolabile (a) carbene generating functionality (a) photolabile nitrene generating functionality.

FIG. 20(a) illustrates the amino acid sequence and highlights highly conserved amino acids among the BH3 regions of BCL-2 family polypeptides, such as BIM, BID, PUMA, BAX, and BCL-2, including identification of a (b) consensus sequence in BIM BH3(SEQ ID NO: 3), PUMA BH3(SEQ ID NO: 5), and BAX BH3(SEQ ID NO: 164) domains for binding the novel BAX interaction site.

DETAILED DESCRIPTION

I. Definitions

Figure 1:
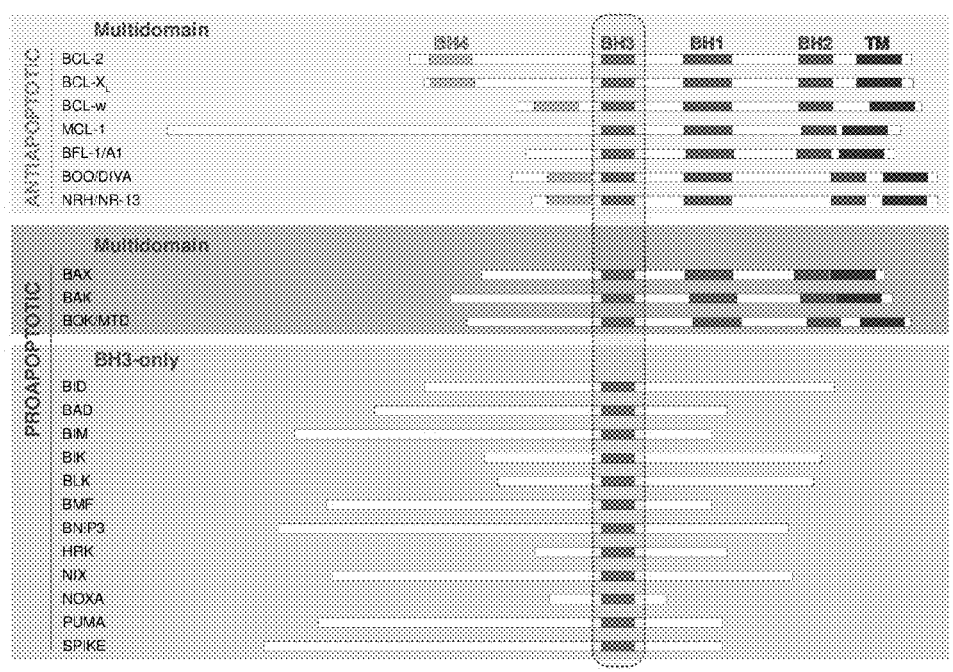
FIG. 1 illustrates several of the BCL-2 family polypeptides involved in the regulation of apoptosis and their conserved BCL-2 homology (BH) domains.

As used herein, the term, "BCL-2 family polypeptide" refers to an evolutionary conserved family of proteins having as few as one to as many as four conserved BCL-2 homology domains (BH1, BH2, BH3 and/or BH4). The BH domains are alpha-helical segments and are present in both the anti-apoptotic and pro-apoptotic polypeptides of the BCL-2 family. BCL-2 family polypeptides include BCL-2, BCL-Xl, BCL-w, MCL-1, BCL-B, A1/BFL-1, BOO/DIVA, Nr-13, CED-9, BAX, BAK, BOK/MTD, BID BAD, BIK/NBK, BLK HRK BIM/BOD, BNIP3, NIX, NOXA, PUMA, BMF AND EGL-1, and viral homologues.

The term "active site" refers to a region of a BCL-2 family polypeptide, as a result of its shape, amino acid content, and charge potential, that favorably interacts or associates with another agent (including, without limitation, a protein, polypeptide, peptide, molecule, compound, antibiotic or drug) via various covalent and/or non-covalent binding forces. The "active site" includes a hydrophobic patch and a perimeter of charged and hydrophilic residues capable of binding a stabilized alpha helix of BCL-2 domain, such as human hydrocarbon-stapled BIM BH3 (SEQ ID NO:3), and which is formed by the juxtaposition of alpha helices 1 and 6 of BAX. The active site may further include amino acid residues from the α1-α2 loop and helix 4 of BAX. In one embodiment, the active site includes two or more amino acids corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1.

The term "BCL-2 family polypeptide variant" refers to polypeptides that vary from a reference BCL-2 family polypeptide by the addition, deletion or substitution of at least one amino acid. It is well understood in the art that some amino acids may be changed to others with broadly similar properties without changing the nature of the activity of the polypeptide (conservative substitutions) as described hereinafter. Accordingly, BCL-2 family polypeptide variants as used herein encompass polypeptides that have pro- or anti-apoptotic activity. The term "variant" refers to a protein having at least 30% amino acid sequence identity with a reference BCL-2 homology domain within a protein or any other functional domain thereof. More specifically, the term "variant" includes, but is not limited to, a BCL-2 family polypeptide comprising an active site characterized by a three dimensional structure comprising the relative structural coordinates of at least two BAX amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1, in each case, +/−a root mean square deviation from the conserved backbone atoms of those residues of not more than 1.1 angstroms, more preferably not more than 1.0 angstroms, and most preferably not more than 0.5 angstroms.

A "BCL-2 family polypeptide variant" further includes those polypeptides, or their biologically active fragments, that comprise an amino acid sequence which is at least 30%, 40%, 50%, 60%, 70%, 80%, 90%, 95%, 96%, 97%, 98%, 99% or more similar to an amino acid sequence of a BCL-2 homology domain (e.g., BH3 domain). In a preferred embodiment, the BCL-2 homology domain comprises one or more conserved amino acid residue, such as amino acid residues corresponding to Leu 92, Gly 96 and Asp 97 of BIM (SEQ ID NO:2) or conservative substitutions thereof.

The term "hydrophobic patch" refers to the portion of the active site that binds a hydrophobic moiety. In one embodiment, the hydrophobic patch contains 1, 2, 3 or more hydrophobic amino acid residues. In one particular embodiment, the hydrophobic pocket contains amino acid residues corresponding to Ala 24, Met 20, Leu 25, Leu 27, Ile 31, Ile 133, Met 137, Gly 138, Trp 139, Leu 141 of SEQ ID NO:1.

The term "charged/hydrophilic perimeter" refers to the portion of the active site that binds a charged or hydrophilic moiety. In one embodiment, the charged/hydrophilic patch contains 1, 2, 3 or more charged or hydrophilic amino acid residues that surround the hydrophobic patch. In one particular embodiment, the charged/hydrophilic perimeter contains amino acid residues corresponding to Lys 21, Gln 28, Gln 32, Asp 33, Gln 52, Glu 17, Arg, 134, Thr 135, Asp 142, Arg 145, Arg 147 of SEQ ID NO:1.

The term "hydrophobic amino acid" means any natural or non-natural amino acid or mimetic thereof having an uncharged, non-polar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any natural or non-natural amino acid or mimetic thereof having an uncharged, polar side chain that is relatively soluble in water. Examples of naturally occurring hydrophilic amino acids are serine, threonine, tyrosine, asparagine, glutamine, and cysteine.

The term "negatively charged amino acid" includes any naturally occurring or unnatural amino acid or mimetic thereof having a negatively charged side chain under normal physiological conditions. Examples of negatively charged naturally occurring amino acids are aspartic acid and glutamic acid.

The term "positively charged amino acid" includes any naturally occurring or unnatural amino acid or mimetic thereof having a positively charged side chain under normal physiological conditions. Examples of positively charged naturally occurring amino acids are arginine, lysine and histidine.

The term "anti-apoptotic polypeptide" refers to BCL-2 family polypeptides characterized by having one or more amino acid homology domains, BH1, BH2, BH3, and/or BH4, and that promote cell survival by attenuating or inhibiting apoptosis. The "anti-apoptotic polypeptides" further include those proteins, or their biologically active fragments, that are at least 30%, 40%, 50%, 60%, 70%, 80%, 90%, 95%, 96%, 97%, 98%, 99% or more similar in amino acid sequence to an anti-apoptotic BCL-2 homology domain within a BCL-2 family polypeptide. In a preferred embodiment, the BCL-2 homology domain comprises one or more conserved amino acid residue, such as amino acid residues corresponding to Leu 97, Gly 101 and Asp 102 of Bcl-2 (SEQ ID NO:8): Anti-apoptotic polypeptides include BCL-2, BCL-Xl, BCL-w, MCL-1, BCL-B, A1/BFL-1, BOO/DIVA, Nr-13 or CED-9, and viral homologues.

The term "pro-apoptotic polypeptide" refers to BCL-2 family polypeptides characterized by having one or more amino acid homology domains, including BH1, BH2, and/or BH3, and that promote cell death by activating apoptosis. The "pro-apoptotic polypeptides" further include those proteins, or their biologically active fragments, that are at least 30%, 40%, 50%, 60%, 70%, 80%, 90%, 95%, 96%, 97%, 98%, 99% or more similar in amino acid sequence to a pro-apoptotic BCL-2 homology domain within a BCL-2 family polypeptide. Pro-apoptotic polypeptides can be identified as having one or more conserved amino acid residue, such as amino acid residues corresponding to Leu 92, Gly 96 and Asp 97 of BIM (SEQ ID NO: 2) or Leu 63, Ala 67 and Asp 68 of BIM (SEQ ID NO:1). Pro-apoptotic polypeptides include BAX, BAK, BOK/MTD, BID BAD, BIK/NBK, BLK HRK BIM/BOD, BNIP3, NIX, NOXA, PUMA, BMF AND EGL-1.

As used herein, the term "apoptosis" refers to a regulated network of biochemical events which lead to a selective form of cell death that is characterized by readily observable morphological and biochemical changes, such as the fragmentation of the deoxyribo-nucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient.

The term "compound" is used herein to denote a chemical agent, polypeptide or combination thereof, or a mixture of chemical compounds and/or polypeptides and/or nucleic acids (e.g. DNA and/or RNA derivative), salts and solvates thereof, and the like. Preferably, a compound of the invention binds to the active site of a BCL-2 family polypeptide. A "modulator" is a compound which modulates the activity of a BCL-2 family polypeptide.

The term "candidate compound" is used herein to denote a chemical compound, polypeptide or combination thereof, or a mixture of chemical compounds and/or polypeptides and/or nucleic acids, salts and solvates thereof, and the like, which is tested by a method of the invention and is found to bind to active site of a BCL-2 family polypeptide, and thus is believed to modulate the activity of the BCL-2 family polypeptide.

The term "modulate" as used herein with reference to a compound refers to the activation or inhibition of anti-apoptotic or pro-apoptotic activity of a BCL-2 family polypeptide or other protein-protein interaction involving a BCL-2 family member that regulates a biochemical pathway (e.g. unfolded protein response, glucose-stimulated insulin secretion). Methods for assaying both anti-apoptotic, pro-apoptotic, and other biochemical activities (e.g. unfolded protein response, glucose-stimulated insulin secretion) are well known in the art and described herein.

As used herein, the term "interacts" or "binds" refers to a condition of proximity between a compound, or portions thereof, and the active site of a BCL-2 family polypeptide or portions thereof. The interaction is between one or more moieties on the compound and one or more moieties on amino acids of the active site. The association may be non-covalent—wherein the juxtaposition is energetically favored by hydrogen bonding or van der Waals or electrostatic interactions—or it may be covalent. For example, hydrophobic amino acid residues including Ile 148, Ala 149, Leu 152, Ile 155, Gly 156, Ala 161 of BIM SAHB bind to or interact with a hydrophobic groove comprised of hydrophobic amino acids including Met 20, Ala 24, Leu 25, Gly 138, Trp 139, Leu 141 and Met 137 of BAX. Similarly, charged amino acid residues such as Arg 153, Arg 154, Asp 157, and Glu 158 of BIM SAHB bind to or interact with charged amino acid residues including Glu 131, Asp 142, Arg 134, and Lys 21 of BAX. Hydrophilic BIM SAHB residues such as N160 bind to or interact with hydrophilic BAX residues including Gln 32.

The term, "activates" refers to an increase in the anti-apoptotic or pro-apoptotic activity of a BCL-2 family polypeptide or other defined biochemical activity based upon protein-protein interaction. A compound that activates a pro-apoptotic activity will bind to an active site of a BCL-2 family polypeptide and cause a 2×, 3×, 4×, 5×, 6×, 7×, 8×, 9×, 10×, 15×, 20× or more increase in the pro-apoptotic activity of the BCL-2 family polypeptide when compared with a control lacking the compound. In another embodiment, a compound that activates an anti-apoptotic activity will bind to an active site of a BCL-2 family polypeptide and cause a 2×, 3×, 4×, 5×, 6×, 7×, 8×, 9×, 10×, 15×, 20× or more increase in the anti-apoptotic (survival) activity of the BCL-2 family polypeptide when compared with a control lacking the compound. Assays for assessing the activation of an anti-apoptotic or pro-apoptotic activity are known in the art and described herein.

The term, "inhibits" refers to a decrease or blocking of the anti-apoptotic or pro-apoptotic activity of a BCL-2 family polypeptide, or other defined biochemical activity based upon protein-protein interaction. For example, a compound that inhibits a pro-apoptotic activity will bind to an active site of a BCL-2 family polypeptide and prevent activation or reduce the activity of the BCL-2 family polypeptide. Thus, the compound will inhibit or decrease the effects of a pro-apoptotic activity. Thus, pro-apoptotic activity, e.g., cell death, will be less than 75%, 70%, 60%, 50%, 40%, 30%, 20%, 10%, 5% or less in a population of cells in which an inhibitor is present than compared to a control cell population where the compound is not present.

A compound that inhibits an anti-apoptotic activity will bind to an active site of a BCL-2 family polypeptide and prevent or inhibit anti-apoptotic activity. Thus, anti-apoptotic activity, e.g., cell survival, will be less than 75%, 70%, 60%, 50%, 40%, 30%, 20%, 10%, 5% or less in a population of cells in which the inhibitor is present than compared to a control cell population where the compound is not present.

Figure 2:
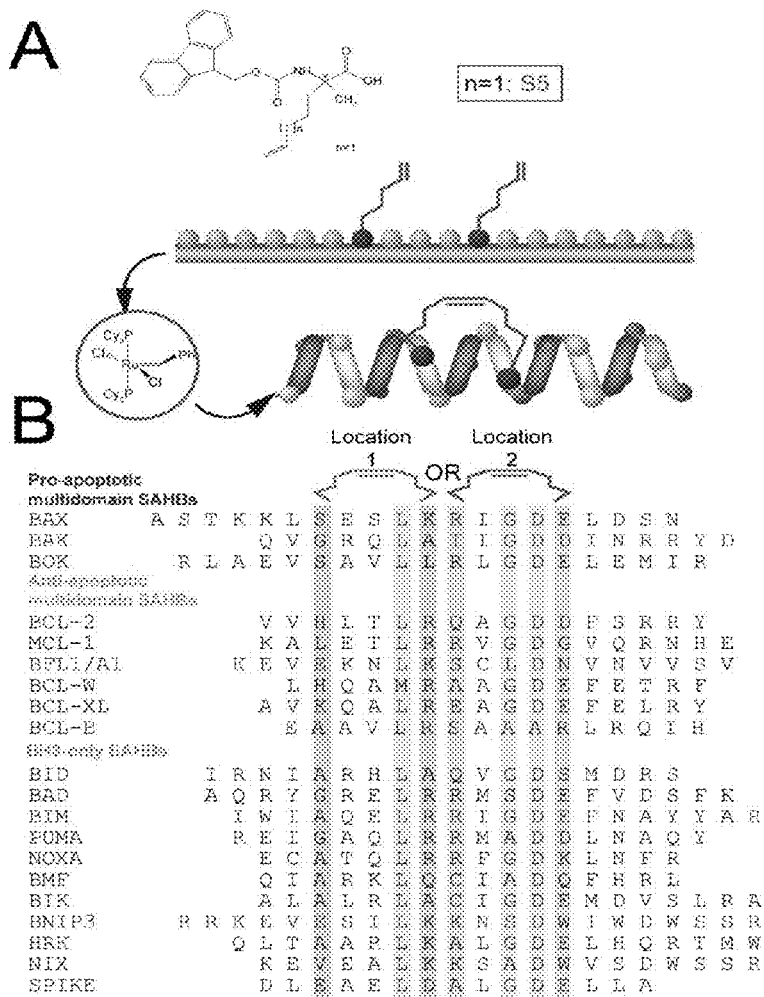
FIG. 2 illustrates the amino acid sequence and alignment of the BH3 domains of numerous BCL-2 family polypeptides (SEQ ID NOs: 15-34, respectively in order of appearance).

As used herein, the term "BH3 SAHB" refers to the BCL-2 homology domain 3 of a BCL-2 family polypeptide that has been hydrocarbon stapled so as to form a stabilized alpha helix. The amino acid sequence of numerous BH3 domains as described herein, (e.g., FIG. 2). Methods of making BH3 SAHB's are known in the art and described in U.S. Patent Publication No. US2005/0250680, filed Nov. 5, 2004, which is herein incorporated by reference in its entirety.

As used herein, the term "BIM BH3 polypeptide" refers to a polypeptide having a BCL-2 homology domain 3 of BIM. In one embodiment, the BIM BH3 polypeptide has an amino acid sequence which is 30%, 40%, 50%, 60%, 70%, 80%, 90%, 95%, 96%, 97%, 98%, 99% or more identical to SEQ ID NO: 3 and/or represented in FIG. 8 and may include one or more of amino acid residues corresponding to Leu 92, Gly 96 and Asp 97 of SEQ ID NO:2 or Leu152, Gly156, and Asp 157 of SEQ ID NO:9 or conservative substitutions thereof. In a preferred embodiment, the BIM BH3 polypeptide has the amino acid sequence of SEQ ID NO:3.

As used herein, the term "BID BH3 polypeptide" refers to a polypeptide having a BCL-2 homology domain 3 of BID. In one embodiment, the BID BH3 polypeptide has an amino acid sequence which is 30%, 40%, 50%, 60%, 70%, 80%, 90%, 95%, 96%, 97%, 98%, 99% or more identical to SEQ ID NO: 4 and/or represented in FIG. 9 and may include one or more of amino acid residues corresponding to Leu 90, Gly 94 and Asp 95 of SEQ ID NO:6 or conservative substitutions thereof. In a preferred embodiment, the BID BH3 polypeptide has the amino acid sequence of SEQ ID NO:4.

As used herein, the term "PUMA BH3 polypeptide" refers to a polypeptide having a BCL-2 homology domain 3 of PUMA. In one embodiment the PUMA BH3 polypeptide has an amino acid sequence which is 30%, 40%, 50%, 60%, 70%, 80%, 90%, 95%, 96%, 97%, 98%, 99% or more identical to SEQ ID NO: 5 and/or represented in FIG. 10 and may include one or more of amino acid residues corresponding to Leu 141, Ala 145 and Asp 146 of SEQ ID NO:7 or conservative substitutions thereof. In a preferred embodiment, the PUMA BH3 polypeptide has the amino acid sequence of SEQ ID NO:5.

As used herein, the term "BAX BH3 polypeptide" refers to a polypeptide having a BCL-2 homology domain 3 of BAX. In one embodiment, the BAX BH3 polypeptide has an amino acid sequence which is 30%, 40%, 50%, 60%, 70%, 80%, 90%, 95%, 96%, 97%, 98%, 99% or more identical to SEQ ID NO: 12 or as represented in FIG. 16a and may include one or more of amino acid residues corresponding to Leu 63, Ala 67 and Asp 68 of SEQ ID NO:1 or conservative substitutions thereof. In a preferred embodiment, a BAX BH3 polypeptide has the amino acid sequence of SEQ ID NO:12.

As used herein, the term "BH3 consensus sequence" refers to a polypeptide having the amino acid consensus sequence, or conservative substitutions thereof, of SEQ ID NO:13 and as represented in FIG. 20b. Generally, a BH3 polypeptide will have the amino acid consensus sequence of SEQ ID NO:13 and be at least 30%, 40%, 50%, 60%, 70%, 80%, 90%, 95%, 96%, 97%, 98%, 99% or more identical to a BIM, PUMA, BAX BH3 amino acid sequence. In a preferred embodiment, a BH3 polypeptide comprises the amino acid sequence of SEQ ID No:13. In a further preferred embodiment, the BH3 polypeptide is hydrocarbon stapled so as to form an alpha helix configuration.

As used herein, the term "BAX α-helix 9 polypeptide" refers to a polypeptide having a helix 9 of BAX. In one embodiment, the BAX α-helix 9 polypeptide has an amino acid sequence which is 30%, 40%, 50%, 60%, 70%, 80%, 90%, 95%, 96%, 97%, 98%, 99% or more identical to an amino acid sequence as represented in FIG. 16b.

The terms "pharmacologically effective amount," "therapeutically effective amount", "pharmacologically effective dose" or simply "effective amount" refers to that amount of an agent effective to produce the intended pharmacological, therapeutic or preventive result. The pharmacologically effective amount results in the amelioration of one or more symptoms of a disorder, or prevents the advancement of a disorder, or causes the regression of the disorder. For example, with respect to the treatment of a disorder or excessive cellular survival or proliferation, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

For example, with respect to the treatment of a disorder associated with increased cellular death, e.g., ischemia, a therapeutically effective amount preferably refers to the amount of a therapeutic agent that prevents or limits tissue and/or cellular damage that would otherwise occur if treatment was not administered. The therapeutic agent decreases tissue and/or cellular damage by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to damage that occurs without the administration of a therapeutic agent of the invention.

The terms "treat," and "treating," as used herein with reference to a disorder (e.g., hyperpoliferative disorder, excessive cellular survival or proliferation), refers to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention. In some embodiments, such terms refer to one, two, three or more results following the administration of one or more therapies: (1) a stabilization, reduction or elimination of the cancer cell population, (2) an increase in the length of remission, (3) a decrease in the recurrence rate of cancer, (4) an increase in the time to recurrence of cancer, and (6) an increase in the survival of the patient.

The terms "treat," and "treating," as used herein with reference to a disorder associated with increased cellular death, e.g., ischemia, refer to a decrease in the occurrence of tissue and/or cellular damage in an animal. The prevention may be complete, e.g., the total absence of tissue damage in a subject. The prevention may also be partial, such that the occurrence of tissue damage in a subject is less than that which would have occurred without the therapeutic agent.

As used herein, a "BCL-2 associated disorder", refers to a disorder associated with a deregulated BCL-2 family member. BCL-2 associated disorders are associated with excessive cellular survival and/or proliferation, e.g., cancer, or excessive cellular death, e.g., Alzheimer's disease. BCL-2 associated disorders include those described herein.

As used herein, a "hyperproliferative disorder" means cancer, neoplastic growth, hyperplastic or proliferative growth or a pathological state of abnormal cellular development or survival and includes solid tumors, non-solid tumors, and any abnormal cellular proliferation or accumulation, such as that seen in leukemia.

The terms "anticancer agent" and "anticancer drug," as used herein, refer to any therapeutic agents (e.g., chemotherapeutic compounds and/or molecular therapeutic compounds), antisense therapies, nucleic acid therapies (e.g. RNAi), radiation therapies, used in the treatment of hyperproliferative diseases such as cancer. In one embodiment, the invention is directed to methods of treating a BCL-2 associated disorder comprising administering an effective dose of an anticancer agent and a compound which binds to the active site, as described herein, of a BCL-2 family peptide.

As used herein, the term "structural coordinates" refers to Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. Structural coordinates for the BCL-2 family members are known in the art and publicly available.

The term "interaction template" refers to a three dimensional model built using Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of BCL-2 family polypeptides are known in the art and can be found for example at Protein Data Bank ("PDB") (Research Collaboratory for Structural Bioinformatics; http://www.rcsb.org). For example, known BCL-2 family structural co-ordinates include BAX (PDB ID No. 1f16), BAK (PDB ID No. 2ims), BCL-2 (PDB ID No. 1g5m), BIM (PDB ID No. 2pqk) and BCL-XL (PDB ID No. 1lxl), in addition to those associated with this invention: BIM BH3-BAX (PDB ID No. 2k7w), as well as others known in the art.

Preferably, the interaction template is of a BAX polypeptide having the amino acids sequence set forth in SEQ ID NO:1, wherein the active site of the BAX polypeptide is accessible to solvent and available for interaction with modulators, e.g., activators. This three-dimensional form of BAX is used to facilitate the identification of compounds which bind in the active site. As used herein, the "interaction template" includes templates created by comparing the sequence/structual alignment of BAX to other BCL-2 family polypeptides. Identification of conserved and non-conserved residues allows a skilled artisan to identify a corresponding active site in other BCL-2 family polypeptides and design/screen modulators of the polypeptide.

As used herein in relation to the position of an amino acid, e.g., Ala 149 of SEQ ID NO:1, the term "corresponding to" refers to an amino acid in a first polypeptide sequence, e.g., BAX, that aligns with a given amino acid in a reference polypeptide sequence, e.g., BAK, when the first polypeptide and reference polypeptide sequences are aligned by homology or other algorithms (e.g., structural comparison). For example, Leu 92 of SEQ ID NO:2 corresponds to Leu 90 of SEQ ID NO:6 and Leu 141 of SEQ ID NO:7. Similarly Gly 96 of SEQ ID NO:2 corresponds to Gly 94 of SEQ ID NO:6 and Ala 145 of SEQ ID NO:7. Alignment is performed by one of skill in the art using software designed for this purpose, for example, BLASTP version 2.2.2 with the default parameters for that version. Corresponding amino acids can also be identified upon structural comparisons of a first polypeptide sequence and a second polypeptide sequence. Such structural comparisons are known in the art and described herein. For example, Petros et al. Biochimica et Biophysica Acta 1644; 83-94 (2004) and Suzuki et al., Cell. 103; 645-654 (2000) illustrated structural alignments between BCL-2 homology domains of BCL-2 family members.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes.

A "non-essential" amino acid residue is a residue that can be altered from the wild-type sequence of a polypeptide (e.g., BIM BH3) without abolishing or substantially altering its BAX binding ability. An "essential" amino acid residue is a residue that, when altered from the wild-type sequence of the polypeptide, results in abolishing or substantially abolishing the polypeptide's binding activity to a BAX active site. The essential and non-essential amino acid residues of the BH3 domains can readily be determined by methods well known in the art and described herein. The term "essential" amino acid residue as used herein, includes conservative substitutions of the essential amino acid. Generally, the "essential" amino acid residues are found at the interacting face (residues interacting with BAX) of the BH3 polypeptide.

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted nonessential amino acid residue in a BH3 domain polypeptide, for example, is preferably replaced with another amino acid residue from the same side chain family or homologues across families (e.g. asparagines for aspartic acid, glutamine for glutamic acid). In addition, individual substitutions, deletions or additions that alter, add or delete a single amino acid or a small percentage of amino acids in an encoded sequence are also considered "conservative substitutions.

The terms "identical" or "percent identity," in the context of two or more nucleic acids or polypeptide sequences, refer to two or more sequences or subsequences that are the same or have a specified percentage of nucleotides or amino acids that are the same, when compared and aligned for maximum correspondence, as measured using one of the following sequence comparison algorithms, or by visual inspection.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first protein region can be considered similar to a region of an anti-apoptotic BCL-2 family member protein when the amino acid sequence of the first region is at least 40%, 50%, 60%, 70%, 75%, 80%, 90%, or even 95% identical, or conservatively substituted, to a region of the second anti-apoptotic BCL-2 family member protein when compared to any sequence of an equal number of amino acids as the number contained in the first region, or when compared to an alignment of anti-apoptotic BCL-2 family member proteins that has been aligned by a computer similarity program known in the art, as discussed below. Preferably, the polypeptide region of the first protein and the second protein includes one or more conserved amino acid residues, e.g., such as those illustrated in FIG. 2.

II. Description

The present invention is directed to methods, kits and compositions for modulating the activity of BCL-2 family polypeptides (e.g., BAX) by targeting a new regulatory site on BCL-2 family proteins. The methods and compounds of the invention are useful for treating and/or preventing disorders (e.g., hyperpoliferative disorders) characterized by the deregulation of one or more polypeptides of the BCL-2 family. Further, the methods and compounds of the present invention are also useful in the treatment of non-BCL-2 related disorder associated with excessive cellular proliferation or survival, or excessive cellular death (e.g., apoptosis). The present invention is based, at least in part, on the identification of an active site on a BAX polypeptide, which when bound by a compound, modifies the apoptotic activity of the BAX polypeptide. At least in part, the identity and location of this active site was revealed by the specific binding activity of hydrocarbon-stapled activator BH3 peptides to the active site. Whereas blockade of this active site represses BAX-induced cell death, ligand engagement triggers BAX-mediated apoptosis.

In a first aspect, the invention is directed to a method for identifying a compound that modulates the activity of a BCL-2 family polypeptide. The method includes contacting a BCL-2 family polypeptide with a compound that binds to the active site in the polypeptide and detecting a modulated activity of the polypeptide, thereby identifying a BCL-2 family polypeptide modulator.

Any BCL-2 family polypeptide having an active site corresponding to the BAX active site, as described herein, is useful in practicing the invention. Non-BAX BCL-2 family polypeptide active sites corresponding to the BAX active site can be identified by amino acid sequence alignments between BAX and the test molecule, by structural comparison, or by a combination thereof. Such methods are known by those having ordinary skill in the art and are described herein. The BCL-2 family polypeptide can be either a pro-apoptotic or anti-apoptotic BCL-2 family member. Suitable pro-apoptotic polypeptides include, but are not limited to BAX, BOK and BAK. Suitable anti-apoptotic polypeptides include, but are not limited to BCL-2, Bcl-Xl, Bcl-w, Mcl-1, BCL-B, A1/BFL-1, BOO/DIVA, Nr-13 or CED-9, and viral homologues. The method may be performed in a cell or in a cell-free system. When performed in a cell, the BCL-2 family polypeptide may be encoded by an endogenous nucleic acid or by a nucleic acid which is exogenously added to the cell (e.g., transfected).

The active site of the BCL-2 family polypeptide is an interface which is capable of binding a BIM BH3, BID BH3, PUMA BH3, BAX BH3, or other stabilized alpha helix of BCL-2 domains (i.e. SAHB) and is formed by the juxtaposition of alpha helices 1 and 6 of BAX. The active site includes a hydrophobic patch and a perimeter of charged amino acids. In a preferred embodiment, the active site includes amino acids corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1.

The compound that modulates the BCL-2 family polypeptide can be an organic compound or a polypeptide, or combination thereof, which binds the active site of the polypeptide. Preferably, the compound binds to one, two, three, four, five, six or more amino acid residues of the active site corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1, or other neighboring residues. Other neighboring residues that change confirmation upon binding to the active site include amino acid residues corresponding to 6, 7, 9, 14, 18, 21, 23, 26, 34-35, 36, 40-42, 44-46, 57, 63, 71, 83-86, 108, 118, 121, 126, 132, 136, and 144 of SEQ ID NO:1. In one embodiment, the compound is a BH3 region polypeptide. Suitable BH3 region polypeptides can be derived from any BCL-2 polypeptide that contain a BH3 region (e.g., FIGS. 1 and 2). For example, suitable BH3 region polypeptides can be derived from Bim, Bid, Bad, Bik/Nbk, Blk, Hrk, Bim/Bod, Bnip3, Nix, Noxa, Puma, Bmf or Egl-1, or any other BCL-2 polypeptide that contains a BH3 domain. In one embodiment, the compound is a BH3 region polypeptide having an amino acid sequence which is 95% identical with SEQ ID NO:3 and has an amino acid residue corresponding to Arg 153 of SEQ ID NO:9, or a conservative substitution thereof. In yet a further embodiment, the compound has amino acid residues corresponding to Ile148, Ala149, L152, Arg153, Arg154, Ile155, Gly156, Asp157, Glu158, Asn160, Ala161, Tyr163 of SEQ ID NO:9. In a preferred embodiment, the suitable BH3 region polypeptide is derived from the pro-apoptotic protein BIM (SEQ ID NO: 2, SEQ ID NO:9) or BID (SEQ ID NO: 6) or PUMA (SEQ ID NO: 7, SEQ ID NO: 10) or BAX (SEQ ID NO:1). In an even more preferred embodiment, the compound is a BIM BH3 SAHB polypeptide (FIG. 8, and SEQ ID NO:3), a BID BH3 SAHB polypeptide (FIG. 9, and SEQ ID NO:4), a PUMA BH3 SAHB polypeptide (FIG. 10 and SEQ ID NO:5), or a BAX BH3 SAHB (FIG. 16 and SEQ ID NO:12). The BIM BH3 SAHB polypeptide is hydrocarbon stapled so as to have a stabilized alpha-helical structure. Methods of making BH3 SAHBs are known in the art and described in U.S. Patent Publication No. US2005/0250680, filed Nov. 5, 2004, which is herein incorporated by reference in its entirety.

This aspect of the invention involves detecting a change (e.g., modulation) in the activity of the BCL-2 family polypeptide. BCL-2 family polypeptides generally have either pro-apoptotic or anti-apoptotic activity, yet can also participate in protein interactions of other biochemical pathways of physiologic significance (Danial, N. N., et al. *Nature* 424(6951), 952-956 (2003)., Zinkel, S. S., et al. *Cell* 122(4), 579-591 (2005)). In one embodiment, the modulation is directed to a pro-apoptotic activity. The pro-apoptotic modulation can be either activation (e.g., increase in apoptosis, cell death) or inhibition (e.g., decrease in apoptosis, cell survival).

In another embodiment, the modulation is directed to anti-apoptotic activity. The anti-apoptotic modulation can be either activation (e.g., increase in cell survival, decrease in apoptosis) or inhibition (e.g., increase in apoptosis, cell death). The modulated activity can be detected by various methods known in the art and described herein, including, but not limited to, dimerization, oligomerization or change in conformational state, translocation from one cellular compartment to another, mitochondrial cytochrome c release, cell death, mitochondrial morphology, mitochondrial calcium uptake, mitochondrial transmembrane quantitation, and quantitation of caspase 3 activity or annexin V binding.

In a further aspect, the invention is directed to a method for identifying a compound which activates or inhibits the apoptotic activity of a BAX polypeptide. The method includes contacting the BAX polypeptide with a compound which activates or inhibits BAX when bound to one or more amino acid residues Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg 147 of a BAX active site, and detecting activation or inhibition of the pro-apoptotic activity of BAX, thereby identifying a BAX modulator.

In yet another aspect, the invention is directed to a method for identifying a candidate modulator of a BCL-2 family polypeptide. The method entail using a three dimensional structure (e.g., interaction template) of an active site of the BCL-2 family polypeptide, and employing the three dimensional structure to select a BCL-2 family polypeptide candidate modulator from a group of compounds. A compound is identified as a candidate modulator when it binds to the active site described herein of the BCL-2 family polypeptide.

Any BCL-2 family polypeptide having an active site corresponding to the BAX active site, as described herein, is useful in practicing this aspect of the invention. Non-BAX BCL-2 family polypeptide active sites corresponding to the BAX active site can be identified by amino acid sequence alignments between BAX and the test molecule, by structural comparison or by a combination thereof. Such methods are known by those having ordinary skill in the art and are described herein. The BCL-2 family polypeptide can be either a pro-apoptotic or anti-apoptotic BCL-2 family member. Suitable pro-apoptotic polypeptides include, but are not limited to BAX, BOK and BAK. Suitable anti-apoptotic polypeptides include, but are not limited to, BCL-2, Bcl-Xl, Bcl-w, Mcl-1, BCL-B, A1/BFL-1, BOO/DIVA, Nr-13 or CED-9, and viral homologues.

In one embodiment, the three dimensional structure is of a full length BCL-2 family polypeptide. In another embodiment, the three dimensional structure is of a fragment of the BCL-2 family polypeptide having the active site. The active site of the BCL-2 family polypeptide includes a central hydrophobic surface surrounded by a perimeter of charged and hydrophilic residues and is capable of binding the BIM BH3, BID BH3, PUMA BH3, BAX BH3, or other stabilized alpha helix of BCL-2 domain and is formed by the juxtaposition of alpha helices 1 and 6 of BAX. The active site has both a hydrophobic patch and a perimeter of charged and hydrophilic amino acids. In a preferred embodiment, the active site includes, but is not limited to, amino acids corresponding to Met20, Lys21, Ala24, Leu 27, Gln28, Gln32, Glu131, Arg134, Thr135 Met137, Gly138, Leu141, Asp142 of SEQ ID NO:1. In another embodiment, the active site includes amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1

The candidate modulator can be any organic compound or a polypeptide, or combination thereof, which binds the active site of the polypeptide. Preferably, the candidate modulator binds to one or more amino acid residues of the active site corresponding to Met20, Lys21, Ala24, Leu 27, Gln28, Gln32, Glu131, Arg134, Thr135 Met137, Gly138, Leu141, Asp142 of SEQ ID NO:1. In another embodiment, the candidate modulator binds to one or more amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1. In one embodiment, the candidate modulator is a BH3 region polypeptide. Suitable BH3 region polypeptides can be derived from any BCL-2 polypeptide that expresses a BH3 region (e.g., FIG. 1 or 2). For example, suitable BH3 region polypeptides can be derived from Bid, Bad, Bik/Nbk, Blk, Hrk, Bim/Bod, Bnip3, Nix, Noxa, Puma, Bmf or Egl-1, or any other BCL-2 family polypeptide that contains a BH3 domain. In some embodiments the polypeptide comprises at least 5, 6, 7, 8, 9, 10, 11, 12, 13, 14, 15, 16, 17, 18, 19, 20, 25, 50, or more contiguous amino acids of a BH3 domain selected from a group consisting of those illustrated in FIG. 1, 2, 8, 9, 10, 16a, or 20. In one embodiment, the compound is a BH3 region polypeptide having an amino acid sequence which is 95% identical with SEQ ID NO:3 or BH3 regions exemplified in FIG. 1, 2, 8, 9, 10, 16a, or 20 and has an amino acid residue corresponding to Leu152 and Asp157 of SEQ ID NO:9, or conservative substitution thereof. In yet a further embodiment, the candidate modulator has amino acid residues corresponding to Ile148, L152, Arg153, Arg154, Ile155, Gly156, Asp157, Glu158, Asn160, Ala161, Tyr163 of SEQ ID NO:9. In a preferred embodiment, the suitable BH3 region polypeptide is derived from the pro-apoptotic protein BIM (SEQ ID NO: 2, SEQ ID NO: 9) or BID (SEQ ID NO: 6), PUMA (SEQ ID NO: 7, SEQ ID NO: 10). In an even more preferred embodiment, the compound is a BIM BH3 SAHB polypeptide (SEQ ID NO:3), a BID BH3 SAHB polypeptide (SEQ ID NO:4) or a PUMA BH3 SAHB polypeptide (SEQ ID NO:5) or a BAX BH3 SAHB (SEQ ID NO:12). The BH3 SAHB polypeptide is hydrocarbon stapled so as to have a stabilized alpha-helical structure. Methods of making BH3 SAHBs are known in the art and described in U.S. Patent Publication No. US2005/0250680, filed Nov. 5, 2004, which is herein incorporated by reference in its entirety.

In a further embodiment of this aspect, the candidate compound can be tested in a biological assay to determine whether the candidate compound does in fact modulate the BCL-2 family member. Suitable biological assays are known in the art and described herein, including, but not limited to, detection of dimerization, oligomerization or change in conformational state, or translocation from one cellular compartment to another, mitochondrial cytochrome c release, cell death, mitochondrial morphology, mitochondrial calcium uptake, mitochondrial transmembrane quantitation, and quantitation of caspase 3 activity or annexin V binding.

In a further aspect, the invention is directed to a method for identifying a candidate compound that modulates (e.g., activates) the apoptotic activity of a BAX polypeptide. The method includes: providing a three dimensional structure of an active site of the BAX polypeptide, simulating a binding interaction between the active site and a compound; and determining whether the compound binds to one or more amino acid residues comprising, but not limited to, Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1 of the active site. A compound is identified as a candidate compound when it capable of binding to one or more of the amino acid residues of the active site.

In yet another aspect, the present invention is directed to a method for treating or preventing a BCL-2 related disorder in an individual. The method involves administering to an individual in need thereof, a pharmacologically effective dose of a compound identified by any of the above aspects.

In yet another aspect, the present invention is directed to a method for treating or preventing a BCL-2 related disorder in an individual. The method involves administering to an individual in need thereof, a pharmacologically effective dose of a compound that binds to an active site of the BCL-2 family polypeptide.

A BCL-2 related disorder is any disorder attributed to a deregulation in one or more BCL-2 family polypeptides. BCL-2 related disorders include cellular proliferation or apoptotic blockage disorders such as cancer and autoimmune disease. Examples of BCL-2 related cancers include, but are not limited to, solid tumors, leukemias, and lymphomas. In one embodiment, the disorder is a chemoresistant cancer. In a more preferred embodiment, the chemoresistant cancer is resistant to ABT-737 or ABT-263 (available from Abbott; Abbott Park, Ill.).

Figure 4A:
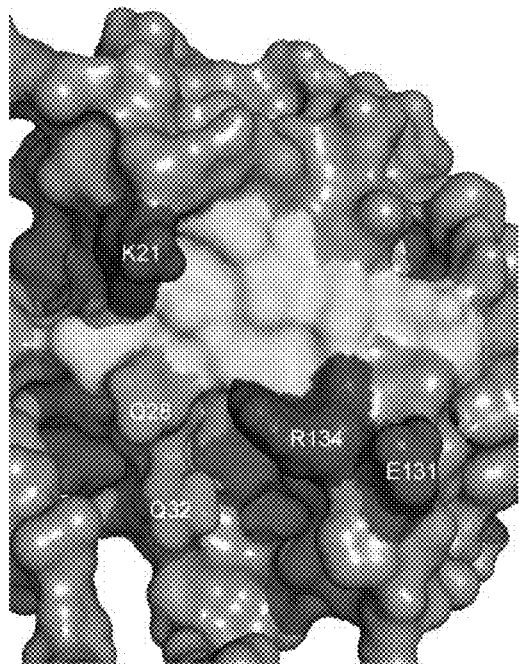
FIG. 4 (a) Surface diagram illustrating the BAX binding site. Solvent exposed residues at the binding site are indicated. Yellow shading designates the sidechains of the hydrophobic residues M20, A24, L27, I31, I133, M137, and L141. Red and blue shading designate the sidechains of positively (K21, R134) and the negatively charged residue (E131) respectively. Green shading designates sidechains of the hydrophilic residues (Q28, Q32). (b) NMR analysis of the BIM SAHB-BAX interaction demonstrates a new binding site for BH3-mediated BAX activation. BIM SAHB engages BAX at a structural location that is distinct from the canonical BH3 binding site identified for anti-apoptotic proteins.

The active site of the BCL-2 family polypeptide is a surface that contains a core of hydrophobic residues surrounded by several charged and hydrophilic amino acids and is capable of binding a BIM BH3 stabilized alpha helix of BCL-2 domain (i.e. BIM SAHB) and is formed by the juxtaposition of alpha helices 1 and 6 of BAX (FIG. 4). The active site has both a hydrophobic patch and a perimeter of charged and hydrophilic amino acid residues. In a preferred embodiment, the active site has one or more amino acids corresponding to Met20, Lys21, Ala24, Leu 27, Gln28, Gln32, Glu131, Arg134, Thr135 Met137, Gly138, Leu141, Asp142 of SEQ ID NO:1. In another embodiment, the active site includes amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1

The active site can be on any BCL-2 family polypeptide having an active site corresponding to the BAX active site, described herein. Non-BAX BCL-2 family polypeptide active sites corresponding to the BAX active site can be identified by amino acid sequence alignments between BAX and the test molecule, by structural comparison or by a combination thereof. Such methods are known by those having ordinary skill in the art and are described herein. The BCL-2 family polypeptide can be either a pro-apoptotic or anti-apoptotic member of the BCL-2 family. Suitable pro-apoptotic polypeptides include, but are not limited to, BAX, BOK and BAK. Suitable anti-apoptotic polypeptides include, but are not limited to, BCL-2, Bcl-Xl, Bcl-w, Mcl-1, BCL-B, A1/BFL-1, BOO/DIVA, Nr-13 or CED-9, and viral homologues.

The compound that modulates the BCL-2 family polypeptide can be any organic compound, polypeptide or combination thereof, or a mixture of chemical compounds and/or polypeptides and/or nucleic acids (e.g. DNA and/or RNA derivative), salts and solvates thereof, and the like which binds the active site of the protein. Preferably, the compound binds to one or more amino acid residues of the active site. In a more preferred embodiment, the active site includes amino acid residues corresponding to of Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1. In one embodiment, the compound is a BH3 region polypeptide (e.g., FIG. 1, 2). Suitable BH3 region polypeptides can be derived from a BCL-2 polypeptide that contain a BH3 region. For example, suitable BH3 region polypeptides can be derived from Bim, Bid, Bad, Bik/Nbk, Blk, Hrk, Bim/Bod, Bnip3, Nix, Noxa, Puma, Bmf or Egl-1, or any other BCL-2 family polypeptide that contains a BH3 domain. In some embodiments the BH3 domain polypeptide comprises at least 5, 6, 7, 8, 9, 10, 11, 12, 13, 14, 15, 16, 17, 18, 19, 20, 25, 50, or more contiguous amino acids of a BH3 domain selected from, but not limited to, the group consisting of those illustrated in FIG. 1, 2, 8, 9, 10, 16a, or 20). In one embodiment, the compound is a BH3 region polypeptide having an amino acid sequence which is 95% identical with SEQ ID NO:3 or as illustrated in FIG. 1, 2, 8, 9, 10, 16a, or 20, and has an amino acid residue corresponding to Leu152 and Asp157 of SEQ ID NO:9, or a conservative substitution thereof. In yet a further embodiment, the compound has amino acid residues corresponding to Ile148, Ala149, L152, Arg153, Arg154, Ile155, Gly156, Asp157, Glu158, Asn160, Ala161, Tyr163 of SEQ ID NO:9. In a preferred embodiment, the suitable BH3 region polypeptide is derived from the pro-apoptotic protein BIM (SEQ ID NO: 2, SEQ ID NO: 9) or BID (SEQ ID NO: 6) or PUMA (SEQ ID NO:7, SEQ ID NO:10). In an even more preferred embodiment, the compound is a BIM BH3 SAHB polypeptide (SEQ ID NO:3), a BID BH3 SAHB polypeptide (SEQ ID NO:4), a PUMA BH3 SAHB polypeptide (SEQ ID NO:5) or a BAX BH3 SAHB (SEQ ID NO:12). The BIM BH3 SAHB polypeptide is hydrocarbon stapled so as to have a stabilized alpha-helical structure. Methods of making BH3 SAHB's are known in the art and described in U.S. Patent Publication No. US2005/0250680, filed Nov. 5, 2004, which is herein incorporated by reference in its entirety.

Binding of the compound to the active site of the BCL-2 polypeptide results in the modulation of a BCL-2 activity (e.g., pro- or anti-apoptotic activity). In one embodiment, the modulation is either activation (e.g., increase in apoptosis, cell death) or inhibition (e.g., decrease in apoptosis, cell survival) of pro-apoptotic activity. In another embodiment, the modulation is either activation (e.g., increase in cell survival, decrease in apoptosis) or inhibition (e.g., increase in apoptosis, cell death) of anti-apoptotic activity.

In yet a further embodiment, the invention is directed to a method of treating or preventing a hyperpoliferative disorder (e.g., cancer, chemoresistant cancer) in an individual, by activating the pro-apoptotic activity of a BAX polypeptide. The method entails administering to an individual in need thereof a pharmacologically effective dose of a BH3 polypeptide which binds to one or more amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1 of the active site of BAX so as to activate the pro-apoptotic activity of the BAX polypeptide.

In another aspect, the invention is directed to a compound for treating or preventing a BCL-2 related disorder in an individual. The compound modulates the activity of a BCL-2 family polypeptide when bound to an active site of the BCL-2 family polypeptide.

In a further aspect, the invention is directed to a compound for treating or preventing a hyperpoliferative disorder (e.g., cancer, chemoresistant cancer) in an individual. The compound is a BH3 polypeptide that activates the pro-apoptotic activity of a BAX polypeptide when bound to amino acid residues corresponding to Met20, Lys21, Ala24, Leu 27, Gln28, Gln32, Glu131, Arg134, Thr135 Met137, Gly138, Leu141, Asp142 of SEQ ID NO:1. In another embodiment, the compound is a BH3 polypeptide that activates the pro-apoptotic activity of a BAX polypeptide when bound to amino acid residues corresponding to Glu17, Met20, Lys21, Thr22, Ala24, Leu25, Leu27, Gln28, Gly29, Ile31, Gln 32, Asp33, Leu47, Asp48, Pro49, Val50, Pro51, Gln52, Asp53, Thr56, Arg89, Phe92, Phe93, Pro130, Glu131, Ile 133, Arg 134, Thr135, Met137, Gly138, Trp139, Leu141, Asp142, Phe143, Arg145, Glu146, Arg147 of SEQ ID NO:1.

In another aspect, the invention is directed to a BH3 SAHB polypeptide that includes one or more paramagnetic labels (FIG. 6) and methods of use thereof. The invention provides for an expedient method to generate MTSL-derivatized SAHBs for paramagnetic relaxation enhancement (PRE) NMR experiments to identify the orientation and structural interaction details of SAHB binding to the active site of BAX or such an active site on other BCL-2 family polypeptide. The MTSL label is reacted with a cysteine residue that is substituted into the SAHB peptide, thereby incorporating the nitroxide spin label for PRE NMR experiments, conducted as known in the art. For example, the method includes incubating an MTSL-derivatized BH3 SAHB polypeptide with BAX, followed by PRE-based NMR analysis to determine the orientation of BIM SAHB at the BAX site (FIG. 6).

In another aspect, the invention is directed to a BH3 SAHB polypeptide that includes one or more crosslinkable moieties (FIGS. 11, 17, and 18) and methods of use thereof. The invention provides for a novel, alternative, and expedient method for identifying homologous active sites in non-BAX BCL-2 family and non-BCL-2 family members via direct covalent intercalation of photoactivatable and crosslinkable derivatives of BH3 peptides or their mimetics (e.g., FIGS. 11, 17, and 18) to the target site, followed by intercalation site identification by, for example, proteolysis, fragment purification, and mass spectrometry based analysis. For example, the method includes incubating a target polypeptide with a BH3 SAHB polypeptide comprising a covalent crosslinkable moiety, crosslinking the BH3 SAHB polypeptide to the target polypeptide, and identifying the intercalation site of the BH3 SAHB polypeptide to the target polypeptide.

In one embodiment, the crosslinkable moiety is a benzophenone. Suitable BH3 SAHB polypeptides include BIM, BID, PUMA, and BAX. The amino acid sequence and benzophenone location for numerous BH3 SAHB polypeptides is represented in FIG. 11.

In still another aspect, the invention is directed to kits containing any of the above compounds and instructions for use.

III. BCL-2 Family of Peptides

The BCL-2 family of proteins includes both pro- and anti-apoptotic polypeptides that provide the checks and balances that govern susceptibility to cell death (FIG. 1). Deregulation of this pathway has been documented in the pathogenesis of a wide spectrum of human diseases, including many cancers.

Members of the evolutionarily conserved BCL-2 family are important regulators of apoptotic cell death and survival. The proteins BCL-2, Bcl-xL, Bcl-w, Bfl1/A1, Bcl-B and Mcl-1 are death antagonists while Bax, Bak, Bad, Bcl-xs, Bid, Bim and Bik are death agonists (Kroemer et al., Nature Med. 6:614 20 (1997)).

The BCL-2 family is defined by the presence of up to four conserved "BCL-2 homology" (BH) domains designated BH1, BH2, BH3, and BH4, all of which include alpha-helical segments (Chittenden et al. 1995 EMBO 14:5589; Wang et al. 1996 Genes Dev. 10:2859) (FIG. 1). Anti-apoptotic proteins, such as BCL-2 and BCL-XL, display sequence conservation in all BH domains. Pro-apoptotic proteins are divided into "multidomain" members (e.g. BAK, BAX, BOK), which possess homology in the BH1, BH2, and BH3 domains, and the "BH3-domain only" members (e.g. BID, BAD, BIM, BIK, NOXA, PUMA), that contain sequence homology exclusively in the BH3 amphipathic alpha-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. In certain cell types, death signals received at the plasma membrane trigger apoptosis via a mitochondrial pathway. The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-XL and BAK/BAX play dueling roles of guardian and executioner at the mitochondrial membrane, with their activities further regulated by upstream BH3-only members of the BCL-2 family. For example, BID is a member of the "BH3-domain only" subset of pro-apoptotic proteins, and transmits death signals received at the plasma membrane to effector pro-apoptotic proteins at the mitochondrial membrane. Select BH3-only members, such as BID and BIM, have been termed "activators" (Letai, A., et al. *Cancer Cell* 2, 183-192 (2002)), and have the unique capability of interacting with both pro- and anti-apoptotic proteins (Walensky Mol Cell 2006). Upon caspase 8 activation, BID is cleaved and the truncated adduct, tBID, triggers cytochrome c release and mitochondrial apoptosis through engagement of BCL-2 family proteins.

Deletion and mutagenesis studies determined that the amphipathic alpha-helical BH3 segment of pro-apoptotic family members functions as a death domain and thus represents a critical structural motif for interacting with multidomain apoptotic proteins. Structural studies have demonstrated that the BH3 helix interacts with anti-apoptotic proteins by inserting into a hydrophobic groove formed by the interface of BH1, 2 and 3 domains. tBID and BIM can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program.

BCL-2-related ovarian killer (BOK) is the third member of the pro-apoptotic multidomain subgroup and is also bound by activator SAHB ligands, such as BID and BIM SAHBs. BOK was cloned from an ovarian cDNA library and found to be highly expressed in ovary, uterus, and testis. BOK mRNA species have since been identified in a broader distribution of tissues, including heart, spleen, liver, colon, lung, intestine, thyroid gland, adrenal, pancreas, and bone marrow, and select cancer cell lines.

The first X-ray and NMR structure of a BCL-2 family protein (BCL-$X_L$) was reported in 1996. BCL-$X_L$ consists of eight alpha-helices, two of which form a central hydrophobic core similar to the membrane insertion domains of pore-forming Diphtheria toxin and colicins. This structural analogy led to experimental confirmation that BCL-2 family members can mediate pore-formation in liposomal and mitochondrial systems, an activity that is dependent upon core helices 5 and 6.

On the pro-apoptotic side, NMR structures of BH3-only BID and multidomain pro-apoptotic BAX disclosed similarities between the proponents and opponents of cell death (FIG. 3, 7). BID and BAX likewise possess two central core helices that are surrounded by 6 or 7 amphipathic helices, respectively. The amino terminal portions of BID and BAX contain unstructured loops, as do select anti-apoptotic proteins such as BCL-2 and BCL-$X_L$.

The structures of many of the BCL-2 family polypeptides, including, BCL-$X_L$, BCL-2, BID, BAX, BCL-w, MCL-1, BAX are known in the art and readily accessible. For example, BCL-2 family polypeptides can be obtained from the Protein Data Bank ("PDB") (Research Collaboratory for Structural Bioinformatics; http://www.rcsb.org). For example, known BCL-2 family structural co-ordinates include BAX (PDB ID No. 1f16), BAK (PDB ID No. 2ims), BCL-2 (PDB ID No. 1g5m), BCL-XL (PDB ID No. 11x1), in addition to that associated with this invention: BIM BH3-BAX (PDB ID No. 2k7w), as well as others known in the art.

IV. BCL-2 Family Active Sites

The present invention is based, at least in part, on the discovery that hydrocarbon-stapled and thus structurally-reinforced "activator" BH3 polypeptides, such as BIM SAHB (FIG. 8), bind a novel active site on BAX polypeptides that results in activation of the pro-apoptotic activity of BAX. The present studies have provided structural information that has enabled identification of the region of the BAX polypeptide involved in the molecular interaction with BIM SAHB and thus activation of this polypeptide, thereby providing methods for identifying other specific modulators of BAX and any other BCL-2 family polypeptides (or other class of polypeptides) containing a corresponding active site.

NMR structural analysis of BIM BH3 SAHB co-complexed with BAX revealed an active site of BAX which is formed by the juxtaposition of BAX alpha helices 1 and 6 (FIGS. 3 and 4). The NMR data of the complexed BAX polypeptide with BIM SAHB (FIG. 6) shows the active site is comprised of both a hydrophobic patch and a perimeter of charged and hydrophilic residues which contribute to the binding of BIM BH3 and activation of BAX. The hydrophobic patch is comprised of, but not limited to, amino acid residues Ala 24, Met 20, Leu 25, Leu 27, Ile 31, Ile 133, Met 137, Gly 138, Trp 139, Leu 141, while the charged and hydrophilic regions are comprised of, but not limited to, Lys 21, Gln 28, Gln 32, Asp 33, Gln 52, Glu 17, Arg, 134, Thr 135, Asp 142, Arg 145, Arg 147 of SEQ ID NO:1. These hydrophobic amino acids in turn bind hydrophobic amino acid residues Ile 148, Ala 149, Leu 152, Ile 155, Gly 156, and Phe 159 of BIM SAHB and the charged and hydrophilic amino acid residues bind charged and hydrophilic amino acid residues Arg 153, Arg 154, Asp 157, Glu 158, Asn 160, and Tyr 163 of BIM SAHB.

The polypeptides of the present invention may have stabilized (e.g., cross-linked) alpha helical domains. Preferable the polypeptides are hydrocarbon-stapled. Hydrocarbon stapling is described in U.S. Publication No. 2005/0250680, which is herein incorporated by reference in its entirety.

As used herein, the term "hydrocarbon stapling", refers to a process for stably cross-linking a polypeptide having at least two modified amino acids that helps to conformationally bestow the native secondary structure of that polypeptide. Hydrocarbon stapling allows a polypeptide, predisposed to have an alpha-helical secondary structure, to maintain its native alpha-helical conformation. This secondary structure increases resistance of the polypeptide to proteolytic cleavage and heat, and also may increase hydrophobicity. Accordingly, the hydrocarbon stapled (cross-linked) polypeptides described herein (e.g., BH3 SAHB) have improved biological activity relative to a corresponding non-hydrocarbon stapled (uncrosslinked) polypeptide. For example the cross-linked polypeptide can include an alpha-helical domain of a BIM BH3 polypeptide, which can interact with a BAX active site.

The hydrocarbon stapled polypeptides include one or more tethers (linkages) between two non-natural amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence ... X1, X2, X3, X4, X5, X6, X7, X8, X9 ..., cross-links between X1 and X4, or between X1 and X5, or between X1 and X8 are useful as are cross-links between Xa2 and X5, or between X2 and X6, or between X2 and X9, etc. The use of multiple cross-links (e.g., 2, 3, 4 or more) is also contemplated. The use of multiple cross-links is very effective at stabilizing and optimizing the peptide, especially with increasing peptide length. Thus, the invention encompasses the incorporation of more than one crosslink within the polypeptide sequence to either further stabilize the sequence or facilitate the structural stabilization, proteolytic resistance, acid stability, thermal stability, and biological activity enhancement of longer polypeptide stretches. The process of hydrocarbon stapling is fully described in U.S. Patent Publication No. US2005/0250680, filed Nov. 5, 2004, which is herein incorporated by reference in its entirety.

In one embodiment, a SAHB polypeptide has the formula (I),

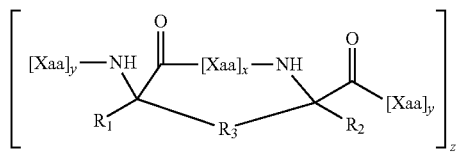

wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

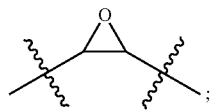 [SMILES: *C1OC1*]

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid. The SAHB polypeptides may includes an amino acid sequence described herein.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is —$CH_2$—$CH_2$—$CH_2$—CH=CH—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

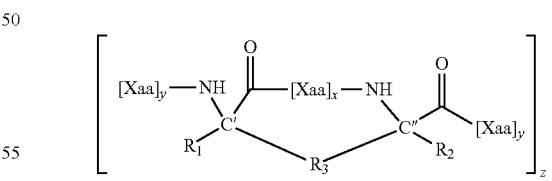

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some embodiments the SAHB polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of a BH3 domain. Each [Xaa]y is a peptide that can independently comprise at least 5, 6, 7, 8, 9, 10, 11, 12, 13, 14, 15, 16, 17, 18, 19, 20, 25 or more contiguous amino acids of a BH3 domain. [Xaa]x is a peptide that can comprise 3 or 6 contiguous amino acids of acids of a BH3 domain.

The SAHB polypeptide can comprise 3, 4, 5, 6, 7, 8, 9, 10, 11, 12, 13, 14, 15, 16, 17, 18, 19, 20, 25, 30, 35, 40, 45, 50 contiguous amino acids of acids of a BH3 domain, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as

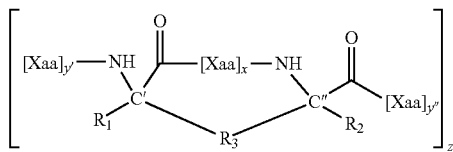

[Xaa]y' and [Xaa]y" can each comprise contiguous polypeptide sequences from the same or different BH3 domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a BH3 domain, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the SAHB polypeptides of the invention have the formula (II),

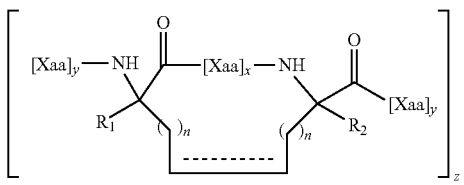

wherein each $R_1$ and $R_2$ are independently H, alkyl, alkenyl, alkynyl, arylalkyl, cycloalkylalkyl; heteroarylalkyl; or heterocyclylalkyl;

each n is independently an integer from 1-15;

x is 2, 3, or 6 each y is independently an integer from 0-100;

z is an integer from 1-10 (e.g., 1, 2, 3, 4, 5, 6, 7, 8, 9, 10);

each Xaa is independently an amino acid.

The modified polypeptide forms an alpha-helix and can have an amino acid sequence which is 30% or more identical to an amino acid sequence disclosed herein.

In still another embodiment, the SAHB polypeptides of the invention have the formula (III),

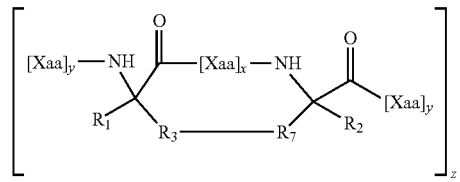

wherein;

each $R_1$ and $R_2$ are independently H, alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$ or a naturally occurring amino acid side chain; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_E$, $SO_2R_6$, $CO_2R_6$, $R_6$, a fluorescent moiety, or a radioisotope;

K is O, S, SO, $SO_2$, CO, $CO_2$, $CONR_6$, or

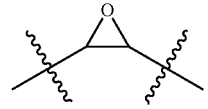 [SMILES: *C1OC1*]

$R_6$ is H, alkyl, or a therapeutic agent;

$R_7$ is alkyl, alkenyl, alkynyl; $[R_4—K—R_4]_n$ or an naturally occurring amino acid side chain; each of which is substituted with 0-6 $R_5$;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid;

The polypeptide forms and alpha-helix and includes an amino acid sequence which is about 30% or more identical to an amino acid sequence described herein.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids and also used in combination to install multiple tethers.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

V. Drug Design

Identification of this active site aids the development and identification of compounds which are capable of modulating BAX and other BCL-2 family polypeptides having a corresponding active site. For example, using this information, a three-dimensional computer generated interaction template of BAX can be generated by one of ordinary skill in the art and used to design activators and inhibitors specific for the BAX active site. In another embodiment, one of ordinary skill in the art can apply the BAX active site to identify corresponding active sites in other BCL-2 family members. This information may then be used to identify/develop compounds capable of modulating the other BCL-2 family polypeptides.

Determination of the three dimensional structure of the BCL-2 polypeptide and specifically the active site is critical to the rational identification and/or design of agents that may act as modulators of BCL-2 family polypeptide activity. This is advantageous over conventional drug assay techniques, in which the only way to identify such an agent is to screen thousands of test compounds until an agent having the desired inhibitory effect on a target compound is identified. Necessarily, such conventional screening methods are expensive, time consuming, and do not elucidate the method of action of the identified agent on the target compound. Using such a three dimensional structure, researchers identify putative binding sites and then identify or design agents to interact with these binding sites. These agents are then screened for a modulating effect upon the target molecule. In this manner, not only are the number of agents to be screened for the desired activity greatly reduced, but the mechanism of action on the target compound is better understood.

It is contemplated that identification of the BAX active site can be used to computationally screen small molecule databases for compounds that can bind in whole, or in part, to one or more of the regions of the BCL-2 family polypeptide's active site. In one embodiment of this method, the quality or fit of the compound identified to the regions of the active site can be judged either by shape complementarity or by estimated interaction energy (Meng et al., J. Comp. Chem. 13:505-524, 1992).

In a further embodiment, potential modulators that can be analyzed according to the methods of the invention can be obtained using any of the numerous approaches in combinatorial library methods known in the art. In one embodiment, potential modulators are first identified for pro-apoptotic or anti-apoptotic activity using the in vitro assays described herein or known in the art. Once potential modulators are identified, and their structures determined, further optimization can be carried out by computational analyses using the structure information of the BAX active site described herein. In another embodiment, a potential modulator is first identified in a screen using an interaction template developed from the structure coordinates of the BCL-2 family active site and further subjected to optimization by additional computational analyses. Alternatively, further optimization can be carried out by determining the NMR structural coordinates of co-complexes of the potential modulator and the BCL-2 family active site using the methods described herein.

Various combinatorial libraries that can be used in the methods of the invention include, but are not limited to: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

In a preferred embodiment, the library of compounds is a digital library. The binding interaction is performed with a database searching program which is capable of scanning a database of small molecules of known three-dimensional structure for candidates which fit into the active site. Suitable software programs include CATALYST (Molecular Simulations Inc., San Diego, Calif.), UNITY (Tripos Inc., St Louis, Mo.), FLEXX (Rarey et al., J. Mol. Biol. 261: 470-489 (1996)), CHEM-3-DBS (Oxford Molecular Group, Oxford, UK), DOCK (Kuntz et al., J. Mol. Biol. 161: 269-288 (1982)), and MACCS-3-D (MDL Information Systems Inc., San Leandro, Calif.) and LUDI (Boehm, J. Comp. Aid. Mol. Des. 6:61-78 (1992)), CAVEAT (Bartlett et al. in "Molecular Recognition in Chemical and Biological Problems", special publication of The Royal Chem. Soc., 78:182-196 (1989)) and MCSS (Miranker et al. Proteins 11:29-34 (1991)).

Further, examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

The potential modulator effect of a compound can be further analyzed prior to its actual synthesis and testing by use of computer modeling techniques using the structural coordinates of the BAX active site. If the computer modeling indicates an interaction, the molecule can then be synthesized using standard methods known to those skilled in the chemical arts, and then tested for its ability to modulate the activity of a BCL-2 family polypeptide using the assays set forth herein.

A modulator or other binding compound of a BCL-2 family polypeptide may be computationally evaluated and designed by means of a series of steps in which chemical entities or fragments are screened and selected for their ability to associate with the individual active site. In other embodiments of the method of the invention, potential modulator compounds can be examined for their ability to associate with a BCL-2 family polypeptide's active site and more particularly with a BAX active site. This process can involve visual inspection of, for example, the active site on a computer screen based on the structural coordinates of the BAX active site. Selected compounds or chemical moieties can then be positioned in a variety of orientations, or docked, within an individual region of the active site as defined herein. Docking can be accomplished using software such as Quanta and SYBYL, followed by energy minimization and molecular dynamics with standard molecular mechanics forcefields, such as CHARMM and AMBER.

In some embodiments, the invention involves the inputting of structural coordinates of BCL-2 family polypeptides into an electronic storage medium to generate a three-dimensional computer model of the polypeptide. In one embodiment, the complete structural coordinates of a BCL-2 family polypeptide are input. In an alternative embodiment, a fragment, or less than the complete structural coordinates, but including the active site are inputted. The structural coordinates may be known in the art or based on homology modeling. For example, known BCL-2 family structural coordinates include BAX (PDB ID No. 1f16), BAK (PDB ID No. 2ims), BCL-2 (PDB ID No. 1g5m), and BCL-XL (PDB ID No. 11x1), in addition to those associated with this invention: BIM BH3-BAX (PDB ID No. 2k7w), as well as others known in the art. Structural coordinates for many known BCL-2 family polypeptides can be obtained from the Protein Data Bank ("PDB") (Research Collaboratory for Structural Bioinformatics; http://www.rcsb.org).

The present invention further provides that the structural coordinates of the present invention may be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof (i.e., active sites). Homology modeling may be conducted by fitting common or homologous portions of the protein whose three dimensional structure is to be solved to the three dimensional structure of homologous structural elements in the known molecule, specifically using the relevant (i.e., homologous) structural coordinates. Homology may be determined using amino acid sequence identity, homologous secondary structure elements, and/or homologous tertiary folds. Homology modeling can include rebuilding part or all of a three dimensional structure with replacement of amino acid residues (or other components) by those of the related structure to be solved.

Similar methods are known to those skilled in the art (Greer, 1985, Science 228, 1055; Bundell et al 1988, Eur. J. Biochem. 172, 513; Knighton et al., 1992, Science 258:130-135, http://biochem.vt.edu/courses/modeling/homology.htm). Computer programs that can be used in homology modeling include Quanta and the homology module in the Insight II modeling package (Accelrys, Inc., San Diego, Calif.) or MODELLER (Rockefeller University, www.iucr.ac:uk/sinris-top/logical/prg-modeller.html, Sali's Modeller also from Accelrys, Inc., San Diego, Calif.).

Once an interaction template is prepared compounds which bind the BCL-2 family polypeptide's active site can be identified. Specialized computer programs that can also be used in the process of selecting compounds or chemical entities include:

1. SYBYL Available from Tripos Inc., 1699 South Hanley Rd., St. Louis, Mo., 63144, USA
2. UNITY Available from Tripos Inc., 1699 South Hanley Rd., St. Louis, Mo., 63144, USA
3. FlexX Available from Tripos Inc., 1699 South Hanley Rd., St. Louis, Mo., 63144, USA
4. GRID (Goodford, P. J., "A Computational Procedure for Determining Energetically Favorable Binding Sites on Biologically Important Macromolecules", J. Med. Chem., 28, pp. 849-857 (1985)). GRID is available from Oxford University, Oxford, UK.
5. MCSS (Miranker, A. and M. Karplus, "Functionality Maps of Binding Sites: A Multiple Copy Simultaneous Search Method." Proteins: Structure. Function and Genetics, 11, pp. 29-34 (1991)). MCSS is available from Molecular Simulations, Burlington, Mass.
6. AUTODOCK (Goodsell, D. S, and A. J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.
7. DOCK (Kuntz, I. D. et al., "A Geometric Approach to Macromolecule-Ligand Interactions", J. Mol. Biol., 161, pp. 269-288 (1982)). DOCK is available from University of California, San Francisco, Calif.

Once suitable compounds or chemical moieties have been selected, they can be assembled into a single compound or inhibitor. Assembly may be proceed by visual inspection of the relationship of the compounds or moieties to each other on the three-dimensional image displayed on a computer screen in relation to the structure coordinates of the BAX/BIM-BH3 NMR binding studies. This could then be followed by manual model building using software such as Quanta or SYBYL.

Other useful programs to aid one of skill in the art in connecting the individual compounds or chemical entities include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)).
3. HOOK (available from Molecular Simulations, Burlington, Mass.).

In other embodiments, BCL-2 family polypeptide modulators can be designed as a whole or "de novo" using either an empty active site or optionally including some portion(s) of a known modulator(s). Programs which can aid in these methods include:

1. LUDI (Bohm, H.-J., "The Computer Program LUDI: A New Method for the De Novo Design of Enzyme Inhibitors", J. Comp. Aid. Molec. Design, 6, pp. 61-78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Once a compound has been designed or selected by the above methods, the efficiency with which that compound modulates a BCL-2 family polypeptide can be tested and optimized by computational evaluation. An effective BCL-2 family polypeptide modulator must preferably demonstrate a relatively small difference in energy between its bound and free states (i.e., a small deformation energy of binding).

A compound designed or selected as a modulator of BCL-2 family polypeptide can be further computationally optimized so that in its bound state it would preferably lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the modulator and the enzyme when the modulator is bound to BCL-2 family polypeptide preferably make a neutral or favorable contribution to the enthalpy of binding.

Specific computer software is available in the art to evaluate compound deformation energy and electrostatic interaction. Examples of programs designed for such uses include: Gaussian 92, revision C, M. J. Frisch, Gaussian, Inc., Pittsburgh, Pa.; AMBER, version 4.0, P. A. Kollman, University of California at San Francisco; QUANTA/CHARMM, Molecular Simulations, Inc., Burlington, Mass.; and Insight II/Discover (Biosysm Technologies Inc., San Diego, Calif.). These programs may be implemented, for instance, using a Silicon Graphics workstation, IRIS 4D/35 or IBM RISC/6000 workstation model 550. Other hardware systems and software packages will be known to those skilled in the art.

Furthermore, fragment-based drug discovery can be used to identify compounds which interact with the active site of BAX. These methods are known and computational tools for their use are commercially available, for example "SAR by NMR" (Shukers, S. B., et al., Science, 1996, 274, 1531-1534), "Fragments of Active Structures" (www.stromix.com; Nienaber, V. L., et al., Nat. Biotechnol., 2000, 18, 1105-1108), and "Dynamic Combinatorial X-ray Crystallography" (e.g., permitting self-selection by the protein molecule of self-assembling fragments; Congreve, M. S., et al., Angew. Chem., Int. Ed., 2003, 42, 4479-4482).

Once a BCL-2 family polypeptide modulator has been optimally selected or designed, as described herein, substitutions can then be made in some of its atoms or side groups in order to improve or modify its binding properties, again using the information provided by the interaction and specificity templates to identify regions amiable to modification. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to BCL-2 family polypeptides by the same computer methods described in detail, above.

In certain embodiments the modulators have a Kd for BCL-2 family polypeptides of less than 0.2 mM, less than 0.1 mM, less than 750 µM, less than 500 µM, less than 250 µM, less than 100 µM, less than 50 µM, less than 500 nM, less than 250 nM, less than 50 nM, less than 30 nm, less than 20 nM, less than 10 nM, less than 5 nM, less than 3 nM, less than 1 nM, or less than 0.5 nM.

Designed modulators can be further evaluated using in vitro or in vivo assays known in the art and described herein.

IV. In Vitro Assays for Assessing BCL-2 Family Peptide Modulation and Compound Binding Determining the ability of a compound, found to bind the active site of a BCL-2 family polypeptide based on computer modeling, library screening, and/or fragment-based drug discovery, can be evaluate further for BCL-2 family polypeptide interaction by testing direct binding. Determining the ability of a test compound to bind to a BCL-2 family polypeptide can be accomplished, for example, by coupling the BCL-2 family polypeptide or compound with a radioisotope or enzymatic label such that binding of the BCL-2 family polypeptide to the potential modulator can be determined by detecting the labeled BCL-2 family polypeptide in a complex. For example, a compound can be labeled with $^{125}$I, $^{35}$S, $^{14}$C, or $^{3}$H, either directly or indirectly, and the radioisotope detected by direct counting of radioemission or by scintillation counting. Alternatively, the compound can be enzymatically labeled with, for example, horseradish peroxidase, alkaline phosphatase, or luciferase, and the enzymatic label detected by determination of conversion of an appropriate substrate to product. As a further example, the compound can be labelled with fluorescein and binding interactions between ligand and BCL-2 family polypeptide quantitated using a fluorescence polarization assay. Binding can also be measured by HSQC NMR, as described herein.

In other embodiments, determining the ability of the modulator to bind to BCL-2 family polypeptides can be determined by detecting induction of a downstream event (e.g., change in conformation, oligomerization state, or subcellular localization of the polypeptide, apoptosis, release of mitochondrial cytochrome c, etc.) or detecting another BCL-2 family-regulated cellular response.

In another embodiment, the assay is a cell-free assay in which a BCL-2 family protein or biologically active portion thereof containing an active site is contacted with a test compound and the ability of the test compound to modulate the activity of the BCL-2 family protein or biologically active portion thereof is determined. Determining the ability of the test compound to modulate the activity of a BCL-2 family protein can be accomplished, for example, by determining the ability of the BCL-2 family protein to bind to another BCL-2 family target molecule (e.g., BAX binding to a hydrocarbon-stapled BIM BH3 polypeptide) in the presence of the test compound.

Determining the ability of the BCL-2 family protein to bind to a target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BLAcore). Changes in the optical phenomenon of surface plasmon resonance (SPR) can be used as an indication of real-time reactions between biological molecules.

In an alternative embodiment, determining the ability of the test compound to modulate the activity of a BCL-2 family protein can be accomplished by determining the ability of the BCL-2 family protein to modulate the activity of a downstream BCL-2 family target molecule. For example, the activity of the effector molecule on an appropriate target can be determined, or the binding of the effector to an appropriate target can be determined as previously described.

In yet another embodiment, the cell-free assay involves contacting a BCL-2 family protein (e.g., BAX) or biologically active portion thereof containing the active site, with a known compound which binds the BCL-2 family protein (e.g. a hydrocarbon-stapled BIM BH3 polypeptide) to form an assay, and determining the ability of the test compound to interact with the BCL-2 family protein, wherein determining the ability of the test compound to interact with the BCL-2 family protein comprises determining the ability of the test compound to preferentially bind to or modulate the activity of a BCL-2 family protein and displace the known compound.

In more than one embodiment of the above assay methods of the present invention, it may be desirable to immobilize either the BCL-2 family polypeptide or its target molecule to facilitate separation of complexed from uncomplexed forms of one or both of the proteins, as well as to accommodate automation of the assay. Binding of a test compound to a BCL-2 family protein, or interaction of a BCL-2 family protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione -S-transferase/BCL-2 family fusion proteins or glutathione-S-transferase/target fusion proteins can be adsorbed onto glutathione SEPHAROSE® beads (Sigma Chemical, St. Louis, Mo.) or glutathione derivatized microtiter plates, which are then combined with the test compound or the test compound and either the non-adsorbed target protein or BCL-2 family protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of BCL-2 family binding or activity determined using standard techniques.

Other techniques for immobilizing proteins on matrices can also be used in the assays of the invention. For example, either a BCL-2 family protein or a BCL-2 family target molecule can be immobilized utilizing conjugation of biotin and streptavidin. Biotinylated BCL-2 family protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with BCL-2 family protein or target molecules but which do not interfere with binding of the BCL-2 family protein to its target molecule can be derivatized to the wells of the plate, and unbound target or BCL-2 family protein trapped in the wells by antibody conjugation. Methods for detecting such complexes, in addition to those described above for the GST-immobilized complexes, include immunodetection of complexes using antibodies reactive with the BCL-2 family protein or target molecule, as well as enzyme-linked assays which rely on detecting an enzymatic activity associated with the BCL-2 family protein or target molecule.

The compounds that bind the active site of BCL-2 family polypeptides may be demonstrated to inhibit tumor cell number in vitro or in vivo using a variety of assays known in the art, or described herein. Such assays can use cells of a cancer cell line or cells from a patient in the presence and absence of the compound of interest. Preferably the cell has a deregulated BCL-2 family polypeptide pathway. The ability of a compound or a regimen of the invention to reduce the number of cancer cells or inhibit their proliferation can be assessed by methods known in the art and described herein.

The invention provides methods (also referred to herein as "screening assays") for identifying compounds which bind to an active site and modulate the activity of one or more BCL-2 family proteins.

Figure 12A:
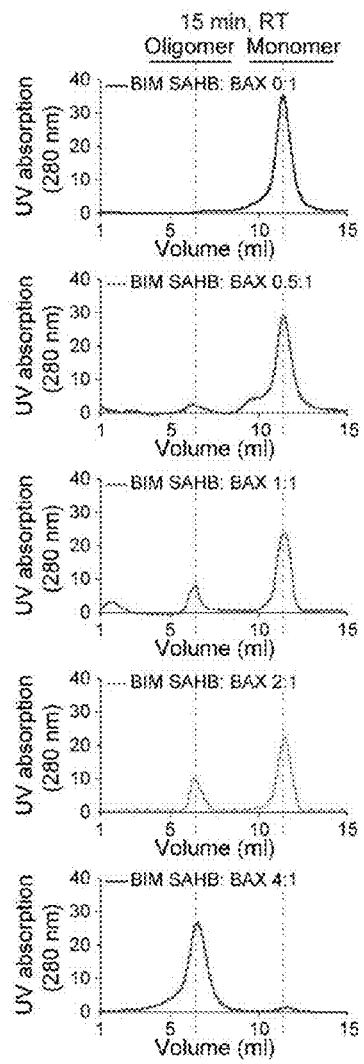
FIG. 12 BIM SAHB directly initiates BAX oligomerization in vitro and triggers the functional release activity of BAX. (a) Treatment of monomeric BAX with BIM SAHB at the indicated ratios induced dose-responsive BAX oligomerization as reflected by size exclusion chromatography-based monitoring of the monomer-oligomer states after 15 minutes incubation at room temperature. (b) BIM SAHB-BAX mixtures at the corresponding ratios were incubated with 6A7 antibody followed by immunoprecipitation to assess ligand-induced exposure of the BAX N-terminal epitope (residues 12-24), a reflection of the conformational change in BAX observed upon activation. The quantity of immunoprecipitated BAX increased in accordance with the BIM SAHB-BAX ratio. Specific and high potency functional activation of BAX by BIM SAHB is further demonstrated by (c) an in vitro FITC-dextran liposomal release assay and (d) mitochondrial cytochrome c release.
Figure 12B:
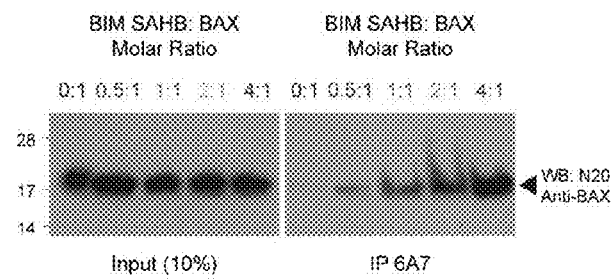
Figure 12C:
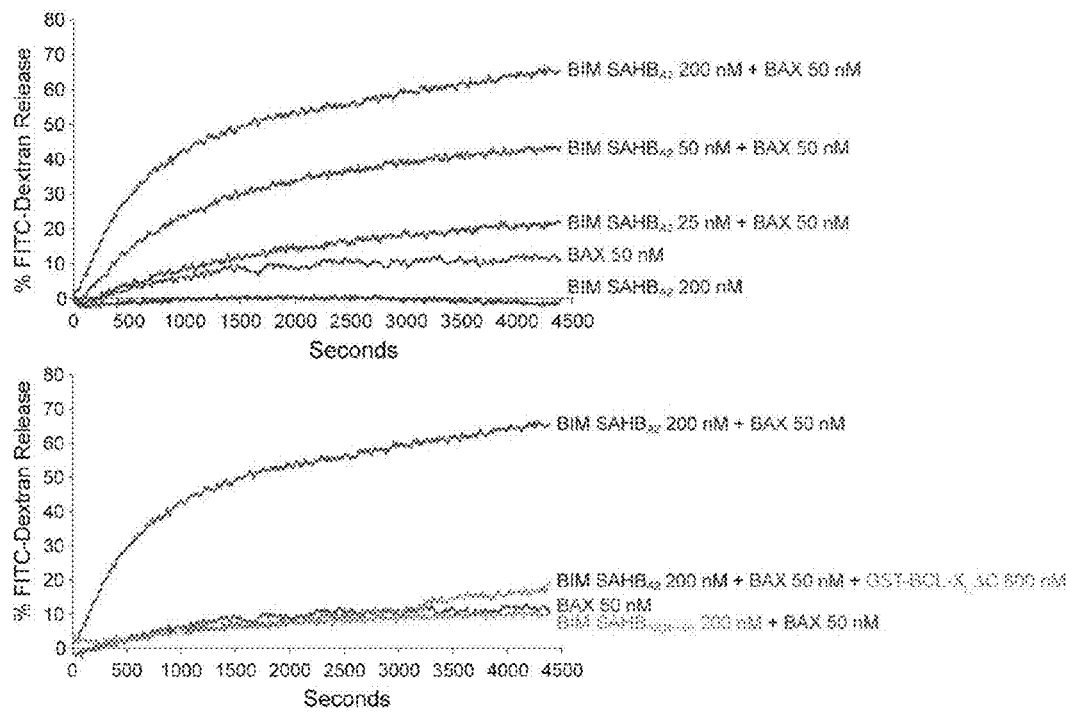
Figure 12D:
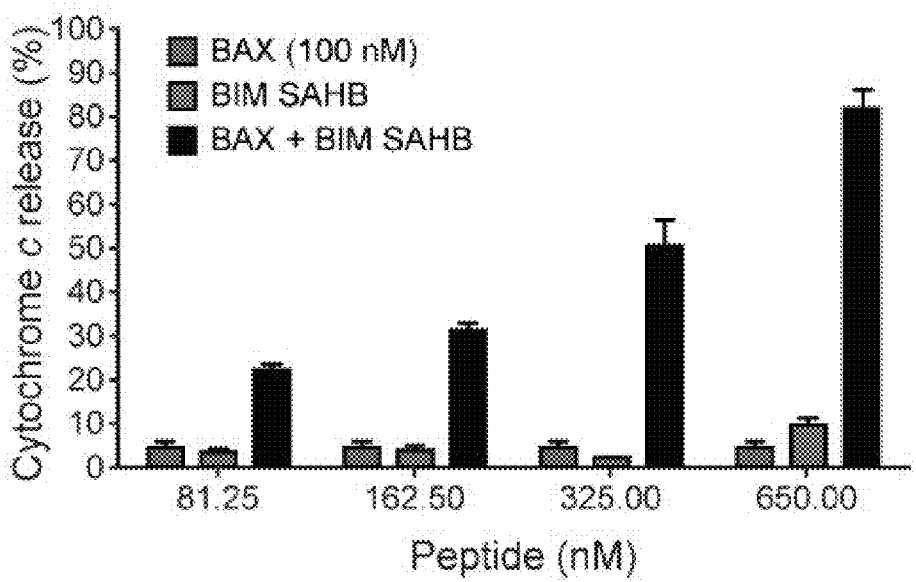

The binding affinity of polypeptides described herein can be determined using, for example, a titration binding assay. A BCL-2 family polypeptide or polypeptide comprising a BH domain (e.g., BAX, etc.) can be exposed to varying concentrations of a candidate compound (i.e., polypeptide, small molecule) (e.g., 1 nM, 10 nM, 100 nM, 1 uM, 10 uM, 100 uM, 1 mM, and 10 mM) in the presence of a substrate such as a fluorescently labeled BH3 containing polypeptide or a fragment thereof (e.g., BID, BAD, BAK, BAX, etc.). The effect of each concentration of candidate compound is then analyzed to determine the effect of the candidate compound on BCL-2 family polypeptide binding activity at varying concentrations, which can be used to calculate the Ki of the candidate compound. The candidate compound can modulate BCL-2 type activity in a competitive or non-competitive manner. Direct binding assays can also be performed between BCL-2 family proteins and fluorescently labeled candidate compounds to determine the Kd for the binding interaction. Candidate compounds could also be screened for biological activity in vitro, for example, by measuring their dose-responsive efficacy in triggering BCL-2 family protein conformational change as measured by conformation-specific antibodies (e.g. BAX 6A7 antibody, FIG. 12b) or HSQC NMR analysis, a change in BCL-2 family protein (e.g. BAX) oligomerization state as monitored by size exclusion chromatography (SEC)-based analysis (FIG. 12a, 13b, 13d) or dynamic light scattering, fluorophore or protein-conjugated fluorophore-induced release from liposomes, and/or cytochrome c release from purified mitochondria (FIGS. 12c, 12d). Cell permeability screening assays are also envisioned, in which fluorescently or otherwise labeled candidate compounds are applied to intact cells, which are then assayed for cellular fluorescence by microscopy or high-throughput cellular fluorescence detection.

A compound, pharmaceutical composition, or regimen of the invention is preferably tested in vitro and then in vivo for the desired therapeutic or prophylactic activity prior to use in humans. For example, assays which can be used to determine whether administration of a specific compound is effective include cell culture assays in which a patient tissue sample (e.g., cancer cell) is grown in culture and exposed to, or otherwise contacted with, a compound of the invention, and the effect of such compound upon the tissue sample is observed. The tissue sample can be obtained by biopsy or blood/bone marrow draw from the patient. This test allows the identification of the therapeutically most effective therapy (e.g., prophylactic or therapeutic agent) for each individual patient.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

In a preferred embodiment, cell-based assay is performed on a compound which is known to bind an active site (e.g., identified via computer modeling, direct binding assay, NMR, or other method) of a BCL-2 family polypeptide in order to determine whether the compound also modulates the activity of the BCL-2 family polypeptide.

In one embodiment, an assay is a cell-based assay in which a cell that expresses a BCL-2 family protein or biologically active portion thereof is contacted with a candidate compound, and the ability of the candidate compound to bind to an active site and modulate BCL-2 family type activity is determined (e.g., in some instances increase in apoptosis and in other instances decrease apoptosis, via intrinsic or extrinsic cell death pathways). Determining the ability of the test compound to modulate BCL-2 type activity within cells can be accomplished by monitoring, for example, release of cytochrome c from the mitochondria or other relevant physiologic readout (e.g., annexin V staining, MTT assay, caspase activity assay, TUNEL assay, change in mitochondrial membrane potential).

In vitro anti-tumor activity of the compounds found to bind to the active site of a BCL-2 polypeptide can be assayed by measuring the ability of the compound to kill tumor cells. Examples of cell lines include: human lung (A549); resistant human lung with low topo II activity (A549-VP); murine melanoma (B16); human colon tumor (HCT116); human clone tumor with elevated p170 levels (HCTVM); human colon tumor with low topo II activity (HCTVP); P388 murine lymph leukemia cells; and human colon carcinoma cell line (Moser), and many others known in the art.

Tumor inhibition assays are described, for example, in Kelly, et al., U.S. Pat. No. 5,166,208, and in Pandley, et al., J. Antibiot. 3(11):1389-401 (1981). In one assay, the cells are allowed to grow for a 24 hour period under standard conditions. After the cells are allowed to attach to the plate for 24 hours (e.g., a 96-well flat bottom plate), the cells are incubated for 72 hours with serially diluted concentrations of the BCL-2 family modulator compound. From these data, the concentration of the compound at which 50% of the cells are killed or growth inhibited (IC50) is determined.

VII. In Vivo Testing of Compounds

The compounds of the invention can also be demonstrated to inhibit tumor formation in vivo. The compounds, pharmaceutical compositions, and regimens of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapeutic modalities (e.g., prophylactic and/or therapeutic agents), whether such therapeutic modalities are administered separately or as an admixture, and the frequency of administration of the therapeutic modalities.

In vivo anti-tumor activity of BCL-2 family modulator compounds of the invention can be assayed by a reduction of tumor cells in mammals (e.g., mice) and a resulting increase in survival time compared to untreated tumor bearing animals. For example, CDF1 mice are injected interperitoneally with a suspension of P388 murine lymph leukemia cells, Ehrlich carcinoma cells, B16 melanoma cells, or Meth-A fibrosarcoma cells. Some of the injected mice are then treated interperitoneally with a BCL-2 family modulator compound of the invention, and other mice are treated with saline. The in vivo activity of the compound is then determined in terms of the % T/C which is the ratio of the mean survival time of the treated group to the mean survival time of the saline treated group times 100. Yokoi, et al., U.S. Pat. No. 4,584,377; Kelly, et al., U.S. Pat. No. 5,155,208; Warnick-Pickle, et al., J. Antibiot. 34(11):1402-7 (1981); and Pandley et al., supra.

A vast number of animal models of hyperproliferative disorders, including tumorigenesis and metastatic spread, are known in the art and are disclosed herein (see Chapter 317, "Principals of Neoplasia," in Harrison's: Principals of Internal Medicine, 13th Edition, Isselbacher et al., eds., McGraw-Hill, New York, p. 1814, and Lovejoy et al., 1997, J. Pathol. 181:130-135). Hyperpoliferative disorders include cellular proliferation or apoptotic blockage disorders such as cancer and autoimmune disease. Examples of BCL-2 related cancers include, but are not limited to, solid tumors, leukemias, and lymphomas. In one embodiment, the disorder is a chemoresistant cancer. In a more preferred embodiment, the chemoresistant cancer is resistant to ABT-737 (available from Abbott; Abbott Park, Ill.). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. Supp 12:45-47) and mouse models with mutations of the adenomatous polyposis tumor suppressor (Polakis, 1997, Biochim. Biophys. Acta 1332:F127-F147); for breast cancer, kansgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 5 1996, Breast Cancer Res. Treat. 39:7-20); for prostate cancer, chemically-induced and transgenic rodent models, and human xenograft models (Royal et al., 1996, Semin. Oncol. 23:35-40), for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat 15 (Frey, 1997, Methods, 12:173-188).

For example, a compound of the invention can be administered to a test animal, in one embodiment a test animal predisposed to develop a type of tumor, and the test animal subsequently examined for a decreased incidence of tumor formation in comparison with an animal not administered the compound. Alternatively, a compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the compound. A compound of the invention is considered effective in treating a hyperpoliferative disorder when administration of a therapeutically effective amount increases time to tumor progression or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Similarly, a compound of the invention is considered effective in treating a hyperpoliferative disorder when administration of a therapeutically effective amount decreases the rate of tumor growth, decreases tumor mass, decreases the number of metastases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Such results can be determined by one having ordinary skill in the relevant art, e.g., oncologist.

Further, any assays known to those skilled in the art can be used to evaluate the prophylactic and/or therapeutic utility of a compound or pharmaceutical composition disclosed herein for disorder associated with excessive cellular proliferation or cellular death or one or more symptoms thereof.

VIII. Methods of Treatment

Agents of the present invention are useful for treating cells in which the cell death signal is down regulated and the affected cell has an inappropriately diminished propensity for cell death, which is referred to herein as being in a "decreased apoptotic state." The invention further provides methods for the administration to a subject of a therapeutically effective amount of an agent to treat an apoptosis-associated disease in which it is desirable to induce apoptosis in certain types of cells, such as virus-infected or autoantibody-expressing cells. Typically, the agent is substantially purified prior to administration. The subject can be an animal, including but not limited to, cows, pigs, horses, chickens, cats, dogs, and the like, and is typically a mammal, and in a particular embodiment human. In another specific embodiment, a non-human mammal is the subject.

The present invention provides for both prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities). As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes, antisense oligonucleotides, other nucleic acid compositions, and combinations thereof.

BCL-2 type disorders can be caused, at least in part, by an abnormal level of one or more BCL-2 family members (e.g., over or under expression of BCL-2), or by the presence of one or more BCL-2 family members exhibiting abnormal activity. As such, the invention is directed to the reduction in the level and/or activity of the BCL-2 family member or the enhancement of the level and/or activity of the BCL-2 family member, which would bring about the amelioration of disorder symptoms. For example, a tumor maintained by excessive levels of an anti-apoptotic protein such as BCL-2, can be treated with a BAX activating modulator compound in order to surmount or circumvent apoptotic blockade and directly induce BAX-mediated apoptosis.

The compounds of the invention can be used to treat and prevent cancers and neoplastic conditions. As used herein, the terms "cancer", "hyperproliferative" and "neoplastic" refer to cells having the capacity for autonomous growth and defective cell death, i.e., an abnormal state or condition characterized by rapidly proliferating cell growth and/or apoptotic blockade. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The compounds can act as novel therapeutic agents for controlling breast cancer, ovarian cancer, colon cancer, lung cancer, metastasis of such cancers and the like. A metastatic tumor can arise from a multitude of primary tumor types, including but not limited to those of breast, lung, liver, colon and ovarian origin.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, nonneoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The compounds described herein can also be used to treat or prevent conditions characterised by overactive cell death or cellular death due to physiologic insult etc. Some examples of conditions characterized by premature or unwanted cell death are or alternatively unwanted or excessive cellular proliferation include, but are not limited to ischemia, hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia.

Compounds of the invention that act to decrease apoptosis can be used to treat disorders associated with an undesirable level of cell death. Thus, the anti-apoptotic compounds of the invention can be used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic peptides of the infection can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic compounds of the invention can be used to treat all such disorders associated with undesirable cell death.

Some examples of immunologic disorders that can be treated with the compounds described herein include but are not limited to organ transplant rejection, arthritis, lupus, IBD, crone's disease, asthma, multiple sclerosis, diabetes etc.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, and Huntington's Disease.

Some examples of endocrinologic disorders that can be treated with the polypeptides described herein include but are not limited to diabetes, hypthyroidism, hyopituitarism, hypoparathyroidism, hypogonadism, etc.

Examples of cardiovascular disorders (e.g., inflammatory disorders) that can be treated or prevented with the compounds and methods of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

IX. Administration of Modulators

In one embodiment, the compounds of the invention are administered as monotherapy for the prevention, treatment, and/or management of cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a compound of the invention or a composition of the invention, wherein the patient has been diagnosed with cancer. The amount of a compound of the invention used in the prophylactic and/or therapeutic regimens which will be effective in the prevention, treatment, and/or management of cancer can be based on the currently prescribed dosage of the compound as well as assessed by methods disclosed herein.

In one embodiment of this aspect, the patient has received or is receiving another therapy. In another embodiment of this aspect, the patient has not previously received a therapy for the prevention, treatment, and/or management of the cancer.

The medical practitioner can diagnose the patient using any of the conventional cancer screening methods including, but not limited to physical examination (e.g., prostate examination, breast examination, lymph nodes examination, abdominal examination, skin surveillance), visual methods (e.g., colonoscopy, bronchoscopy, endoscopy), PAP smear analyses (cervical cancer), stool guaiac analyses, blood tests (e.g., complete blood count (CBC) test), blood chemistries including liver function tests, prostate specific antigen (PSA) test, carcinoembryonic antigen (CEA) test, cancer antigen (CA)-125 test, alpha-fetoprotein (AFP)), karyotyping analyses, bone marrow analyses (e.g., in cases of hematological malignancies), histology, cytology, a sputum analysis and imaging methods (e.g., computed tomography (CT), magnetic resonance imaging (MRI), ultrasound, X-ray imaging, mammograph imaging, bone scans).

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient a compound or composition of the invention wherein the patient has been diagnosed with a solid tumor, and wherein the patient has undergone a primary therapy to reduce the bulk of the tumor.

Another aspect of the invention relates to a method of preventing, treating, and/or managing cancer, the method comprising administering to a patient in need thereof a prophylactically effective regimen or a therapeutically effective regimen, the regimen comprising administering to the patient a compound of the invention (as described above), or a pharmaceutically acceptable salt thereof wherein the patient received another therapy. In some embodiments, the prior therapy is, for example, chemotherapy, radioimmunotherapy, toxin therapy, prodrug-activating enzyme therapy, antibody therapy, surgical therapy, immunotherapy, radiation therapy, targeted therapy or any combination thereof.

In some embodiments, the prior therapy has failed in the patient. In some embodiments, the therapeutically effective regimen comprising administration of a compound of the invention is administered to the patient immediately after patient has undergone the prior therapy. For instance, in certain embodiments, the outcome of the prior therapy may be unknown before the patient is administered a compound of the invention.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient a compound or composition of the invention, wherein the compound or composition of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005.

In certain embodiments, the regimens comprise administering a prophylactically effective regimen and/or a therapeutically effective regimen, wherein the regimen results in a reduction in the cancer cell population in the patient. In one embodiment, the patient undergoing the regimen is monitored to determine whether the regimen has resulted in a reduction in the cancer cell population in the patient.

Typically, the monitoring of the cancer cell population is conducted by detecting the number or amount of cancer cells in a specimen extracted from the patient. Methods of detecting the number or amount of cancer cells in a specimen are known in the art. This monitoring step is typically performed at least 1, 2, 4, 6, 8, 10, 12, 14, 15, 16, 18, 20, or 30 days after the patient begins receiving the regimen.

In some embodiments, the specimen may be a blood specimen, wherein the number or amount of cancer cells per unit of volume (e.g., 1 mL) or other measured unit (e.g., per unit field in the case of a histological analysis) is quantitated. The cancer cell population, in certain embodiments, can be determined as a percentage of the total blood cells.

In other embodiments, the specimen extracted from the patient is a tissue specimen (e.g., a biopsy extracted from suspected cancerous tissue), where the number or amount of cancer cells can be measured, for example, on the basis of the number or amount of cancer cells per unit weight of the tissue.

The number or amount of cancer cells in the extracted specimen can be compared with the numbers or amounts of cancer cells measured in reference samples to assess the efficacy of the regimen and amelioration of the cancer under therapy. In one embodiment, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the cancer cell population in the extracted specimen can be compared with a predetermined reference range. In a specific embodiment, the predetermined reference range is based on the number or amount of cancer cells obtained from a population(s) of patients suffering from the same type of cancer as the patient undergoing the therapy.

If the reduction in the cancer cell population is judged too small upon comparing the number, amount, or percentage of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

In other embodiments, the regimens comprise administering a compound or composition of the invention, wherein the regimen results in a reduction in the number, amount, or percentage of cancer cells and a reduction in the number, amount, or percentage of cancer cells in the patient.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some embodiments, the prophylactic and/or therapeutic regimens comprise titrating the dosages administered to the patient so as to achieve a specified measure of therapeutic efficacy. Such measures include a reduction in the cancer cell population in the patient.

In certain embodiments, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic and/or therapeutic regimen. In specific embodiments, the number or amount of cancer cells in the test specimen is at least 2%, 5%, 10%, 15%, 20%, 30%, 40%, 50%, 60%, 70%, 80%, 90%, 95% or 99% lower than in the reference sample.

In some embodiments, the dosage of the compound of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. In specific embodiments, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these embodiments, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., $mg/m^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one embodiment, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. In one embodiment, the frequency of administration ranges from once a day up to about once every eight weeks. In another embodiment, the frequency of administration ranges from about once a week up to about once every six weeks. In another embodiment, the frequency of administration ranges from about once every three weeks up to about once every four weeks.

Generally, the dosage of a compound of the invention administered to a subject to prevent, treat, and/or manage cancer is in the range of 0.01 to 500 mg/kg, and more typically, in the range of 0.1 mg/kg to 100 mg/kg, of the subject's body weight. In one embodiment, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight.

In a specific embodiment, the dosage of a compound of the invention administered to a subject to prevent, treat, and/or manage cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another specific embodiment, the dosage of a compound of the invention administered to a subject to prevent, treat, and/or manage cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In a specific embodiment, the dosage of a compound of the invention administered to a subject to prevent, treat, and/or manage cancer in a patient is in the range of 0.01 to 10 g/m², and more typically, in the range of 0.1 g/m² to 7.5 g/m², of the subject's body weight. In one embodiment, the dosage administered to a subject is in the range of 0.5 g/m² to 5 g/m², or 1 g/m² to 5 g/m² of the subject's body's surface area.

In other embodiments, the prophylactic and/or therapeutic regimen comprises administering to a patient one or more doses of an effective amount of a compound of the invention, wherein the dose of an effective amount achieves a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention.

In other embodiments, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

In some embodiments, the prophylactic and/or therapeutic regimen comprises administration of a compound of the invention in combination with one or more additional anticancer therapeutics. Preferably, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10*th ed.*, Mc-Graw-Hill, New York, 2001; *Physician's Desk Reference* (60*th* ed., 2006), which is incorporated herein by reference in its entirety.

The compound of the invention and the one or more additional anticancer therapeutics can be administered separately, simultaneously, or sequentially. In various embodiments, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more anticancer therapeutics are administered within the same patient visit.

In certain embodiments, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies.

In a preferred embodiment, the anticancer therapeutics are administered concurrently to a subject in separate compositions. The combination anticancer therapeutics of the invention may be administered to a subject by the same or different routes of administration.

In a specific embodiment, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

When a compound of the invention and the additional anticancer therapeutic are administered to a subject concurrently, the term "concurrently" is not limited to the administration of the anticancer therapeutics at exactly the same time, but rather, it is meant that they are administered to a subject in a sequence and within a time interval such that they can act together (e.g., synergistically to provide an increased benefit than if they were administered otherwise). For example, the anticancer therapeutics may be administered at the same time or sequentially in any order at different points in time; however, if not administered at the same time, they should be administered sufficiently close in time so as to provide the desired therapeutic effect, preferably in a synergistic fashion. The combination anticancer therapeutics of the invention can be administered separately, in any appropriate form and by any suitable route. When the components of the combination anticancer therapeutics are not administered in the same pharmaceutical composition, it is understood that they can be administered in any order to a subject in need thereof. For example, a compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various embodiments, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the anticancer therapeutics are administered within the same office visit. In another embodiment, the combination anticancer therapeutics of the invention are administered at 1 minute to 24 hours apart.

X. Formulations

The present invention provides compositions that are suitable for veterinary and/or human administration (e.g., pharmaceutical compositions). The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The formulation of a compound of the invention used in the prophylactic and/or therapeutic regimens which will be effective in the prevention, treatment, and/or management of cancer can be based on the currently available formulation. Alternatively the compounds can be reformulated based on knowledge within the art and the teachings herein. For example, the compound may be in the form of a solid, liquid or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow a compound of the invention to be bioavailable upon administration of the composition to a subject. Compositions can take the form of one or more dosage units, where, for example, a tablet can be a single dosage unit, and a container of a compound of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the compound of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the compounds of the invention and pharmaceutically acceptable carriers are sterile. Water is a preferred carrier when the compound of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of a compound of the invention such that a suitable dosage will be obtained. The pharmaceutical compositions may comprise the known effective amount of the compounds as currently prescribed for their respective disorders.

Typically, the effective amount is at least 0.01% of a compound of the invention by weight of the composition. When intended for oral administration, this amount can be varied to be between 0.1% and 80% by weight of the composition. Preferred oral compositions can comprise from between 4% and 50% of the compound of the invention by weight of the composition. Preferred compositions of the present invention are prepared so that a parenteral dosage unit contains from between 0.01% and 2% by weight of the compound of the invention.

The compounds of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a compound of the invention. In certain embodiments, more than one compound of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In one embodiment, the compounds of the invention are administered parenterally. In a specific embodiment, the compounds of the invention are administered intravenously.

In specific embodiments, it can be desirable to administer one or more compounds of the invention locally to the area in need of treatment (e.g., location of the tumor or ischemic condition). This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor, or precancerous tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and carriers such as triglycerides.

In yet another embodiment, the compounds of the invention can be delivered in a controlled release system. In one embodiment, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). In another embodiment, polymeric materials can be used (*see Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.,* 1989, 25, 351; Howard et al., *J. Neurosurg.,* 1989, 71, 105). In yet another embodiment, a controlled-release system can be placed in proximity of the target of the compounds of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

In another embodiment, polymeric materials can be used to achieve controlled or sustained release of the compounds of the invention (see, e.g., U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

Whether in solid, liquid or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a compound of the invention, an additional anti-cancer agent, and a pharmaceutically acceptable carrier or vehicle.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are provided merely as illustrative of various aspects of the invention and shall not be construed to limit the invention in any way.

EXAMPLES

Example 1

Figure 4B:
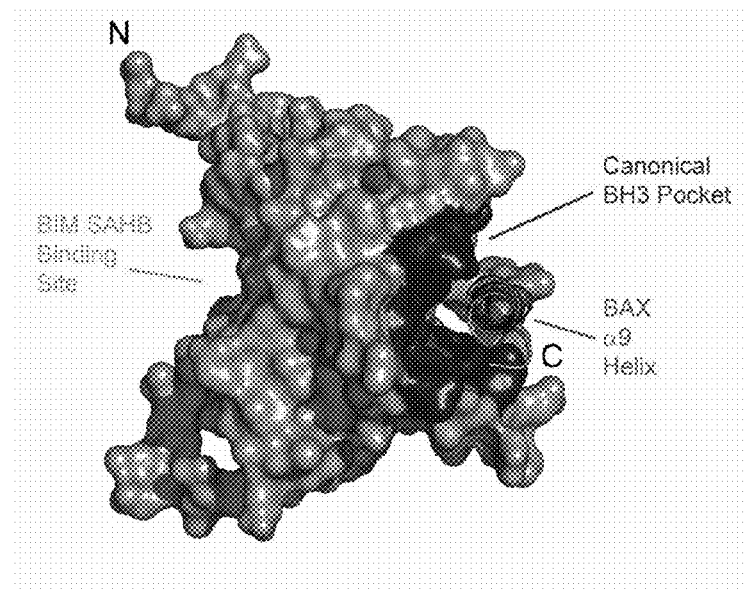
Figure 7:
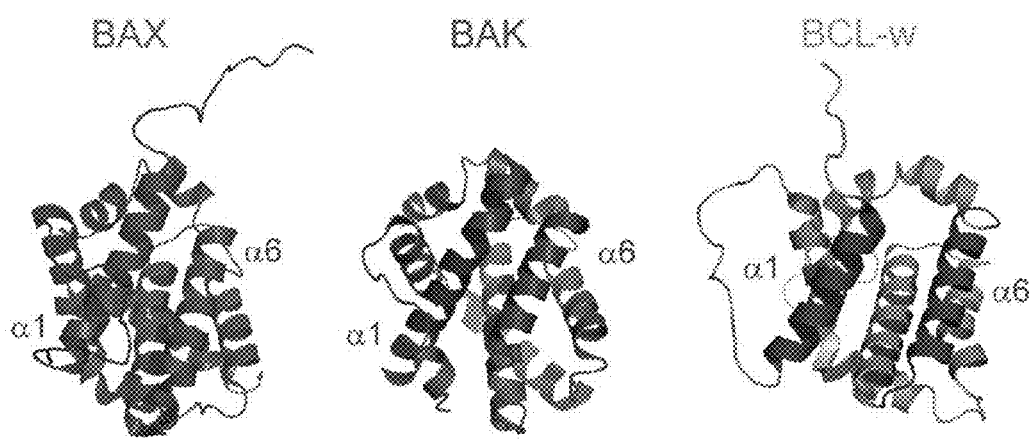
FIG. 7 illustrates the α1 and α6 domains of BAX, BAK and BCL-w.

Identification of a BH3 Interaction Site on BAX that Triggers its Functional Activation A Stabilized-Alpha Helix of-BCL-2 Domain or SAHB corresponding to a 21 amino acid fragment of human BIM BH3 (BIM SAHB$_{A1}$) exhibited 81% alpha-helicity in aqueous solution, bound to pro-apoptotic BAX with 24 nM affinity,[3] and was prepared as previously described (Walensky, L. D., et al. *Mol Cell* 24(2), 199-210 (2006)). An alpha-helical N-acetylated and C-amidated 20-mer (FIG. 8) BIM SAHB derivative (BIM SAHB$_{A2}$), and other analogs, were prepared for structural studies. BIM SAHB$_{A2}$ formed a 1:1 stable complex with BAX in aqueous solution at concentrations up to 0.5 mM. The circular dichroism spectra of BIM SAHBs demonstrated that these engineered peptide recapitulate the alpha-helical structure of native BH3 domains. Heteronuclear Single Quantum Correlation (HSQC) titrations employing BIM SAHB$_{A2}$ and $^{1}$H-$^{15}$N-BAX revealed chemical shifts of a discrete subset of BAX residues, including Glu17, Met20, Lys21, Thr22, Ala24, Leu25, Leu27, Gln28, Gly29, Ile31, Gln 32, Asp 33, of alpha-helix 1, and Pro130, Glu131, Ile 133, Arg 134, Thr135, Met137, Gly138, Trp139, Leu141, Asp142, Phe143, Arg145, Glu146, Arg 147 of alpha-helix 6. Significant changes were also observed for the side-chain $NH_2$ of Gln28, Gln32, and Gln52. $^1H$-$^{13}C$ correlation spectra of BAX in complex with BIM SAHB$_{42}$ were also performed and noticeable changes of the $^1H$-$^{13}C$ resonances were observed for the side-chains of hydrophobic residues localized to the same regions, including Leu27-$C^{\delta 1}$-$H_3$ and -$C^{\delta 2}$-$H_3$, Ile31-$C^{\delta 2}$-$H_3$, and Ile133-$C^{\delta 2}$-$H_3$. The residues described above colocalize at the intersection of alpha-helices 1 and 6 at the surface of BAX, forming a hydrophobic patch comprised of residues including Met20, Ala24, Leu25, Leu27, Gly29, Ile31, Leu47, Val50, Phe92, Phe93, Ile 133, Arg 134, Met137, Gly138, Trp139, Leu141, Phe143 surrounded by a perimeter of charged and hydrophilic residues including Glu17, Lys21, Thr22, Gln28, Gln 32, Asp 33, Asp48, Gln52, Asp53, Thr56, Arg89, Glu131, Arg 134, Thr135, Asp142, Arg145, Glu146, Arg147 (FIG. 3, 4a). In the BAX structure, the α1 and α6 helices are positioned adjacent to one another, and the residues listed above localize to a discrete site at the juxtaposition of these helices on one side of the protein structure (FIG. 3, 4b). No residues on the opposite face of the protein are affected by BIM SAHB titration under these conditions (FIG. 3, 4b). Thus, these structural data reveal a novel binding site that is distinct in location from the canonical BH3 binding site reported for anti-apoptotic proteins (Muchmore et al. *Nature* 381 (6580), 335-341 (1996); Sattler, M. et al. *Science* 275 (5302), 983-986 (1997).) (FIG. 4b).

To orient BIM SAHB at the BAX interaction site, we conducted paramagnetic relaxation enhancement (PRE) NMR experiments, which can be performed on a time-scale that is compatible with the lifespan of the complex under NMR conditions. $^1H$-$^{15}N$-BAX HSQC spectra were acquired with methane thiosulphonate (MTSL)-derivatized BIM SAHB compounds (FIG. 6a) in the oxidized state and then repeated after nitroxide reduction. Of note, the chemical shift perturbation maps of BAX in complex with BIM SAHB and the MTSL-labeled derivatives demonstrate consistent changes in BAX helices 1 and 6, and in the α1-α2 loop. Whereas the intensity of BAX α1 residues are predominantly reduced in the presence of oxidized C-terminal label, the intensity of BAX α6 residues are predominantly reduced in the presence of oxidized N-terminal label (FIG. 6b). As an example, BIM SAHB$_{(A164C\text{-}MTSL)}$ caused marked signal suppression of Ser16 (α1) but had essentially no effect on Asp142 (α6) (FIG. 6c, top panel), whereas BIM SAHB$_{(W147C\text{-}MTSL)}$ had no effect on Ser16 (α1) but reduced the Asp142 (α6) signal (FIG. 6c, bottom panel). Because the degree of PRE correlates with the distance between the nitroxide label and the affected BAX residues (Battiste, J. L. & Wagner, G. *Biochemistry* 39 (18), 5355-5365 (2000)), structure calculations using restraints derived from PRE and chemical shift perturbation data were performed to define the orientation of BIM SAHB at the novel BAX site. Indeed, the calculated structures converged to place BIM SAHB perpendicular to BAX helices α1 and α6, with the N- to C-terminus directionality disposed right to left (FIG. 6d), and defined the key interactions between BIM BH3 and BAX (FIG. 6e). Whereas hydrophobic residues Ile 148, Ala 149, Leu 152, Ile 155, Gly 156, and Phe 159 of BIM SAHB engage the BAX hydrophobic groove, charged and hydrophilic residues Arg 153, Arg 154, Asp 157, Glu 158, Asn 160, and Tyr 163 of BIM SAHB interact with complementary charged and hydrophilic residues on BAX.

In contrast to the stable inhibitory interactions of BIM BH3 with anti-apoptotic proteins, the BAX-activating interaction triggers a dynamic continuum of events that includes BAX conformational change and oligomerization. Of particular interest, NMR resonances of residues in the α1-α2 loop of BAX shifted significantly upon BIM SAHB binding. In monomeric BAX, the center of the loop weakly associates with residues Ile133 and Met 137 of the α6 helix (Suzuki & Tjandra, *Cell* 103 (4), 645-654 (2000)). Changes observed in the loop residues can readily be explained by the shift of the loop conformation into an open form upon BIM SAHB binding. Because loop displacement upon ligand engagement may initiate a conformational change of BAX, we investigated whether BIM SAHB binding could directly activate BAX in solution. We monitored both the conversion of BAX from monomer to oligomer by size-exclusion chromatography (SEC) and the exposure of its buried N-terminal residues using the 6A7 antibody, which selectively detects the conformational change associated with BAX activation (Hsu & Youle, *The Journal of biological chemistry* 272 (21), 13829-13834 (1997)). We find that BIM SAHB triggers dose-dependent oligomerization of BAX at room temperature, with complete conversion achieved using 4-fold molar excess BIM SAHB after only 15 minutes incubation (FIG. 12a). This BIM SAHB-induced oligomerization correlated with exposure of the N-terminal epitope of BAX as recognized by the 6A7 antibody (FIG. 12b). Thus, the transient stability of the BIM SAHB-BAX complex we observe by NMR correlates with the interaction-triggered BAX conformational change and oligomerization that we detect biochemically.

To confirm that the SEC-based detection of BIM SAHB-induced BAX oligomerization reflects functional activation of BAX for its release activity, we performed correlative liposomal and mitochondrial assays. In liposomal assays that explicitly explore the capacity of BIM SAHB to directly trigger functional BAX activation in the absence of other factors, the combination of BIM SAHB and BAX yielded dose-responsive liposomal release of entrapped FITC-dextran (FIG. 12c, top panel). The specificity of BIM SAHB activity was confirmed by abrogation of activity upon BIM SAHB R153D mutagenesis or by adding anti-apoptotic BCL-X$_L$ΔC (FIG. 12c, bottom panel) Likewise, in mitochondrial release assays that employed BAX/BAK doubly-deficient mouse liver mitochondria prepared from Alb-cre$^{pos}$Bax$^{flox/-}$Bak$^{-/-}$ mice, BIM SAHB induced dose-responsive BAX-mediated cytochrome c release (FIG. 12d). Thus, in four distinct in vitro assays that measure ligand-induced BAX activation, BIM SAHB directly and dose-responsively triggered BAX.

Figure 13C:
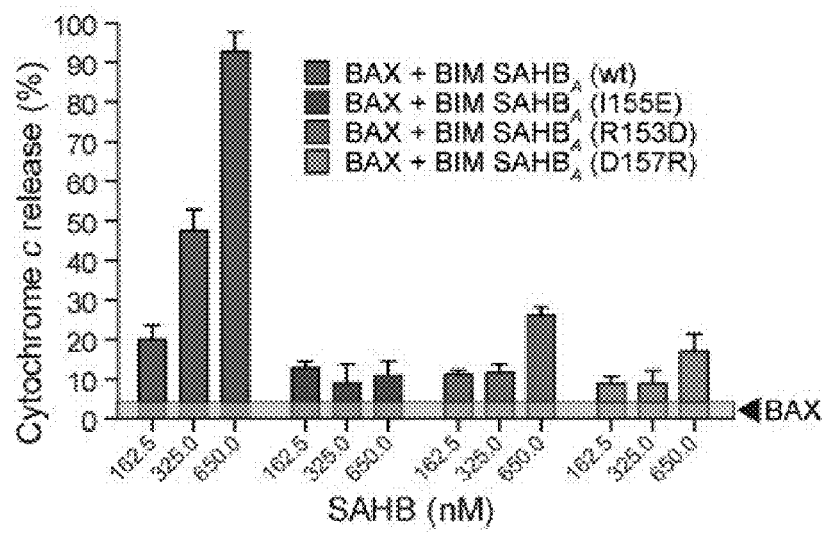
FIG. 13 Specificity of BIM SAHB-induced BAX activation: point mutagenesis. (a) A panel of BIM SAHB compounds mutated at its interaction surface with BAX (SEQ ID NOs: 35, 55, 61, and 63, respectively in order of appearance). Point mutagenesis of BIM SAHB abrogates its capacity to (b) oligomerize wild-type BAX and (c) trigger BAX-mediated cytochrome c release. (d) BAX K21E and R134E mutagenesis impairs BIM SAHB-induced BAX oligomerization.
Figure 13D:
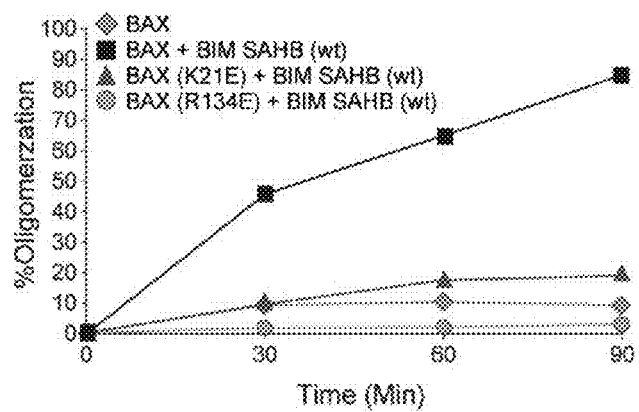

To confirm the specificity of the BIM SAHB interaction with BAX, several point mutations of the BIM BH3 SAHB binding surface were generated (FIG. 13a) and then tested for functional activation of BAX by performing an in vitro BAX oligomerization assay and mitochondrial cytochrome c release assay. In each case, reverse-polarity (R153D, D157R) and hydrophobic to charged (I155E) mutations along the interaction surface abrogated ligand-induced oligomerization of wild-type BAX (FIG. 13b) and BAX-mediated cytochrome c release (FIG. 13c). To validate the specificity of the BAX interaction site, BAX residues K21 and R134 were examined as they exhibited pronounced NMR chemical shifts upon BIM SAHB binding. Recombinant BAX bearing single reverse polarity mutations K21E and R134E were generated and then subjected to the BIM SAHB-induced BAX oligomerization assay, which revealed significant impairment of BIM SAHB-induced BAX K21E and BAX R134D activation (FIG. 13d). Taken together, these mutagenesis studies highlight the exquisite specificity of the BIM BH3-BAX interaction and implicate engagement of the novel binding site as a trigger mechanism for initiating BAX activation.

Figure 14A:
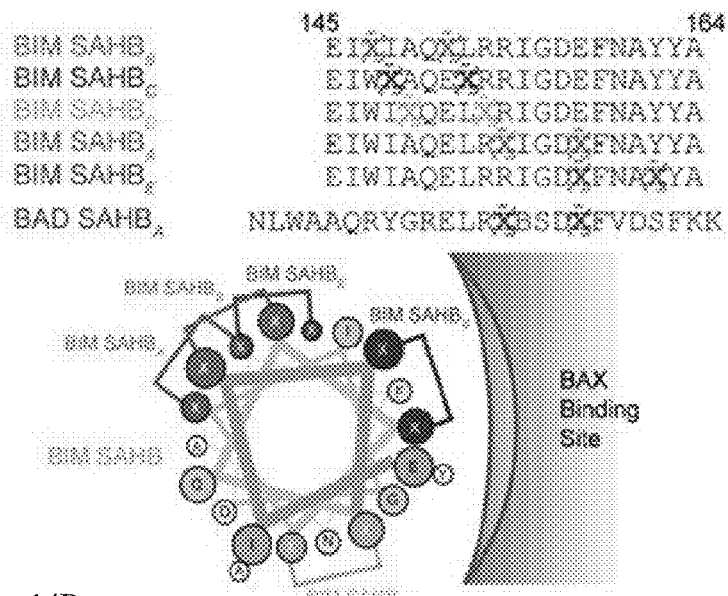
FIG. 14 Specificity of BIM SAHB-induced BAX activation: Staple Scan. A panel of BIM SAHB compounds with differential i, i+4 staple positions is used to demonstrate that only a staple that localizes to the hydrophobic interaction surface of BIM SAHB disrupts BAX oligomerization and BAX-mediated cytochrome c release. Selectivity is also underscored by the inability of BAD SAHBA, despite having the identical staple position as BIM SAHBA, to activate BAX (SEQ ID NOs: 69, 72, 74, 35, 76, and 149, respectively in order of appearance).
Figure 14B:
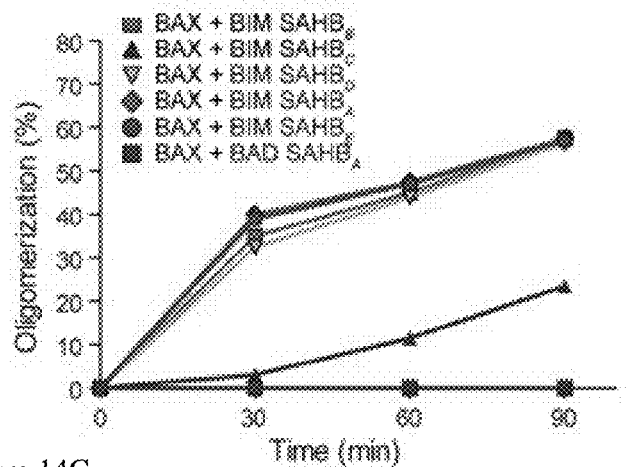
Figure 14C:
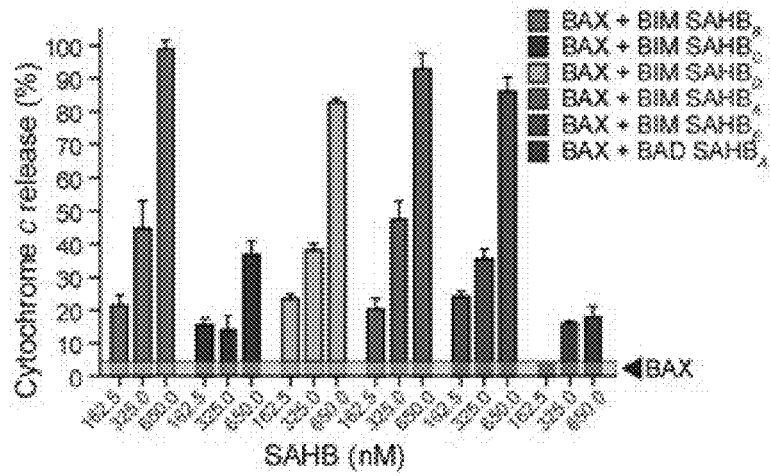
Figure 19:
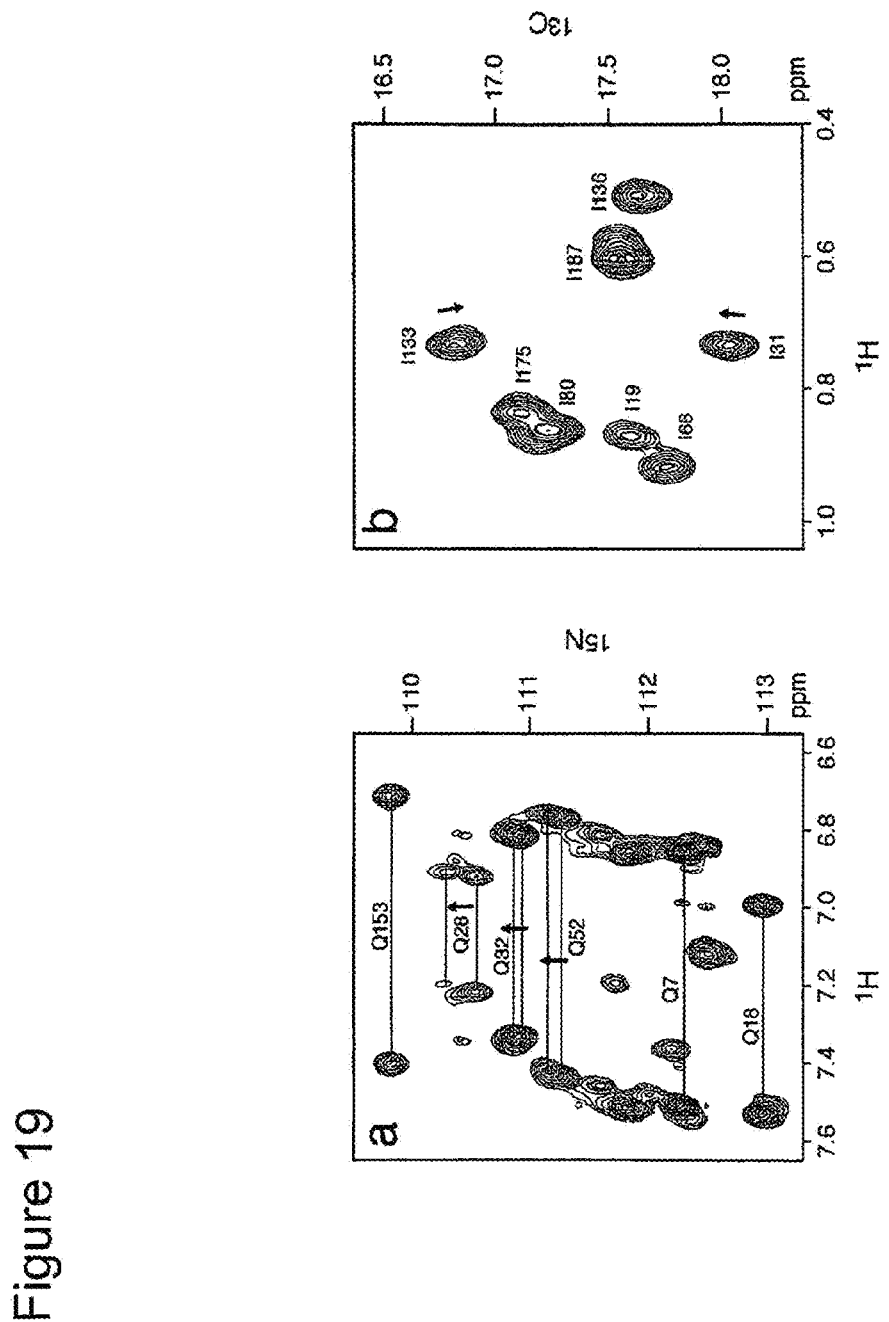
FIG. 19 NMR chemical shift changes of BAX side chains upon binding to BIM SAHB. The spectra of BAX are colored red and blue in the absence and presence of equimolar BIM SAHB, respectively. (a) A subset of the $^1$H-$^{15}$N HSQC spectra showing cross peaks for the NH$_2$ side chains of Glutamines. Significant differences can be observed for Gln28, Gln32, and Gln52. (b) A region of C$_{\gamma 2}$ methyl group of Isoleucines of the $^1$H-$^{13}$C CT-HSQC spectra. Noticeable changes are found for Ile31-C$^{\gamma 2}$-H$_3$ and Ile133-C$^{\gamma 2}$-H$_3$.

We next performed a "staple scan" to demonstrate and link the specificity of BIM SAHB-induced BAX activation to interaction at the novel site. By performing a staple scan that effectively replaces pairs of amino acid residues within the core BH3 sequence with crosslinked norleucine-like side chains, we simultaneously address which residues are essential to the functional interaction between BIM BH3 and BAX, and further confirm which surface along the BIM BH3 helix is essential to BAX engagement (FIG. 14a). Substituting the non-natural amino acid at positions W147, A149, E151, R153, R154, E158, or Y162 did not disrupt BIM SAHB-induced BAX oligomerization (FIG. 14b) or BAX-mediated cytochrome c release (FIG. 14c,d). Indeed, hydrocarbon staples located along the length of the helix at surfaces that do not face the hydrophobic contact site on BAX did not disrupt the functional interactions between the BIM SAHB analogs and BAX. However, a staple position that replaced I148 and the highly conserved L152, and localizes to the hydrophobic contact surface for BAX on the BIM BH3 helix (FIG. 14a), markedly decreased BAX oligomerization (FIG. 14b) and BAX-mediated cytochrome c release (FIG. 14c,d), findings consistent with the near abrogation of BIM SAHB-induced chemical shift perturbations of $^{15}$N-BAX by BIM SAHB$_c$. In addition, BAD SAHB$_A$, which has the identical staple position as BIM SAHB$_A$ but otherwise contains distinct amino acid sequence, did not bind or oligomerize (FIG. 14b) BAX, or induce BAX-mediated cytochrome c release (FIG. 14c,d).

To further examine the impact of BAX K21E mutagenesis at the α1-α6 interaction site, we demonstrated that the reduction of BIM SAHB-induced BAX$_{K21E}$ activation measured by the oligomerization assay (FIG. 13d,15a) was also reflected in blunted BAX$_{K21E}$-mediated cytochrome c release in response to BIM SAHB (FIG. 15b). To determine if this single point mutation within the novel BAX binding site impacted the capacity to activate BAX in a cellular context, we retrovirally reconstituted Bax$^{-/-}$Bak$^{-/-}$ mouse embryo fibroblasts (DKO MEFs) with either wild type or BAX$_{K21E}$ and monitored apoptosis induction in response to BIM SAHB. Whereas BIM SAHB induced time-dependent apoptosis of BAX-reconstituted MEFs, as quantitated by annexin-V binding, single K21E point mutation within the new BAX binding site reduced BIM SAHB-triggered apoptosis (FIG. 15c). This decrease in BAX$_{K21E}$-mediated apoptosis correlates with impaired activation of BAX$_{K12E}$ by BIM SAHB in both oligomerization and cytochrome c release assays (FIG. 15a, 15b). As a further measure of specificity, we found that R153D mutagenesis of BIM SAHB, which eliminated its BAX activating capacity in the liposomal, BAX oligomerization, and cytochrome c release assays (FIG. 12c bottom panel, 13b, 13c respectively), likewise abolished BIM SAHB-induced activation of BAX and BAX$_{K21E}$ in a cellular context (FIG. 15c).

To probe the broader physiologic impact of the novel BAX activation site, we examined the apoptotic response of DKO MEFs reconstituted with BAX and BAX$_{K21E}$ to staurosporine (STS), a general stimulus known to operate through endogenous BH3-only proteins, including BIM. K21E mutagenesis impaired STS-induced apoptosis, as monitored by annexin V binding over time (FIG. 15d). The reduced activity of BAX$_{K21E}$ was also reflected by impaired cytochrome c release, as detected by subcellular fractionation Western analysis and indirect immunofluorescence. The blunted response of BAX$_{K21E}$-reconstituted DKO MEFs to STS is uniformly consistent with impaired activation of BAX$_{K21E}$ by BIM SAHB in oligomerization (FIG. 15a), cytochrome c release (FIG. 15b), and cell-based apoptosis assays (FIG. 15c). Thus, the MEF studies extend the mechanistic relevance of direct BAX activation to a cellular context in which BAX-mediated apoptosis is impaired by single amino acid mutagenesis at the novel BH3 interaction site. Taken together, the in vitro and cell-based mutagenesis experiments highlight the exquisite specificity of the BIM BH3-BAX interaction and implicate engagement of the novel binding site as a trigger mechanism for initiating BAX activation.

To determine if BIM SAHB specifically targets BAX in cells, fluorescein isothiocyanate (FITC) derivatized analogs of the cell permeable BIM SAHB$_{A1}$ compounds were applied to Jurkat T-cells and cellular uptake by FACS analysis was recorded. Whereas BIM SAHB$_{A1}$ induced dose-dependent apoptosis induction in Jurkat T-cells by 18 hours incubation, BIM SAHB$_{A1}$ (R153D) had no effect. To document that BIM SAHB interacts with cytosolic BAX, Jurkat T-cells were incubated with FITC-BIM SAHB$_{A1}$ compounds for 4 hours, followed by cellular lysis in 1% CHAPS, and SAHB immunoprecipitation with anti-FITC antibodies. Indeed, FITC-BIM SAHB$_{A1}$ was capable of co-immunoprecipitating BAX from the cytosol of Jurkat T-cells. Thus, BIM SAHB can penetrate intact cells and specifically engage cytosolic BAX in cells stimulated to undergo apoptosis.

Example 2

Determining High Resolution Solution Structures of BOK and BAK Using (NMR) Spectroscopy Although the present invention is based, in part, on the identification of an active binding site in BAX, it is contemplated that corresponding active binding sites are present in other BCL-2 family polypeptides, given their overall high three-dimensional structural conservation. These non-BAX BCL-2 family polypeptide active sites that correspond to the BAX active site can be identified by amino acid sequence alignments between BAX and the test polypeptide, by structural comparison, or by a combination thereof. Such methods are known by those having ordinary skill in the art and are described herein. The invention provides methods for identifying homologous active sites in non-BAX BCL-2 family and non-BCL-2 family members via direct covalent intercalation of photoactivatable and crosslinkable derivatives of BH3 peptides or their mimetics to the target site, followed by intercalation site identification by, for example, proteolysis, fragment purification, and mass spectrometry based analysis. To directly identify sites in BCL-2 polypeptides whose structures have not been solved, the present invention contemplates generating high resolution solution structures of other BCL-2 family polypeptides including BOK and BAK and BCL-X$_L$. Such structures can be determined by the method described below.

Full length human BOK and BAK cDNAs can be subcloned into the pTYB1 vector to generate chitin-binding fusion proteins, followed by chitin affinity chromatography, DTT-based chitin cleavage, and gel filtration FPLC purification. Transformed *Escherichia coli* BL21 (DE3) cells are then grown at 37° C. and induced with 1 mM IPTG in either LB media (for unlabeled protein) or M9-minimal media substituted with $^{15}$N—NH$_4$Cl (1 g/l) with or without $^{13}$C-glucose (2 g/l) to obtain uniformly $^{15}$N-labeled protein or $^{15}$N, $^{13}$C-labeled protein, respectively. Deuterated, uniformly $^{15}$N$^{13}$C-labeled proteins can be prepared by growing the cells in 75% D$_2$O supplemented with $^{15}$N—NH$_4$Cl and $^{13}$C-glucose. NMR samples (0.5-1 mM) are then prepared in a 10 mM sodium phosphate buffer (pH 6.5) in D$_2$O or H$_2$O/D$_2$O (9:1).

NMR spectra are recorded at 25° C. on a Bruker Avance 600 MHz, 700 MHz, or 800 MHz spectrometers equipped with a z-shielded gradient and triple resonance cryoprobe. Chemical shift assignments are performed using standard techniques. For backbone assignments of $^1$H, $^{13}$C, $^{15}$N resonances, the following triple resonance 3D experiments are recorded: HNCO, HNCACO, HNCA, HNCOCA, HNCACB and CBCA(CO)NH on uniformly $^{15}$N, $^{13}$C labeled protein in H$_2$O. Side chain assignments are performed using the following standard 3D experiments: $^1$H-$^{15}$N TOCSY-HSQC, C(CO)NH-TOCSY, H(CCO)NH-TOCSY and HCCH-TOCSY. Any ambiguous assignments can be further confirmed by analysis of the 3D $^{13}$C-resolved [$^1$H-$^1$H] NOESY experiments on uniformly $^{15}$N, $^{13}$C-labeled protein in D$_2$O. Aromatic sidechain $^1$H and $^{13}$C resonances are assigned by the combination of 2D HMQC and 3D $^{13}$C-resolved [$^1$H-$^1$H] NOESY. Structural restraints are derived from $^{13}$C-resolved (100 or 120 ms mixing times) and $^{15}$N-resolved (120 ms mixing time) [$^1$H-$^1$H] NOESY experiments.

NMR data sets are processed with the NMRPipe (Delaglio, et al. (1995) NMRPipe *J Biomol NMR* 6(3), 277-293). spectral analysis and NMRView (Johnson, B. A. (2004) *Methods Mol Biol* 278, 313-352) software packages. Backbone φ and ψ torsion angle restraints are computed from $^{13}$C$_{\alpha\beta}$ chemical shifts using the program TALOS (Cornilescu, G., et al. (1999) *J Biomol NMR* 13(3), 289-302). 3J$_{HNH\alpha}$ coupling constants are measured from HMQC-J experiments as previously described (Kuboniwa, H. et al. (1994) *J Biomol NMR* 4(6), 871-878). Residual dipolar couplings (RDCs) are measured in the NMR sample buffer to which the filamentous phage Pf1 is added (Bax, A., Kontaxis, et al. (2001) *Methods Enzymol* 339, 127-174). NOE assignments are performed in automated mode with the CANDID module of the program CYANA 2.1.4 (Guntert, P. (2004) *Methods Mol Biol* 278, 353-378). Initial assignments are augmented by iterative rounds of manual and automated NOE assignment within CYANA and NMRView. Upon assignment of 99% of observable NOEs, structures from CYANA are further refined with Xplor-NIH 2.12, employing IVM dynamics adapted to incorporate pseudo-potentials for 3J$_{NH}\Delta$ coupling constants, secondary $^{13}$C$_{\alpha\beta}$ chemical shifts, and a conformational database potential for dihedral angles (Schwieters, et al. (2003) *J Magn Reson* 160(1), 65-73). Hydrogen bond distance restraints are incorporated for helical regions based on analysis of $^{13}$C$_{\alpha\beta}$ secondary chemical shifts and characteristic HΔ (i)-NH (i+3, i+4) NOEs. The 100 lowest energy structures having the best agreement with experimental restraints are subsequently refined in explicit solvent (Spronk, C. A., et al. (2002) *J Biomol NMR* 22(3), 281-289) to improve the local geometry, electrostatics, and packing quality of the protein. The final structure family is comprised of the 25 structures with the lowest energies for experimental restraints and the best overall values for chirality and stereochemistry measured with the programs WHATCHECK (Hooft, R. W., et al. (1996) *Nature* 381(6580), 272) and PROCHECK-NMR (Laskowski, R. A., et al. (1996) *J Biomol NMR* 8(4), 477-486).(2002) Palo Alto, Calif., USA PYMOL (DeLano, W. L. D. S., (2002) The PyMOL Molecular Graphics System. Palo Alto, Calif., USA) and MOLMOL (Koradi, R. et al. (1996) *J Mol Graph* 14(1), 51-55, 29-32).

Example 3

Define and Compare the Structural Basis for Modulator Interactions with BAX/BAK/BOK, and Induced Conformational Changes, by NMR Spectroscopy Additional, binding interactions between BH3 polypeptides and mimetics thereof and various BCL-2 family polypeptides are contemplated with the present invention.

The present below method may also be adapted for assaying and optimizing binding interactions of BH3 polypeptides and mimetic chemical compounds with BCL-2 family polypeptides.

The expression and purification of $^1$H, $^{15}$N-BAX/BAK/BOK proteins can be performed as described in Example 2. For NMR titrations, 1:1 complexes of BAX/BAK/BOK and SAHBs are generated by gradually increasing SAHB concentrations up to 0.5 mM in a 20 mM sodium phosphate buffer (pH 7.0) in D$_2$O or H$_2$O/D$_2$O (9:1). To identify a SAHB interaction site, the chemical shift perturbations of backbone amides upon addition of SAHB peptide are followed on a series of $^1$H-$^{15}$N HSQCs and data sets processed and chemical shifts measured with NMRPipe spectral analysis and NMRview software packages, respectively. To define an overall conformational change of BAX/BAK/BOK, backbone amides can be monitored and chemical shift assignments performed as described in Example 2. To facilitate the structure calculations for SAHB complexes, $^1$H-NMR 2D TOCSY and NOESY experiments provide solution structures for individual SAHB compounds that induce chemical shifts in BAX/BAK/BOK. Intermolecular NOEs are obtained from NOESY and 3D $^{13}$C-edited, $^{12}$C-selected NOESY experiments performed on a sample of uniformly $^{15}$N, $^{13}$C-labeled BAX/BAK/BOK bound to unlabeled SAHB. In addition, distance information for structural refinement of BAX/BAK/BOK-SAHB complexes will be derived from HSQC experiments performed using SAHBs derivatized with lanthanide-DOTA chelates positioned at selected sites (Vlasie, M. D. et al. (2007) *Chemistry* 13(6), 1715-1723) (Battiste, J. L. et al. (2000) *Biochemistry* 39(18), 5355-5365) or using MTSL-labeled SAHBs as described in Example 1 and demonstrated in FIG. 6.

For example, the DOTA chelate attached to SAHB, upon lanthanide activation, enhances relaxation and line broadening of nearby $^1$H-NMR resonances of BAX/BAK/BOK protein in a distance-dependent manner up to 25 Å. Paramagnetic relaxation enhancement (PRE) measurements are translated to distance restraints as previously described (Battiste, J. L., et al. (2000) *Biochemistry* 39(18), 5355-5365). Structure calculations of the SAHB-protein complexes are performed as described in Examples 1 and 2. If the binding of SAHB results in no detectable intermolecular NOEs, the structural models can be computed using HADDOCK v2.0 (Dominguez, C. et al. (2003) *J Am Chem Soc* 125(7), 1731-1737) with the default parameters and a set of unambiguous and ambiguous restraints determined from $^{15}$N HSQC NMR studies.

Initially, 500 structures of the complex are generated by rigid body docking of the individual structures. 100 of the lowest energy structures are subsequently refined in a semi-flexible simulated annealing followed by a fully flexible refinement in explicit solvent. The 20 lowest energy structures resulting from refinement of the family in explicit solvent are analyzed with HADDOCK internal scripts for analysis of several quality factors such as restraint violations, number of hydrogen bonds, hydrophobic contacts, root mean square deviation at the interface, and the total energy over the flexible interface of the BAX/BAK/BOK-SAHB interaction.

To determine changes in the motion of specific BAX/BAK/BOK structural regions upon SAHB binding, relaxation analysis is performed by measuring T1, T2 and $^1$H-$^{15}$N heteronuclear NOE data as previously described (Farrow, N. A. et al. (1994) *Biochemistry* 33(19), 5984-6003). T1 longitudinal recovery delays are set to 11, 65, 150, 246, 363, 523, 758 and 1142 ms. T2 transverse recovery delays are set to 21.6, 43.2, 64.8, 86.4, 108.0, 151.1, 194.3 and 237.5 ms, respectively. The repetition rate of the CPMG sequence is set to 550 μs. The $^1$H-$^{15}$N NOE is collected using a $^1$H saturation time of 3s. In each case, the error is determined as the standard deviation of two (T1, T2 and NOE) experiments. The data can be analyzed using the software package NMRView (Johnson, B. A. (2004) *Methods Mol Biol* 278, 313-352).

The methodology described above can likewise be applied to analyze the structural basis of novel modulator interactions with anti-apoptotic proteins, such as BCL-2 and BCL-X$_L$.

Example 4

Refining the Binding Affinities and Selectivities of Compounds for BAX/BAK/BOK Based Upon the Structural Insights Comparative analysis of the side chain interactions of SAHB ligands with BAX/BAK/BOK will enable the design of further natural and non-natural amino acid modifications into SAHB compounds to enhance binding affinities and evolve compound selectivities. Such structure-activity relationships by NMR methodology (Shuker, S. B. et al. (1996) *Science* 274(5292), 1531-1534) has successfully facilitated the development of small molecules that discern among discrete subgroups of anti-apoptotic proteins (Oltersdorf, T. et al. (2005) *Nature* 435(7042), 677-681) Bruncko, M. et al. (2007) *J Med Chem* 50(4), 641-662) Wendt, M. D. et al. (2006) *J Med Chem* 49(3), 1165-1181). Computer modeling and docking strategies, as described above in Example 3, will be used to simulate the substitution of discrete natural and/or non-natural residues into SAHB compounds to identify opportunities to engage additional favorable contact points at the interaction surface. Conversely, distinguishing complementary interactions may be disrupted in order to engineer a desired specificity profile into the SAHB compound. SAHBs, designed based upon these structural analyses, are synthesized and iterated through the battery of experiments outlined in the proceeding examples in order to achieve and validate the compound refinements.

Example 5

Generation, Structural Characterization, and Functional Evaluation of Activators/Inhibitors of BCL-2 Family Polypeptide Oligomers The active forms of BAX/BAK/BOK and other BCL-2 family polypeptides are believed to involve hetero- and homo-dimerization-based higher order structures. For example, BAX and BAK oligomers have been identified within the mitochondrial membrane and are believed to participate in pore formation that releases essential apoptogenic factors from the mitochondria. Because the SAHBs described herein, activate BAX to form such higher order and functional oligomers, SAHBs can be used to generate such structures in solution or through crystallization in order to generate and structurally characterize the oligomer. Because the oligomer is functionally required to induce mitochondrial apoptosis, activation or inhibition of such oligomeric pores would be therapeutically beneficial. By adding SAHB compounds to BCL-2 family polypeptides, such as BAX, over a gradient of ligand ratios and using a variety of salt and other conditions known in the art, distinct BAX conformers and oligomers can be generated and stabilized for NMR analyses (as described herein), or using X-ray crystallographic methods known in the art. For example, using 0.5:1-4:1 BIM SAHB:BAX solutions, high purify BAX oligomer has been generated and isolated in high purity. Functional activation or inhibition of BAX or other BCL-2 family polypeptides can be assayed using a size-exclusion chromatograpy-based monitoring of monomer-oligomer states (FIG. 12a) as described below, 6A7 antibody mediated recognition of activated BAX (FIG. 12b) as described below, liposomal assay (FIG. 12c) as described below and previously reported (Walensky et al. *Mol Cell* 24 (2), 199-210 (2006)), the monitoring of current passing through pores generated by BCL-2 family polypeptides on a lipid monolayer (ref. VDAC and Bax ex, J Biol Chem 2000, 275 (16) 12321; Bax and Bcl-2 ex, Science 1997, 277, pg. 370), or mitochondrial cytochrome c release (FIG. 12d,13c) as described below and previously reported (Walensky et al. *Mol Cell* 24 (2), 199-210 (2006)). Alternatively, the structural data can be used to design or screen for molecules, as described above and known to the art, that would enhance or block oligomerization and/or pore activity, and thereby modulate apoptosis through direct regulation of the BCL-2 family polypeptide oligomeric pore formation itself. For example, generating SAHB analogs that (a) target the novel activation site with too high affinity (e.g. myristoyl derivatives) or that (b) combines this binding interaction with an added moiety that blocks BAX conformational change or blocks the BAX homo-oligomerization site, or that (c) utilizes an activation site binder in combined treatment with a distinct oligomerization site binder SAHB, such as SAHBs modeled after the BAX α-helix 9 (FIG. 16b) which binds to the hydrophobic groove formed by the confluence of BAX BH domains 1, 2, and 3, would interfere with the BAX activation process and thereby inhibit BAX-mediated mitochondrial apoptosis for therapeutic benefit. The methods to evaluate such individual and combined treatments include the SEC-based, liposomal, cytochrome c release, and lipid monolayer current monitoring assays indicated above. Indeed, a myristoylated BID SAHB compound binds BAX with higher affinity than the unmyristolated compound and retains a similar degree of α-helical content, blocks BID SAHB-triggered BAX oligomerization and BAX-mediated cytochrome c release.

The myristoylated derivatives were made by capping the peptide amino terminus with myristic acid using standard coupling conditions.

Example 6

Evaluation of the Compounds' Ability to Activate or Inhibit Apoptosis

Activation of the BCL-2 family pro-apoptotic polypeptides causes mitochondrial outer membrane permeabilization (MOMP) and the release of key apoptogenic proteins, including cytochrome c and Smac/Diablo, which lead to terminal caspase activation (Green, D. R. (2005) *Cell* 121(5), 671-674). The below assays can be used for assaying the ability of the various active site binding compounds, or resultant BCL-2 polypeptide oligomers, to modulate apoptosis.

Mitochondrial Release Assay: In order to test activation/inhibition of a BCL-2 family polypeptide interactions on mitochondrial apoptosis induction, a cytochrome c release assay is used that employs mouse liver mitochondria from Bak$^{-/-}$ mice or Alb-cre$^{pos}$Bax$^{flox/-}$Bak$^{-/-}$ mice, added recombinant BCL-2 family polypeptide, e.g., BAX, BAK, or BOK (50 nM) with or without increasing doses of SAHBs (50-500 nM), and an ELISA-based read-out of cytochrome c. Negative controls include recombinant protein alone, compounds alone, vehicle treatment, point mutant SAHBs, and blockade using anti-apoptotic proteins, such as BCL-X$_L$ ΔC.

A BAK chimera in which the C-terminus is replaced with that of the more soluble BAX C-terminus is also contemplated. In yet another embodiment, mitochondrial studies to assess BAK activation are performed on wild type mouse liver mitochondria that contain endogenous BAK but lack BAX and BOK. In another aspect, mitochondrial studies to assess BOK activation are performed using recombinant BOK or mouse mitochondria that contain endogenous BOK, but lack BAX and BAK (i.e. using BAX/BAK-null mitochondria from Alb-cre$^{pos}$Bax$^{flox/-}$Bak$^{-/-}$ mice).

Liposomal Release Assay: Another assay that can be used to determine modulation of the BCL-2 family polypeptide is a liposomal release assay that simulates the mitochondria but only includes the essential components for BAX/BAK/BOK-induced release. Liposomes duplicating the lipid composition of the mitochondrial outer-membrane contact sites (OMCT vesicles) (Ardail, D. et al. (1990) Biol Chem 265(31), 18797-18802) (Lutter, M. et al. (2000) Nat Cell Biol 2(10), 754-761, are made using a mixture of 1-palmitoyl-2-oleoyl-sn-glycero-3-phosphocholine (POPC), 1-palmitoyl-2-oleoyl-sn-glycero-3-phosphoethanolamine (POPE), beef liver phosphatidylinositol (PI), cholesterol, and cardiolipin (Avanti Polar Lipids) at a weight ratio of 41:22:9:8:20, as previously described (Oh, K. J. et al. (2005) Biol Chem 280(1), 753-767). Large unilamellar vesicles (LUVs) with a diameter of 100 nm are prepared by the extrusion method (Szoka, F. et al. (1980) Biochim Biophys Acta 601(3), 559-571) in 20 mM HEPES, 150 mM KCl, pH 7, entrapped with FITC-labeled dextran-10 kD (Sigma), and purified by gel filtration as described (Oh, K. (2005) J Biol Chem 280(1), 753-767). Lipid concentration is determined by measuring vesicular phosphate content (Böttcher, C. J. F. et al. (1961) Anal Chim Acta 24, 203-204). The fluorescence dequenching assay is adapted from previous reports (Kuwana, T. et al. (2002) Cell 111(3), 331-342) (Terrones, O., et al. (2004) J Biol Chem 279(29), 30081-30091). The release of FITC-labeled dextran-10 kD from LUVs is monitored using a FluoroMax-2 spectrofluorometer (SPEX), in a thermostated 1 cm path length quartz cuvette with constant stirring at 37° C. Excitation and emission wavelengths are 488 and 525 nm, respectively (slits, 2 nm). The extent of fluorescent marker release is quantified on a percentage basis according to the equation: $[(F_t-F_0)/(F_{100}-F_0) \times 100]$, where $F_t$ is the measured fluorescence of reagent-treated LUV at time t, $F_0$ is the average fluorescence of the LUV suspension for the initial 1-2 min before reagent addition, and $F_{100}$ is the average fluorescence value of the final 1-2 min after complete disruption of LUVs by addition of Triton X-100 (final concentration, 0.66 mM). Experiments are performed using a lipid concentration of 10 µg/ml, 15 nM BAX/BAK/BOK, 25-200 nM SAHBs singly or in combination, and BCL-$X_L$ ΔC or other anti-apoptotic blockade (100-800 nM).

Oligomerization assay: BIM SAHB was added to a 200 µL solution (20 mM Hepes/KOH pH 7.2-7.4, 150 mM KCl) containing monomeric BAX (38 µM) at a ratio of 0.5:1, 1:1, 2:1 and 4:1 BIM SAHB:BAX. The mixtures and a sample of BAX monomer alone were incubated at 22° for 15 minutes and then subjected to analysis by size exclusion chromatography (SEC) using an SD75 column. The chromatogram demonstrates the monomeric and oligomeric peaks at ~11.5 min and ~6.5 min, respectively. Protein standards (GE Healthcare) were used to calibrate the molecular weights of gel filtration peaks. For time-dependent analysis, BIM SAHB was added to monomeric BAX at a ratio of 1:1, and the mixtures were analyzed by SEC after incubation for 30, 60, and 90 minutes at 22° C. As a baseline for comparison, Bax monomer alone was analyzed at time 0 and the above time points.

Conformational change assay: BIM SAHB was added to a 20µL PBS solution containing monomeric BAX (9 µM) at a ratio of 0.5:1, 1:1,2:1 and 4:1 BIM SAHB:BAX. The mixtures (10 µL) and a BAX monomer sample (10 µL) were incubated at 22° for 15 minutes and then added to a 3% BSA in PBS solution (250 µL) containing 15 µL of 6A7 anti-BAX antibody for 1 hour incubation at 4° C. Additionally, 1 µL of each input sample (10%) was mixed with 50 µL of SDS-sample buffer to measure baseline BAX levels across specimens. Preclarified SEPHAROSE® beads (50 µL) were added to the BIM SAHB:BAX and BAX monomer solutions for an additional 2 hour incubation at 4° C. The SEPHAROSE® beads were spun down, washed 3 times with 1 mL of 3% BSA in PBS solution, resuspended in 50 µL of SDS-sample buffer and boiled at 95° C. for 2 minutes. Ten microliters each of inputs and immunoprecipitation samples were used for analysis. Samples were separated on 12% SDS-PAGE Bis-Tris gel, blotted on a PVDF membrane, and Western analysis performed using the rabbit polyclonal N20 anti-BAX antibody (Santa Cruz Biotechnology) and chemiluminescence-based detection (PerkinElmer).

Cell-based apoptosis studies: Yet another approach for determining BCL-2 family polypeptide modulation is cell based studies. Compounds are screened against a panel of tumor cell lines representing multiple myeloma, leukemia, lymphoma, sarcoma, retinoblastoma, and cancers of the breast, prostate, colon, lung, kidney, thyroid, and adrenal gland. Many such cell lines have been characterized by DNA microarray expression profiling (Mitsiades, C. S. et al. (2004) Cancer Cell 5(3), 221-230). Tumor cells in their appropriate media are plated in 96 well format and exposed to serial dilutions of compounds. The effect of compound treatment on cancer cell viability is measured at 12-48 hours by MTT assay, performed according to the manufacturer's protocol (Roche) and quantitated by an ELISA microplate reader (Bio-rad). $IC_{50}$ values are determined by nonlinear regression analysis using Prism software (Graphpad). Compounds that display inhibitory activity in this assay are then evaluated for specific apoptosis induction over time in the corresponding cancer cell by annexin V binding and FACS analysis. Cultured cancer cells ($0.5-1\times10^5$) are incubated for 24 hours with compound at concentrations observed to be effective in MTT assays. Cells are then washed and stained with propidium iodide (0.5 µg/mL) and FITC-tagged annexin V according to the manufacturer's protocol (BD Biosciences). Apoptosis induction is quantified by FACS and the data analyzed using FlowJo software (Tree Star). To confirm that compounds are functioning via the genetic pathway of apoptosis, inactive SAHB analogues generated by point mutation are employed as negative controls. In addition, caspase inhibitors, such as caspase 3 inhibitor Z-DEVD-FMK (BD Biosciences), are employed to determine that SAHB-induced apoptosis is reversed by caspase inactivation. The goal of these cell-based studies is to match specific compounds with susceptible cancer cell lines as a basis for investigating the mechanistic contribution of direct engagement of BAX/BAK/BOK in reactivating cancer cell apoptosis.

Real-time physiologic read-outs of SAHB effects on compound-sensitive cancer cell lines could additionally include microscopic evaluation of mitochondrial morphology (Scorrano, L. et al. (2002) Dev Cell 2(1), 55-67) epifluorescence imaging of mitochondrial calcium uptake (Scorrano, L. et al. (2003) Science 300(5616), 135-139), measurement of changes in mitochondrial respiration and transmembrane potential (Li, H. et al. (1998) osis. Cell 94(4), 491-501) (Scorrano, L. et al. (2002) Dev Cell 2(1), 55-67), tracking the localization of intracellular cytochrome c by indirect immunofluorescence (Yin, X. et al. (1999) *Nature* 400(6747), 886-891), quantitation of cytochrome c release by cell fractionation and Western analysis (Kim, H. (2006), *Nat Cell Biol* 8, 1348-1358) and/or quantitation of effector caspase 3 activity using a fluorogenic substrate (Wei, M. C. et al. (2001) *Science* 292(5517), 727-730).

To confirm the identity of in situ targets of action of SAHB compounds, co-immunoprecipitation studies using extracts from FITC-SAHB treated cells can be performed. For example, treatment of Jurkat cells with FITC-BID SAHB followed by anti-FITC immunoprecipitation from extracts identified interacting proteins BID SAHB and BAX by Western analysis (Walensky et al. (2006) Mol Cell, 24, 199-210) and by mass spectrometry based identification of electrophoresed bands.

Example 7

Derivatization of SAHBs for Photo-Activatable Covalent Capture of Protein Targets In Vitro and In Situ SAHBs, such as BIM SAHB, were converted to selective crosslinking reagents that target BCL-2 polypeptides, such as BAX, at the novel and other active sites. Initially, a panel of FITC-BAD BH3 compounds containing benzophenone (Bpa) moieties at discrete locations were generated (FIG. 11). To determine if Bpa substitution disrupted apoptotic binding activity, the compounds were subjected to FPA studies using GST-BCL-$X_L$ ΔC and complete retention of high affinity binding activity across the panel was observed. The capacity for covalent crosslinking upon exposure to 350 nm light was tested in vitro using GST-BCL-$X_L$ ΔC and 2-fold molar excess FITC-BAD BH3$_{Bpa}$. A crosslinked adduct of the appropriate molecular weight as detected by Coommassie stain and by fluorescence gel imaging was observed. The covalent capture of GST-BCL-$X_L$ ΔC by the derivatized BH3 was time-dependent and achieved near saturation by 135 min. The correct mass of the FITC-BAD BH3$_{Bpa}$-GST-BCL-$X_L$ ΔC complex was confirmed by MALDI-MS analysis of the reaction mixture. The corresponding FITC-BAD SAHB$_{Bpa}$ compound was also generated, which also covalently trapped GST-BCL-$X_L$ ΔC but with strikingly more rapid kinetics than the unstapled FITC-BAD BH3$_{Bpa}$. Proteolysis of the crosslinked species followed by mass spectrometry-based analysis identified the amino acid sequence of the GST-BCL-$X_L$ ΔC fragment that was targeted by FITC-BAD SAHB$_{Bpa}$.

To access the novel active site, BIM, BID, and PUMA SAHBs were generated to contain photoactivatable crosslinkable moieties as described above (FIG. 11). Indeed, all BIM SAHB derivatizes generated targeted and covalently bound BAX upon 350 nm light exposure in a dose- and time-dependent fashion. In fact, the identification of a doublet species that migrated just above the BAX monomeric molecular weight, highlighted the existence of alternative binding modes, and resultant differences in BAX migration, upon exposure to these SAHB reagents. When the crosslinking experiment was performed with different ratios of BIM SAHB: BAX, the crosslinking and stabilization of a higher order BAX oligomer that contained the BIM SAHB compounds was captured, emphasizing the utility of these intercalating BIM SAHB derivatives to access the novel active site and also capture the physiologic oligomers of BAX that result from its activation.

In order to capture and define SAHB activities within cells, the derivatized SAHBs described above were applied to cultured cells and after timed incubation periods, subjected to irradiation with 350 nm light for up to one hour on ice, followed by cellular lysis and anti-FITC immunoprecipitation. Immunoprecipitates were electrophoresed and analyzed by Coommassie and silver staining, fluorescent gel imaging, and Western blotting for apoptotic proteins. To confirm the specificity of the findings, negative control experiments included (1) the corresponding FITC-SAHB compound that lacks Bpa incorporation, (2) non-irradiated samples, and (3) point mutant FITC-SAHB Bpa compounds. Specific and discrete electropheresed bands were excised and subjected to identification by mass spectrometry. Immunoprecipitates were electrophoresed and analyzed by Coommassie and silver staining, fluorescent gel imaging, and Western blotting for apoptotic and other proteins.

To achieve a covalent complex retrieval strategy beyond anti-FITC pull-downs, a multifunctional handle was chemically fused to SAHB compounds. The design included an initial capping of SAHBs with the alkyne-containing carboxylic acid, 4-pentynoic acid, for use in the cell treatment, in situ binding, and irradiation steps. Upon cellular lysis (subsequent to covalent capture), the N-terminal propargyl group of the crosslinked SAHB compound selectively undergoes cycloaddition with an azide-containing multifunctional linker in the presence of copper (i.e. "click chemistry") Saghatelian, A., et al. Proc Natl Acad Sci USA 101(27), 10000-10005 (2004); Rabuka, D., et al. J Am Chem Soc 128(37), 12078-12079 (2006); Speers, A. E., et al. J Am Chem Soc 125(16), 4686-4687 (2003); Speers, A. E., et al., Chem Biol 11(4), 535-546 (2004). In addition to the azide functionality, the linker was designed to contain a biotin moiety for streptavidin capture, a fluorophore for detection, and a protease recognition site for mild release of attached SAHB-protein complexes from the streptavidin beads for proteomic analysis (Adam, G. C., et al. Mol Cell Proteomics. 1(10), 828-835 (2002)). (FIG. 17). The released fluorophore-labeled SAHB-protein complex was analyzed by MALDI-MS and LC-MS techniques to determine the molecular mass, followed by digestion with trypsin or lysyl-endopeptidase to produce fragments for protein identification using high-resolution mass spectrometry. An added benefit of this method, which complements the structural approaches defined above, is the capability to identify the site of SAHB interaction on the target protein utilizing the fluorophore-labeled fragment for sequence determination by tandem mass spectrometry (MS-MS) or MSn analysis.

Thus, in order to maximally exploit apoptotic pathways to subvert cancer and other diseases, a careful dissection of how specific pro-apoptotic agents reactivate cell death in cancer is required. Because of the synthetic challenges associated with incorporating a covalent capture moiety into a small molecule, and the attendant risk of modifying the compound's activity as a result, in situ mechanisms of action are rarely defined for small molecules in an explicit manner. An important advantage of cell permeable SAHBs is their facile derivatization with a broad range of chemical functionalities. In generating multifunctional SAHBs for covalent capture, the intracellular targets of these apoptotic compounds are clearly defined, and thereby how specific BH3 death domains and their pathways can be harnessed to reactivate or inhibit apoptosis for therapeutic purposes can be determined.

In another alternative strategy for converting SAHBs into crosslinkable reagents in situ involves derivatizing the amino termini with a photo-labile carbene or nitrene-generating functionality. First, SAHBs were synthesized with amino terminal β-Ala linker sequences containing a biotinylated lysine residue for streptavidin affinity capture. The amino terminus was then capped via the carboxylate of p-[(3-trifluoromethyl)diazirine-3-yl] benzoic acid or the nitrene generating adduct 4-azido-2,3,5,6-tetrafluorobenzoic acid (Yan, M., et al. *Bioconjug Chem* 5(2), 151-157 (1994)) (FIG. 18). Cancer or other cells exposed to the photolabile SAHBs were treated with either 30W black light (for diazirine photolysis) or UV illumination (for azide photolysis), followed by incubation, cellular lysis, and streptavidin bead-based target capture of biotinylated SAHB-protein complexes. Control experiments were performed in parallel using SAHB point mutants known to abrogate binding activity. Eluted SAHB-protein complexes were resolved by denaturing gel electrophoresis and bands present in SAHB fractions, but not in SAHB point mutant lanes, subjected to protein identification by mass spectrometry analysis.

Example 8

SAHBs Restore Selective BH3-Based Pro-Apoptotic Activity in Mouse Models of Defective BAX/BAK/BOK Activation The knowledge gained from dissecting BAX/BAK/BOK regulation via the novel active site can be applied to develop targeted therapeutics for cancer and other diseases based on reactivating or inhibiting apoptosis through direct BAX/BAK/BOK engagement. To that end, SAHBs with potent and specific BAX/BAK/BOK-mediated pro-apoptotic activity, such as BIM SAHB, have undergone therapeutic efficacy testing in vivo. For example, reactivating apoptosis by "BH3 replacement" was tested.

To evaluate SAHB compound activity and selectivity, BH3 replacement was performed in disease models that were derived from the elimination of the corresponding BH3-only protein(s) that activate BAX/BAK/BOK. For example, the capacity of BIM SAHB to reactivate apoptosis in lymphoid infiltrates found in the organs of $Bim^{-/-}$ mice was tested. Age- and sex-matched pilot cohorts of $Bim^{-/-}$ and wild-type mice were either treated with vehicle (2.5% DMSO/D5W) or BIM SAHB (10 mg/kg) daily for five to seven days, followed by euthanasia, tissue harvest, histopathologic evaluation, and immunohistochemical workup. Well-defined B-lineage lymphoplasmacytic infiltrates of the kidney, lung, and liver were examined. Whereas the histology of vehicle- and BIM SAHB-treated wild type animals was normal in both groups, clear evidence of lymphoid infiltration was evident in the organs of $Bim^{-/-}$ mice. Strikingly, $Bim^{-/-}$ mice treated with BIM SAHB displayed marked influx of tingible-body macrophages in the lymphoid infiltrates. B220+ cell fragments were evident within the macrophages by immunohistochemistry and scattered cells throughout the infiltrate were positive for activated caspase-3; TUNEL-positivity was also observed. Organs from vehicle-treated $Bim^{-/-}$ mice lacked these findings, suggesting that BIM SAHB initiated apoptosis of the pathologic infiltrates within $Bim^{-/-}$ organs. To expand these studies, irradiated (450 cGy) female $Rag2^{-/-}$ gamma $(c)^{-/-}$ mice (10-12 wk) were reconstituted with $2 \times 10^6$ bone marrow cells from $Bim^{-/-}$ mice in order to generate large, uniform cohorts (n=10) for statistical analysis. The reconstituted animals develop the same autoimmune phenomena of the native $Bim^{-/-}$ mice, including the fatal glomerulosclerosis.

For example, the study design included five cohorts treated 12 weeks post-transplant with either vehicle, BIM SAHB (3, 10 mg/kg), or negative control SAHB (e.g. mutant BIM SAHB or a distinct SAHB such as BAD SAHB; 3, 10 mg/kg) daily for 7 days. On days 0, 4, and 7 of the study, complete blood count, FACS analysis of peripheral blood lymphocytes, serine BUN/Creatinine, and splenic and kidney ultrasound for organ volume and RF mode echogenicity measurements (Vevo 770, VisualSonics) were performed. On day 8, the animals were sacrificed for histopathologic and immunohistochemical analyses (e.g. TUNEL- and activated caspase-3-positive cells per high power field of renal infiltrates). Data on lymphocyte counts (CBC), lymphocyte subsets (FACS), renal function (BUN/Creatinine), spleen and kidney volume (ultrasound), and RF mode backscatter spectra (ultrasonic evidence of apoptosis) were inspected, and mathematically transformed if necessary to stabilize the variance across treatment groups. Repeated measures analysis of variance are used for the blood and imaging parameters measured on days 0, 4, and 7, and contrasts within the model will be used to assess changes from baseline between treatment groups. Histopathologic analysis of organ infiltrates, obtained for example on day 8 at sacrifice, are assessed between groups using the Kruskal-Wallis test for the three group comparison, and the Wilcoxon rank sum test for comparisons of the BIM SAHB-treated animals to controls. With 10 animals per group, the Wilcoxon rank sum test has 80% power to detect a 1 standard deviation difference between groups, testing at a one-sided significance level of 0.10.

Based on the comparative analyses of $Bim^{-/-}$ and $Bim^{-/-}$ $Bid^{-/-}$ phenotypes and their cellular apoptosis resistance profiles (MEFs, splenocytes, thymocytes), it is contemplated that combinatorial knock-out models will provide distinct disease backgrounds for evaluating the efficacy of BID, BIM, and PUMA SAHBs, singly and in combination. Additionally, in reconstitution studies using bone marrows from single and combination BH3-only genotypes, morphologically and immunophenotypically distinct lymphoproliferations were observed, which also serve as genotype-specific disease models for SAHB efficacy testing.

In yet another approach, SAHB efficacy testing can also be performed using mouse xenograft models corresponding to particular SAHB-sensitive cell lines. SAHB-sensitive cancer cell lines of interest would be retrovirally transduced to achieve stable luciferase expression (pMMP-LucNeo) as previously described (Armstrong, S. A., et al. *Cancer Cell* 3(2), 173-183 (2003)). To screen for successful transfer and growth of transplanted tumor, SCID beige mice (6-8 weeks old females, Jackson Laboratory) are subjected to 300 cGy total body irradiation (Gammacell 40, Atomic Energy of Canada, LTD) and 3 hours later injected with the cancer cells by tail vein (i.e. $0.5 \times 10^6$, $1.0 \times 10^6$, $2.5 \times 10^6$, or $5 \times 10^6$ injected cells). For alternate day in vivo tumor imaging, mice are anesthetized with inhaled isoflurane and treated concomitantly with intraperitoneal injection of D-luciferin (60 mg/kg). Photonic emission is imaged (2 min exposure) using the Xenogen In Vivo Imaging System and total body bioluminescence quantified by integration of photonic flux (photons/sec) using Xenogen's Living Image Software. The time course for cancer development is determined by monitoring for increasing bioluminescence and the diagnosis of cancer confirmed by necropsy of ill-appearing animals. The optimal cell dose to achieve a robust xenograft is determined for each chosen cell line. For these longitudinal studies of 4 cell doses, 7 animals would be studied per group. This experimental design assumes that the standard deviation of the mean luminescence levels between the dose groups is 70% of the standard deviation within the animals treated at a given dose level, thereby affording 80% power to determine there was indeed a difference in luminescence, testing at the overall 0.05 significance level. Statistical calculations for this experimental design were performed using nQueryAdvisor5.0.

Xenograft studies can examine 6 mouse cohorts (n=10), treated with either vehicle alone, low- or high dose SAHB (3-30 mg/kg), or low- or high dose SAHB mutant control. Starting on experimental day 1 (ln [total body luminescence] range of 14-16), mice receive a once daily tail vein injection and then imaged on alternate days to track tumor growth and survival daily for the duration of the experiment. With 10 animals per group, we have 80% power to distinguish between a control cohort in which 90% of the animals succumb to disease by a fixed time point, compared to 30% in a treated group, with testing at the 0.05 nominal significance level. The survival distributions of experimental mice are determined using the Kaplan-Meier method and compared using the log-rank test. The Fisher's exact test is used to compare the proportion of mice who fail treatment, where treatment failure is defined as progression or death, and success as stable disease or regression. Whole body necropsy with detailed histologic evaluation of the tumor sites of expired mice are performed. When a treatment response is observed with a particular SAHB, the experiment is repeated using 10-mice cohorts dosed at different levels, in order to evaluate dose-response to treatment. Two additional cohorts, treated with either vehicle or a therapeutic dose of SAHB, are used for pharmacodynamic studies in which pro-apoptotic activities are evaluated by euthanizing animals on specific treatment days and tumor tissue harvested for evaluation by TUNEL and activated caspase-3 immunohistochemical staining.

Example 9

Reactivating Apoptosis in Chemoresistant and/or Refractory Cancer or Other Diseased Cells Through Direct BAX/BAK/BOK Activation Many cancer cells and their relapsed/chemoresistant variants achieve cellular immortality by massively overexpressing anti-apoptotic members of the BCL-2 family. Using BH3 mimetics and small molecules, anti-apoptotic inhibition is one mode of overcoming apoptotic blockade. However, when BH3 mimetics or small molecules have a specificity profile that cannot target a specific anti-apoptotic blockade, such as MCL-1 overexpression (Van Delft et al, Cancer Cell. 2006 Nov.; 10(5):389-99; Konopleva et al, Cancer Cell. 2006 Nov.; 10(5):375-88; Deng et al Cancer Cell. 2007 Aug.; 12(2):171-85), direct BAX modulation can circumvent, or synergize with, such apoptotic blockade for therapeutic benefit. Indeed, BID and BIM SAHBs have the dual capability to directly bind and activate BAX/BAK and block anti-apoptotic targets, and are thus more potent than other BH3 mimetics, such as ABT-737 or BAD SAHB, in reactivating apoptosis of MCL-1 overexpressing or otherwise chemoresistant cancer cells. For example, the Pfeiffer lymphoma cell line which overexpresses MCL-1 and A1 is resistant to ABT-737, but is potently killed by BIM SAHB. Therefore, cancers or other diseased cells that either overexpress anti-apoptotic proteins such as MCL-1 and A1, or cancers or diseased cells that specifically down-regulate activator BH3-only proteins, like BIM, such as in Mantle Cell lymphoma (Tagawa et al Oncogene. 2005 Feb. 17; 24(8):1348-58; Mestre-Escorihuela, Blood. 2007 Jan. 1; 109(1):271-80) and cf. with mouse model of BIM-deletion, are ideally suited for BIM SAHB, or derivatives and mimetics thereof, to reactivate apoptosis through direct engagement of the novel BAX activation site and thereby induce apoptosis for therapeutic purposes and irrespective of the aforementioned apoptotic blockades.

What is claimed is:

1. A method of treating leukemia or lymphoma in a subject, comprising administering to said subject in need thereof, an effective amount of a BIM BH3 polypeptide consisting of at least 20 contiguous amino acids of SEQ ID NO: 3 wherein the side-chain of Arg at position 10 and the side-chain of Glu at position 14 of SEQ ID NO: 3 have been replaced by a cross-link, and a BAX polypeptide consisting of SEQ ID NO: 14, wherein the side-chain of Gly at position 11 and the side-chain of Ala at position 15 have been replaced by a cross-link, such that said subject is treated for leukemia or lymphoma.

2. The method of claim 1, wherein the BIM BH3polypeptide consists of SEQ ID NO: 3 wherein the side-chain of Arg at position 10 and the side-chain of Glu at position 14 of SEQ ID NO: 3 have been replaced by a cross-link.

* * * * *

SEQUENCE LISTING

```
<160> NUMBER OF SEQ ID NOS: 164

<210> SEQ ID NO 1
<211> LENGTH: 192
<212> TYPE: PRT
<213> ORGANISM: Homo sapiens

<400> SEQUENCE: 1

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125
```

```
Val Pro Glu Leu Ile Arg Thr Ile Met Gly Trp Thr Leu Asp Phe Leu
130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 2
<211> LENGTH: 138
<212> TYPE: PRT
<213> ORGANISM: Homo sapiens

<400> SEQUENCE: 2

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Asp Arg Ser Pro Ala Pro Met
        35                  40                  45

Ser Cys Asp Lys Ser Thr Gln Thr Pro Ser Pro Pro Cys Gln Ala Phe
    50                  55                  60

Asn His Tyr Leu Ser Ala Met Ala Ser Met Arg Gln Ala Glu Pro Ala
65                  70                  75                  80

Asp Met Arg Pro Glu Ile Trp Ile Ala Gln Glu Leu Arg Arg Ile Gly
                85                  90                  95

Asp Glu Phe Asn Ala Tyr Tyr Ala Arg Arg Val Phe Leu Asn Asn Tyr
            100                 105                 110

Gln Ala Ala Glu Asp His Pro Arg Met Val Ile Leu Arg Leu Leu Arg
        115                 120                 125

Tyr Ile Val Arg Leu Val Trp Arg Met His
    130                 135

<210> SEQ ID NO 3
<211> LENGTH: 22
<212> TYPE: PRT
<213> ORGANISM: Homo sapiens

<400> SEQUENCE: 3

Glu Ile Trp Ile Ala Gln Glu Leu Arg Arg Ile Gly Asp Glu Phe Asn
1               5                   10                  15

Ala Tyr Tyr Ala Arg Arg
            20

<210> SEQ ID NO 4
<211> LENGTH: 25
<212> TYPE: PRT
<213> ORGANISM: Homo sapiens

<400> SEQUENCE: 4

Glu Ser Gln Glu Asp Ile Ile Arg Asn Ile Ala Arg His Leu Ala Gln
1               5                   10                  15

Val Gly Asp Glu Met Asp Arg Ser Ile
            20                  25

<210> SEQ ID NO 5
<211> LENGTH: 24
<212> TYPE: PRT
```

<213> ORGANISM: Homo sapiens

<400> SEQUENCE: 5

Glu Gln Trp Ala Arg Glu Ile Gly Ala Gln Leu Arg Arg Met Ala Asp
1               5                   10                  15

Asp Leu Asn Ala Gln Tyr Glu Arg
            20

<210> SEQ ID NO 6
<211> LENGTH: 195
<212> TYPE: PRT
<213> ORGANISM: Homo sapiens

<400> SEQUENCE: 6

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Gly Met Asp
        195

<210> SEQ ID NO 7
<211> LENGTH: 193
<212> TYPE: PRT
<213> ORGANISM: Homo sapiens

<400> SEQUENCE: 7

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
            20                  25                  30

Ser Ala Val Ser Cys Gly Leu Cys Glu Pro Gly Leu Ala Ala Ala Pro
        35                  40                  45

Ala Ala Pro Thr Leu Leu Pro Ala Ala Tyr Leu Cys Ala Pro Thr Ala
    50                  55                  60

Pro Pro Ala Val Thr Ala Ala Leu Gly Gly Ser Arg Trp Pro Gly Gly
65                  70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110

Gly Ala Leu Ala Gly Gly Pro Thr Gln Ala Ala Pro Gly Val Arg Gly
        115                 120                 125

Glu Glu Glu Gln Trp Ala Arg Glu Ile Gly Ala Gln Leu Arg Arg Met
    130                 135                 140

Ala Asp Asp Leu Asn Ala Gln Tyr Glu Arg Arg Gln Glu Glu Gln
145                 150                 155                 160

Gln Arg His Arg Pro Ser Pro Trp Arg Val Leu Tyr Asn Leu Ile Met
                165                 170                 175

Gly Leu Leu Pro Leu Pro Arg Gly His Arg Ala Pro Glu Met Glu Pro
            180                 185                 190

Asn

<210> SEQ ID NO 8
<211> LENGTH: 239
<212> TYPE: PRT
<213> ORGANISM: Homo sapiens

<400> SEQUENCE: 8

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 9

```
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
            195

<210> SEQ ID NO 10
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Phe Gly Met Gly Ser Ala Gln Ala Cys Pro Cys Gln Val Pro
1               5                   10                  15

Arg Ala Ala Ser Thr Thr Trp Val Pro Cys Gln Ile Cys Gly Pro Gln
            20                  25                  30

Pro Ser Leu Ser Leu Ala Glu Gln His Leu Glu Ser Pro Val Pro Ser
        35                  40                  45

Ala Pro Gly Ala Leu Ala Gly Gly Pro Thr Gln Ala Ala Pro Gly Val
    50                  55                  60

Arg Gly Glu Glu Glu Gln Trp Ala Arg Glu Ile Gly Ala Gln Leu Arg
65                  70                  75                  80

Arg Met Ala Asp Asp Leu Asn Ala Gln Tyr Glu Arg Arg Arg Gln Glu
                85                  90                  95

Glu Gln Gln Arg His Arg Pro Ser Pro Trp Arg Val Leu Tyr Asn Leu
            100                 105                 110
```

-continued

```
Ile Met Gly Leu Leu Pro Leu Pro Arg Gly His Arg Ala Pro Glu Met
        115                 120                 125

Glu Pro Asn
    130

<210> SEQ ID NO 11
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205

<210> SEQ ID NO 12
<211> LENGTH: 22
<212> TYPE: PRT
<213> ORGANISM: Homo sapiens

<400> SEQUENCE: 12

Gln Asp Ala Ser Thr Lys Lys Leu Ser Glu Cys Leu Lys Arg Ile Gly
1               5                   10                  15

Asp Glu Leu Asp Ser Asn
            20

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (2)..(2)
<223> OTHER INFORMATION: Ala, Ser or Gly
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (8)..(8)
<223> OTHER INFORMATION: Ile, Met or Val
<220> FEATURE:
<221> NAME/KEY: MOD_RES
<222> LOCATION: (10)..(10)
<223> OTHER INFORMATION: Asp or Glu
<220> FEATURE:
<221> NAME/KEY: MOD_RES
<222> LOCATION: (11)..(11)
<223> OTHER INFORMATION: Leu or Phe
<220> FEATURE:
<221> NAME/KEY: MOD_RES
<222> LOCATION: (12)..(12)
<223> OTHER INFORMATION: Asn or Asp
<220> FEATURE:
<221> NAME/KEY: MOD_RES
<222> LOCATION: (13)..(13)
<223> OTHER INFORMATION: Ala or Ser
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Tyr or Met

<400> SEQUENCE: 13

Xaa Xaa Xaa Xaa Leu Xaa Arg Xaa Asp Xaa Xaa Xaa Xaa Xaa Xaa
1               5                   10                  15

<210> SEQ ID NO 14
<211> LENGTH: 22
<212> TYPE: PRT
<213> ORGANISM: Homo sapiens

<400> SEQUENCE: 14

Thr Trp Gln Thr Val Thr Ile Phe Val Ala Gly Val Leu Thr Ala Ser
1               5                   10                  15

Leu Thr Ile Trp Lys Lys
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ser Thr Lys Lys Leu Ser Glu Ser Leu Lys Arg Ile Gly Asp Glu
1               5                   10                  15

Leu Asp Ser Asn
```

```
<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Val Gly Arg Gln Leu Ala Ile Ile Gly Asp Asp Ile Asn Arg Arg
1               5                   10                  15

Tyr Asp

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Ala Glu Val Ser Ala Val Leu Leu Arg Leu Gly Asp Glu Leu
1               5                   10                  15

Glu Met Ile Arg
            20

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Val His Leu Thr Leu Arg Gln Ala Gly Asp Asp Phe Ser Arg Arg
1               5                   10                  15

Tyr

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Leu Glu Thr Leu Arg Arg Val Gly Asp Gly Val Gln Arg Asn
1               5                   10                  15

His Glu

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Glu Val Glu Lys Asn Leu Lys Ser Cys Leu Asp Asn Val Asn Val
```

Val Ser Val

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu His Gln Ala Met Arg Ala Ala Gly Asp Glu Phe Glu Thr Arg Phe
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Val Lys Gln Ala Leu Arg Glu Ala Gly Asp Glu Phe Glu Leu Arg
1               5                   10                  15

Tyr

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ala Ala Val Leu Arg Ser Ala Ala Ala Arg Leu Arg Gln Ile His
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Arg Asn Ile Ala Arg His Leu Ala Gln Val Gly Asp Ser Met Asp
1               5                   10                  15

Arg Ser

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gln Arg Tyr Gly Arg Glu Leu Arg Arg Met Ser Asp Glu Phe Val
1               5                   10                  15

Asp Ser Phe Lys

```
                             20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Trp Ile Ala Gln Glu Leu Arg Arg Ile Gly Asp Glu Phe Asn Ala
1               5                   10                  15

Tyr Tyr Ala Arg
            20

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Glu Ile Gly Ala Gln Leu Arg Arg Met Ala Asp Asp Leu Asn Ala
1               5                   10                  15

Gln Tyr

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Cys Ala Thr Gln Leu Arg Arg Phe Gly Asp Lys Leu Asn Phe Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ile Ala Arg Lys Leu Gln Cys Ile Ala Asp Gln Phe His Arg Leu
1               5                   10                  15

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Leu Ala Leu Arg Leu Ala Cys Ile Gly Asp Glu Met Asp Val Ser
1               5                   10                  15

Leu Arg Ala
```

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Lys Glu Val Glu Ser Ile Leu Lys Lys Asn Ser Asp Trp Ile
1               5                   10                  15

Trp Asp Trp Ser Ser Arg
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Leu Thr Ala Ala Arg Leu Lys Ala Leu Gly Asp Glu Leu His Gln
1               5                   10                  15

Arg Thr Met Trp
            20

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Glu Val Glu Ala Leu Lys Lys Ser Ala Asp Trp Val Ser Asp Trp
1               5                   10                  15

Ser Ser Arg

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Leu Glu Ala Glu Leu Asp Ala Leu Gly Asp Glu Leu Leu Ala
1               5                   10                  15

<210> SEQ ID NO 35
<211> LENGTH: 20
<212> TYPE: PRT
<213> ORGANISM: Unknown
<220> FEATURE:
<223> OTHER INFORMATION: Description of Unknown: BIM SAHB (wt) peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 35

Glu Ile Trp Ile Ala Gln Glu Leu Arg Xaa Ile Gly Asp Xaa Phe Asn
1               5                   10                  15

Ala Tyr Tyr Ala
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 36

Glu Ile Cys Ile Ala Gln Glu Leu Arg Xaa Ile Gly Asp Xaa Phe Asn
1               5                   10                  15

Ala Tyr Tyr Ala
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 37

Glu Ile Trp Ile Ala Gln Glu Leu Arg Xaa Ile Gly Asp Xaa Phe Asn
1               5                   10                  15

Ala Tyr Tyr Cys
            20

<210> SEQ ID NO 38
<211> LENGTH: 21
<212> TYPE: PRT
<213> ORGANISM: Mus sp.
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 38

Ile Arg Ile Ala Gln Glu Leu Arg Xaa Ile Gly Asp Xaa Phe Asn Glu
1               5                   10                  15

Thr Tyr Thr Arg Arg

-continued

<210> SEQ ID NO 39
<211> LENGTH: 21
<212> TYPE: PRT
<213> ORGANISM: Mus sp.
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 39

Ile Arg Ile Ala Gln Glu Leu Arg Xaa Ile Gly Asp Xaa Phe Asn Glu
1               5                   10                  15

Thr Tyr Thr Arg Arg
            20

<210> SEQ ID NO 40
<211> LENGTH: 20
<212> TYPE: PRT
<213> ORGANISM: Mus sp.
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 40

Glu Ile Arg Ile Ala Gln Glu Leu Arg Xaa Ile Gly Asp Xaa Phe Asn
1               5                   10                  15

Glu Thr Tyr Thr
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 41

Ile Trp Ile Ala Gln Glu Leu Arg Xaa Ile Glu Asp Xaa Phe Asn Ala
1               5                   10                  15

Tyr Tyr Ala Arg Arg
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 42

Ile Trp Ile Ala Gln Glu Ala Arg Xaa Ile Gly Ala Xaa Phe Asn Ala
1               5                   10                  15

Tyr Tyr Ala Arg Arg
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 43

Ile Trp Ile Ala Gln Glu Leu Arg Xaa Ile Ser Asp Xaa Phe Asn Ala
1               5                   10                  15

Tyr Tyr Ala Arg Arg
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 44

Ile Trp Ile Ala Gln Arg Leu Arg Xaa Ile Gly Asp Xaa Phe Asn Ala
1               5                   10                  15

Tyr Tyr Ala Arg Arg
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
```

```
<220> FEATURE:
<221> NAME/KEY: MOD_RES
<222> LOCATION: (13)..(13)
<223> OTHER INFORMATION: Any hydrocarbon stapled amino acid

<400> SEQUENCE: 45

Ile Trp Ile Ala Gln Glu Leu Asp Xaa Ile Gly Asp Xaa Phe Asn Ala
1               5                   10                  15

Tyr Tyr Ala Arg Arg
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 46

Ile Trp Ile Ala Gln Arg Leu Asp Xaa Ile Gly Asp Xaa Phe Asn Ala
1               5                   10                  15

Tyr Tyr Ala Arg Arg
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 47

Ile Arg Ile Ala Gln Glu Leu Arg Xaa Ile Gly Asp Xaa Phe Asn Ala
1               5                   10                  15

Tyr Tyr Ala Arg Arg
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid
```

```
<400> SEQUENCE: 48

Ile Trp Ile Ala Gln Glu Leu Arg Xaa Ile Gly Asp Xaa Phe Asn Glu
1               5                   10                  15

Tyr Tyr Ala Arg Arg
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 49

Ile Trp Ile Ala Gln Glu Leu Arg Xaa Ile Gly Asp Xaa Phe Asn Ala
1               5                   10                  15

Thr Tyr Ala Arg Arg
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 50

Ile Trp Ile Ala Gln Glu Leu Arg Xaa Ile Gly Asp Xaa Phe Asn Ala
1               5                   10                  15

Tyr Tyr Thr Arg Arg
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 51

Glu Ile Trp Ile Ala Gln Glu Leu Arg Xaa Ile Glu Asp Xaa Phe Asn
```

```
1               5                   10                  15

Ala Tyr Tyr Ala
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 52

Glu Ile Trp Ile Ala Gln Glu Ala Arg Xaa Ile Gly Ala Xaa Phe Asn
1               5                   10                  15

Ala Tyr Tyr Ala
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 53

Glu Ile Trp Ile Ala Gln Glu Leu Arg Xaa Ile Ser Asp Xaa Phe Asn
1               5                   10                  15

Ala Tyr Tyr Ala
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 54

Glu Ile Trp Ile Ala Gln Arg Leu Arg Xaa Ile Gly Asp Xaa Phe Asn
1               5                   10                  15

Ala Tyr Tyr Ala
            20
```

```
<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 55

Glu Ile Trp Ile Ala Gln Glu Leu Asp Xaa Ile Gly Asp Xaa Phe Asn
1               5                   10                  15

Ala Tyr Tyr Ala
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 56

Glu Ile Trp Ile Ala Gln Arg Leu Asp Xaa Ile Gly Asp Xaa Phe Asn
1               5                   10                  15

Ala Tyr Tyr Ala
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 57

Glu Ile Arg Ile Ala Gln Glu Leu Arg Xaa Ile Gly Asp Xaa Phe Asn
1               5                   10                  15

Ala Tyr Tyr Ala
            20

<210> SEQ ID NO 58
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 58

Glu Ile Trp Ile Ala Gln Glu Leu Arg Xaa Ile Gly Asp Xaa Phe Asn
1               5                   10                  15

Glu Tyr Tyr Ala
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 59

Glu Ile Trp Ile Ala Gln Glu Leu Arg Xaa Ile Gly Asp Xaa Phe Asn
1               5                   10                  15

Ala Thr Tyr Ala
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 60

Glu Ile Trp Ile Ala Gln Glu Leu Arg Xaa Ile Gly Asp Xaa Phe Asn
1               5                   10                  15

Ala Tyr Tyr Thr
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 61

Glu Ile Trp Ile Ala Gln Glu Leu Arg Xaa Glu Gly Asp Xaa Phe Asn
1               5                   10                  15

Ala Tyr Tyr Ala
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 62

Arg Ile Trp Ile Ala Gln Glu Leu Arg Xaa Ile Gly Asp Xaa Phe Asn
1               5                   10                  15

Ala Tyr Tyr Ala
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 63

Glu Ile Trp Ile Ala Gln Glu Leu Arg Xaa Ile Gly Arg Xaa Phe Asn
1               5                   10                  15

Ala Tyr Tyr Ala
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)

```
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 64

Glu Ile Trp Ile Ala Gln Glu Leu Arg Xaa Ile Gly Asp Xaa Phe Arg
1               5                   10                  15

Ala Tyr Tyr Ala
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 65

Glu Ile Trp Ile Ala Gln Glu Leu Arg Xaa Ile Gly Asp Xaa Phe Glu
1               5                   10                  15

Ala Tyr Tyr Ala
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 66

Glu Ile Trp Ile Ala Gln Glu Leu Arg Xaa Ile Gly Arg Xaa Phe Glu
1               5                   10                  15

Ala Tyr Tyr Ala
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
```

```
<223> OTHER INFORMATION: Any hydrocarbon stapled amino acid

<400> SEQUENCE: 67

Glu Ile Trp Ile Ala Gln Glu Leu Arg Xaa Ile Gly Arg Xaa Phe Arg
1               5                   10                  15

Ala Tyr Tyr Ala
            20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any hydrocarbon stapled amino acid
<220> FEATURE:
<221> NAME/KEY: MOD_RES
<222> LOCATION: (6)..(6)
<223> OTHER INFORMATION: Any hydrocarbon stapled amino acid

<400> SEQUENCE: 68

Ile Xaa Ile Ala Gln Xaa Leu Arg Arg Ile Gly Asp Glu Phe Asn Ala
1               5                   10                  15

Tyr Tyr Ala Arg Arg
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 69

Glu Ile Xaa Ile Ala Gln Xaa Leu Arg Arg Ile Gly Asp Glu Phe Asn
1               5                   10                  15

Ala Tyr Tyr Ala
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 70
```

```
Glu Ile Xaa Ile Ala Gln Xaa Leu Arg Arg Ile Gly Asp Lys Phe Asn
1               5                   10                  15

Ala Tyr Tyr Ala
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 71

Ile Trp Xaa Ala Gln Glu Xaa Arg Arg Ile Gly Asp Glu Phe Asn Ala
1               5                   10                  15

Tyr Tyr Ala Arg Arg
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any hydrocarbon stapled amino acid
<220> FEATURE:
<221> NAME/KEY: MOD_RES
<222> LOCATION: (8)..(8)
<223> OTHER INFORMATION: Any hydrocarbon stapled amino acid

<400> SEQUENCE: 72

Glu Ile Trp Xaa Ala Gln Glu Xaa Arg Arg Ile Gly Asp Glu Phe Asn
1               5                   10                  15

Ala Tyr Tyr Ala
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any hydrocarbon stapled amino acid
<220> FEATURE:
<221> NAME/KEY: MOD_RES
<222> LOCATION: (8)..(8)
<223> OTHER INFORMATION: Any hydrocarbon stapled amino acid

<400> SEQUENCE: 73

Ile Trp Ile Xaa Gln Glu Leu Xaa Arg Ile Gly Asp Glu Phe Asn Ala
1               5                   10                  15

Tyr Tyr Ala Arg Arg
```

```
                    20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any hydrocarbon stapled amino acid
<220> FEATURE:
<221> NAME/KEY: MOD_RES
<222> LOCATION: (9)..(9)
<223> OTHER INFORMATION: Any hydrocarbon stapled amino acid

<400> SEQUENCE: 74

Glu Ile Trp Ile Xaa Gln Glu Leu Xaa Arg Ile Gly Asp Glu Phe Asn
1               5                   10                  15

Ala Tyr Tyr Ala
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any hydrocarbon stapled amino acid
<220> FEATURE:
<221> NAME/KEY: MOD_RES
<222> LOCATION: (17)..(17)
<223> OTHER INFORMATION: Any hydrocarbon stapled amino acid

<400> SEQUENCE: 75

Ile Trp Ile Ala Gln Glu Leu Arg Arg Ile Gly Asp Xaa Phe Asn Ala
1               5                   10                  15

Xaa Tyr Ala Arg Arg
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (18)..(18)
<223> OTHER INFORMATION: Any hydrocarbon stapled amino acid

<400> SEQUENCE: 76

Glu Ile Trp Ile Ala Gln Glu Leu Arg Arg Ile Gly Asp Xaa Phe Asn
1               5                   10                  15

Ala Xaa Tyr Ala
            20

<210> SEQ ID NO 77
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any hydrocarbon stapled amino acid
<220> FEATURE:
<221> NAME/KEY: MOD_RES
<222> LOCATION: (9)..(9)
<223> OTHER INFORMATION: Any hydrocarbon stapled amino acid

<400> SEQUENCE: 77

Ile Trp Ile Ala Xaa Glu Leu Arg Xaa Ile Gly Asp Glu Phe Asn Ala
1               5                   10                  15

Tyr Tyr Ala Arg Arg
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any hydrocarbon stapled amino acid
<220> FEATURE:
<221> NAME/KEY: MOD_RES
<222> LOCATION: (10)..(10)
<223> OTHER INFORMATION: Any hydrocarbon stapled amino acid

<400> SEQUENCE: 78

Glu Ile Trp Ile Ala Xaa Glu Leu Arg Xaa Ile Gly Asp Glu Phe Asn
1               5                   10                  15

Ala Tyr Tyr Ala
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any hydrocarbon stapled amino acid
<220> FEATURE:
<221> NAME/KEY: MOD_RES
<222> LOCATION: (19)..(19)
<223> OTHER INFORMATION: Any hydrocarbon stapled amino acid

<400> SEQUENCE: 79

Ile Trp Ile Ala Gln Glu Leu Arg Arg Ile Gly Asp Glu Phe Xaa Ala
1               5                   10                  15

Tyr Tyr Xaa Arg Arg
            20

<210> SEQ ID NO 80
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any hydrocarbon stapled amino acid
<220> FEATURE:
<221> NAME/KEY: MOD_RES
<222> LOCATION: (20)..(20)
<223> OTHER INFORMATION: Any hydrocarbon stapled amino acid

<400> SEQUENCE: 80

Glu Ile Trp Ile Ala Gln Glu Leu Arg Arg Ile Gly Asp Glu Phe Xaa
1               5                   10                  15

Ala Tyr Tyr Xaa
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cys or Lys
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 81

Glu Ile Xaa Ile Ala Gln Glu Leu Arg Xaa Ile Gly Asp Xaa Phe Asn
1               5                   10                  15

Ala Tyr Tyr Ala
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Cys or Lys
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 82

Glu Ile Trp Ile Xaa Gln Glu Leu Arg Xaa Ile Gly Asp Xaa Phe Asn
1               5                   10                  15

Ala Tyr Tyr Ala
            20

<210> SEQ ID NO 83
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (12)..(12)
<223> OTHER INFORMATION: Cys or Lys
<220> FEATURE:
<221> NAME/KEY: MOD_RES
<222> LOCATION: (14)..(14)
<223> OTHER INFORMATION: Any hydrocarbon stapled amino acid

<400> SEQUENCE: 83

Glu Ile Trp Ile Ala Gln Glu Leu Arg Xaa Ile Xaa Asp Xaa Phe Asn
1               5                   10                  15

Ala Tyr Tyr Ala
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (18)..(18)
<223> OTHER INFORMATION: Cys or Lys

<400> SEQUENCE: 84

Glu Ile Trp Ile Ala Gln Glu Leu Arg Xaa Ile Gly Asp Xaa Phe Asn
1               5                   10                  15

Ala Xaa Tyr Ala
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (19)..(19)
<223> OTHER INFORMATION: Cys or Lys

<400> SEQUENCE: 85
```

-continued

```
Glu Ile Trp Ile Ala Gln Glu Leu Arg Xaa Ile Gly Asp Xaa Phe Asn
1               5                   10                  15

Ala Tyr Xaa Ala
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (20)..(20)
<223> OTHER INFORMATION: Cys or Lys

<400> SEQUENCE: 86

Glu Ile Trp Ile Ala Gln Glu Leu Arg Xaa Ile Gly Asp Xaa Phe Asn
1               5                   10                  15

Ala Tyr Tyr Xaa
            20

<210> SEQ ID NO 87
<211> LENGTH: 25
<212> TYPE: PRT
<213> ORGANISM: Mus sp.

<400> SEQUENCE: 87

Glu Ser Gln Glu Glu Ile Ile His Asn Ile Ala Arg His Leu Ala Gln
1               5                   10                  15

Ile Gly Asp Glu Asx Asp His Asn Ile
            20                  25

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 88

Asp Ile Ile Arg Asn Ile Ala Arg His Leu Ala Xaa Val Gly Asp Xaa
1               5                   10                  15

Asx Asp Arg Ser Ile
            20

<210> SEQ ID NO 89
<211> LENGTH: 21
<212> TYPE: PRT
<213> ORGANISM: Mus sp.
```

-continued

```
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 89

Glu Ile Ile His Asn Ile Ala Arg His Leu Ala Xaa Ile Gly Asp Xaa
1               5                   10                  15

Asx Asp His Asn Ile
            20

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any hydrocarbon stapled amino acid
<220> FEATURE:
<221> NAME/KEY: MOD_RES
<222> LOCATION: (20)..(20)
<223> OTHER INFORMATION: Any hydrocarbon stapled amino acid

<400> SEQUENCE: 90

Glu Ser Gln Glu Asp Ile Ile Arg Asn Ile Ala Arg His Leu Ala Xaa
1               5                   10                  15

Val Gly Asp Xaa Asx Asp Arg Ser Ile
            20                  25

<210> SEQ ID NO 91
<211> LENGTH: 25
<212> TYPE: PRT
<213> ORGANISM: Mus sp.
<220> FEATURE:
<221> NAME/KEY: MOD_RES
<222> LOCATION: (16)..(16)
<223> OTHER INFORMATION: Any hydrocarbon stapled amino acid
<220> FEATURE:
<221> NAME/KEY: MOD_RES
<222> LOCATION: (20)..(20)
<223> OTHER INFORMATION: Any hydrocarbon stapled amino acid

<400> SEQUENCE: 91

Glu Ser Gln Glu Glu Ile Ile His Asn Ile Ala Arg His Leu Ala Xaa
1               5                   10                  15

Ile Gly Asp Xaa Asx Asp His Asn Ile
            20                  25

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
```

<223> OTHER INFORMATION: Any hydrocarbon stapled amino acid

<400> SEQUENCE: 92

Asp Ile Ile Arg Asn Ile Ala Arg His Leu Ala Xaa Val Glu Asp Xaa
1               5                   10                  15

Asx Asp Arg Ser Ile
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 93

Asp Ile Ile Arg Asn Ile Ala Arg His Leu Ala Xaa Val Ser Asp Xaa
1               5                   10                  15

Asx Asp Arg Ser Ile
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 94

Asp Ile Ile Arg Asn Ile Ala Arg His Ala Ala Xaa Val Gly Ala Xaa
1               5                   10                  15

Asx Asp Arg Ser Ile
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 95

-continued

```
Asp Ile Ile Arg Asn Ile Ala Arg His Leu Ala Xaa Val Gly Asp Xaa
1               5                   10                  15

Ala Ala Arg Ser Ile
            20
```

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 96

```
Asp Ile Ile Arg Asn Ile Ala Arg His Leu Ala Xaa Val Ala Asp Xaa
1               5                   10                  15

Asx Asp Arg Ser Ile
            20
```

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 97

```
Gln Trp Ala Arg Glu Ile Gly Leu Gln Ala Arg Xaa Asx Ala Asp Xaa
1               5                   10                  15

Leu Asn Ala Gln Tyr
            20
```

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 98

```
Gln Trp Ala Arg Glu Ile Gly Ala Gln Ala Arg Xaa Asx Ala Ala Xaa
1               5                   10                  15

Leu Asn Ala Gln Tyr
```

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 99

Gln Trp Ala Arg Glu Ile Gly Leu Gln Ala Arg Xaa Asx Glu Asp Xaa
1               5                   10                  15

Leu Asn Ala Gln Tyr
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 100

Gln Trp Ala Arg Glu Ile Gly Leu Gln Ala Asp Xaa Asx Ala Asp Xaa
1               5                   10                  15

Leu Asn Ala Gln Tyr
            20

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any hydrocarbon stapled amino acid
<220> FEATURE:
<221> NAME/KEY: MOD_RES
<222> LOCATION: (17)..(17)
<223> OTHER INFORMATION: Any hydrocarbon stapled amino acid

<400> SEQUENCE: 101

Glu Gln Trp Ala Arg Glu Ile Gly Leu Gln Ala Arg Xaa Asx Ala Asp
1               5                   10                  15

Xaa Leu Asn Ala Gln Tyr
            20

<210> SEQ ID NO 102

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any hydrocarbon stapled amino acid
<220> FEATURE:
<221> NAME/KEY: MOD_RES
<222> LOCATION: (17)..(17)
<223> OTHER INFORMATION: Any hydrocarbon stapled amino acid

<400> SEQUENCE: 102

Glu Gln Trp Ala Arg Glu Ile Gly Leu Gln Ala Arg Xaa Asx Ala Asp
1               5                   10                  15

Xaa Leu Asn Ala Gln Tyr Glu
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 103

Gln Trp Xaa Arg Glu Ile Xaa Leu Gln Ala Arg Arg Asx Ala Asp Asp
1               5                   10                  15

Leu Asn Ala Gln Tyr
            20

<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any hydrocarbon stapled amino acid
<220> FEATURE:
<221> NAME/KEY: MOD_RES
<222> LOCATION: (8)..(8)
<223> OTHER INFORMATION: Any hydrocarbon stapled amino acid

<400> SEQUENCE: 104

Glu Gln Trp Xaa Arg Glu Ile Xaa Leu Gln Ala Arg Arg Asx Ala Asp
1               5                   10                  15

Asp Leu Asn Ala Gln Tyr Glu
            20

<210> SEQ ID NO 105
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 105

Gln Trp Xaa Arg Glu Ile Xaa Leu Gln Ala Asp Arg Asx Ala Asp
1               5                   10                  15

Leu Asn Ala Gln Tyr
            20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any hydrocarbon stapled amino acid
<220> FEATURE:
<221> NAME/KEY: MOD_RES
<222> LOCATION: (8)..(8)
<223> OTHER INFORMATION: Any hydrocarbon stapled amino acid

<400> SEQUENCE: 106

Glu Gln Trp Xaa Arg Glu Ile Xaa Leu Gln Ala Asp Arg Asx Ala Asp
1               5                   10                  15

Asp Leu Asn Ala Gln Tyr Glu
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any hydrocarbon stapled amino acid
<220> FEATURE:
<221> NAME/KEY: MOD_RES
<222> LOCATION: (7)..(7)
<223> OTHER INFORMATION: Any hydrocarbon stapled amino acid

<400> SEQUENCE: 107

Gln Trp Xaa Arg Glu Ile Xaa Leu Gln Ala Arg Arg Asx Ala Arg Asp
1               5                   10                  15

Leu Asn Ala Gln Tyr
            20

<210> SEQ ID NO 108
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (4)..(4)
<223> OTHER INFORMATION: Any hydrocarbon stapled amino acid
<220> FEATURE:
<221> NAME/KEY: MOD_RES
<222> LOCATION: (8)..(8)
<223> OTHER INFORMATION: Any hydrocarbon stapled amino acid

<400> SEQUENCE: 108

Glu Gln Trp Xaa Arg Glu Ile Xaa Leu Gln Ala Arg Arg Asx Ala Arg
1               5                   10                  15

Asp Leu Asn Ala Gln Tyr Glu
            20

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 109

Ile Ala Gln Glu Leu Arg Xaa Ile Gly Asp Xaa Phe Asn Ala Tyr Tyr
1               5                   10                  15

Ala Arg Arg

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 110

Ile Trp Ile Ala Gln Glu Leu Arg Xaa Ile Gly Asp Xaa
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asn Ala Tyr Tyr Ala Arg Arg
1               5

<210> SEQ ID NO 112
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 112

Ile Trp Ile Ala Gln Glu Leu Arg Xaa Ile Gly Asp Xaa Phe Asn Ala
1               5                   10                  15

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Ala Arg Arg
1

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 114

Ile Trp Ile Ala Gln Glu Leu Arg Xaa Ile Gly Asp Xaa Phe Asn Ala
1               5                   10                  15

Tyr

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 115

Ile Arg Ile Ala Gln Glu Leu Arg Xaa Ile Gly Asp Xaa Phe Asn Ala
1               5                   10                  15

Tyr
```

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 116

Ile Trp Ile Ala Gln Glu Leu Arg Xaa Ile Gly Asp Xaa Phe Asn Glu
1               5                   10                  15

Tyr

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 117

Ile Trp Ile Ala Gln Glu Leu Arg Xaa Ile Gly Asp Xaa Phe Asn Ala
1               5                   10                  15

Thr

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 118

Ile Trp Ile Ala Gln Glu Leu Arg Xaa Ile Gly Asp Xaa Phe Asn Ala
1               5                   10                  15

Tyr

<210> SEQ ID NO 119
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 119

Ile Trp Ile Ala Gln Glu Leu Asp Xaa Ile Gly Asp Xaa Phe Asn Ala
1               5                   10                  15

Tyr

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 120

Ile Trp Ile Ala Gln Arg Leu Arg Xaa Ile Gly Asp Xaa Phe Asn Ala
1               5                   10                  15

Tyr

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 121

Ile Trp Ile Ala Gln Arg Leu Asp Xaa Ile Gly Asp Xaa Phe Asn Ala
1               5                   10                  15

Tyr

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
```

```
<221> NAME/KEY: MOD_RES
<222> LOCATION: (11)..(11)
<223> OTHER INFORMATION: Any hydrocarbon stapled amino acid

<400> SEQUENCE: 122

Ile Ala Gln Glu Leu Arg Xaa Ile Gly Asp Xaa Phe Asn Ala Tyr Tyr
1               5                   10                  15

Ala

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 123

Glu Ile Trp Ile Ala Gln Glu Leu Arg Xaa Ile Gly Asp Xaa
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asn Ala Tyr Tyr Ala
1               5

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 125

Glu Ile Trp Ile Ala Gln Glu Leu Arg Xaa Ile Gly Asp Xaa Phe Asn
1               5                   10                  15

Ala

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 126

Glu Ile Trp Ile Ala Gln Glu Leu Arg Xaa Ile Gly Asp Xaa Phe Asn
1               5                   10                  15

Ala Tyr

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 127

Glu Ile Arg Ile Ala Gln Glu Leu Arg Xaa Ile Gly Asp Xaa Phe Asn
1               5                   10                  15

Ala Tyr

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 128

Glu Ile Trp Ile Ala Gln Glu Leu Arg Xaa Ile Gly Asp Xaa Phe Asn
1               5                   10                  15

Glu Tyr

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
```

```
<223> OTHER INFORMATION: Any hydrocarbon stapled amino acid

<400> SEQUENCE: 129

Glu Ile Trp Ile Ala Gln Glu Leu Arg Xaa Ile Gly Asp Xaa Phe Asn
1               5                   10                  15

Ala Thr

<210> SEQ ID NO 130
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 130

Glu Ile Trp Ile Ala Gln Glu Leu Arg Xaa Ile Gly Asp Xaa Phe Asn
1               5                   10                  15

Ala Tyr

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 131

Glu Ile Trp Ile Ala Gln Glu Leu Asp Xaa Ile Gly Asp Xaa Phe Asn
1               5                   10                  15

Ala Tyr

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 132

Glu Ile Trp Ile Ala Gln Arg Leu Arg Xaa Ile Gly Asp Xaa Phe Asn
1               5                   10                  15
```

Ala Tyr

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 133

Glu Ile Trp Ile Ala Gln Arg Leu Asp Xaa Ile Gly Asp Xaa Phe Asn
1               5                   10                  15
Ala Tyr

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 134

Asp Ile Ile Arg Asn Ile Ala Arg His Leu Ala Xaa Val Gly Asp Xaa
1               5                   10                  15
Asx Asp Arg Ser Ile
            20

<210> SEQ ID NO 135
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ile Ile Arg
1

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES

```
<222> LOCATION: (11)..(11)
<223> OTHER INFORMATION: Any hydrocarbon stapled amino acid

<400> SEQUENCE: 136

Ile Ala Arg His Leu Ala Xaa Val Gly Asp Xaa Asx Asp Arg Ser Ile
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 137

Asp Ile Ile Arg Asn Ile Ala Arg His Leu Ala Xaa Val Gly Asp Xaa
1               5                   10                  15

<210> SEQ ID NO 138
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Arg Ser Ile
1

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 139

Asp Ile Ile Arg Asn Ile Ala Arg His Leu Ala Xaa Val Gly Asp Xaa
1               5                   10                  15

Asx Asp Arg

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
```

```
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 140

Asp Ile Ile Arg Asn Ile Ala Arg His Leu Ala Xaa Val Gly Asp Xaa
1               5                   10                  15

Asx Asp Arg Ser
            20

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 141

Gln Trp Ala Arg Glu Ile Gly Leu Gln Ala Arg Xaa Asx Ala Asp Xaa
1               5                   10                  15

Leu Asn Ala Gln Tyr
            20

<210> SEQ ID NO 142
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any hydrocarbon stapled amino acid
<220> FEATURE:
<221> NAME/KEY: MOD_RES
<222> LOCATION: (14)..(14)
<223> OTHER INFORMATION: Any hydrocarbon stapled amino acid

<400> SEQUENCE: 142

Ala Arg Glu Ile Gly Leu Gln Ala Arg Xaa Asx Ala Asp Xaa Leu Asn
1               5                   10                  15

Ala Gln Tyr

<210> SEQ ID NO 143
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Trp Ala Arg
1

<210> SEQ ID NO 144
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 144

Ile Gly Leu Gln Ala Arg Xaa Asx Ala Asp Xaa Leu Asn Ala Gln Tyr
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 145

Gln Trp Ala Arg Glu Ile Gly Leu Gln Ala Arg Xaa Asx Ala Asp Xaa
1               5                   10                  15

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Ala Gln Tyr
1

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 147

Gln Trp Ala Arg Glu Ile Gly Leu Gln Ala Arg Xaa Asx Ala Asp Xaa
1               5                   10                  15

Leu Asn Ala
```

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any hydrocarbon stapled amino acid
<220> FEATURE:
<221> NAME/KEY: MOD_RES
<222> LOCATION: (16)..(16)
<223> OTHER INFORMATION: Any hydrocarbon stapled amino acid

<400> SEQUENCE: 148

Gln Trp Ala Arg Glu Ile Gly Leu Gln Ala Arg Xaa Asx Ala Asp Xaa
1               5                   10                  15

Leu Asn Ala Gln
            20

<210> SEQ ID NO 149
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (18)..(18)
<223> OTHER INFORMATION: Any hydrocarbon stapled amino acid

<400> SEQUENCE: 149

Asn Leu Trp Ala Ala Gln Arg Tyr Gly Arg Glu Leu Arg Xaa Asx Ser
1               5                   10                  15

Asp Xaa Phe Val Asp Ser Phe Lys Lys
            20                  25

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any hydrocarbon stapled amino acid
<220> FEATURE:
<221> NAME/KEY: MOD_RES
<222> LOCATION: (18)..(18)
<223> OTHER INFORMATION: Any hydrocarbon stapled amino acid

<400> SEQUENCE: 150

Gln Asp Ala Ser Thr Lys Lys Leu Ser Glu Cys Leu Lys Xaa Ile Gly
1               5                   10                  15

Asp Xaa Leu Asp Ser Asn
            20

<210> SEQ ID NO 151
<211> LENGTH: 22

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 151

Gln Asp Ala Ser Thr Lys Xaa Leu Ser Glu Xaa Leu Lys Arg Ile Gly
1               5                   10                  15

Asp Glu Leu Asp Ser Asn
            20

<210> SEQ ID NO 152
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 152

Gln Asp Ala Ser Thr Lys Xaa Leu Ser Glu Xaa Leu Asp Arg Ile Gly
1               5                   10                  15

Asp Glu Leu Asp Ser Asn
            20

<210> SEQ ID NO 153
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 153

Gln Asp Ala Ser Thr Lys Xaa Leu Ser Glu Xaa Leu Lys Arg Ile Gly
1               5                   10                  15

Arg Glu Leu Asp Ser Asn
            20

<210> SEQ ID NO 154
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
peptide
<220> FEATURE:
<221> NAME/KEY: MOD_RES
<222> LOCATION: (8)..(8)
<223> OTHER INFORMATION: Any hydrocarbon stapled amino acid
<220> FEATURE:
<221> NAME/KEY: MOD_RES
<222> LOCATION: (12)..(12)
<223> OTHER INFORMATION: Any hydrocarbon stapled amino acid

<400> SEQUENCE: 154

Gln Asp Ala Ser Thr Lys Lys Xaa Ser Glu Cys Xaa Lys Arg Ile Gly
1               5                   10                  15

Asp Glu Leu Asp Ser Asn
            20

<210> SEQ ID NO 155
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any hydrocarbon stapled amino acid
<220> FEATURE:
<221> NAME/KEY: MOD_RES
<222> LOCATION: (13)..(13)
<223> OTHER INFORMATION: Any hydrocarbon stapled amino acid

<400> SEQUENCE: 155

Gln Asp Ala Ser Thr Lys Lys Leu Xaa Glu Cys Leu Xaa Arg Ile Gly
1               5                   10                  15

Asp Glu Leu Asp Ser Asn
            20

<210> SEQ ID NO 156
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any hydrocarbon stapled amino acid
<220> FEATURE:
<221> NAME/KEY: MOD_RES
<222> LOCATION: (15)..(15)
<223> OTHER INFORMATION: Any hydrocarbon stapled amino acid

<400> SEQUENCE: 156

Thr Trp Gln Thr Val Thr Ile Phe Val Ala Xaa Val Leu Thr Xaa Ser
1               5                   10                  15

Leu Thr Ile Trp Lys Lys
            20

<210> SEQ ID NO 157
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
```

```
<223> OTHER INFORMATION: Any hydrocarbon stapled amino acid
<220> FEATURE:
<221> NAME/KEY: MOD_RES
<222> LOCATION: (15)..(15)
<223> OTHER INFORMATION: Any hydrocarbon stapled amino acid

<400> SEQUENCE: 157

Thr Trp Gln Thr Val Thr Asp Phe Val Ala Xaa Val Leu Thr Xaa Ser
1               5                   10                  15

Leu Thr Ile Trp Lys Lys
            20

<210> SEQ ID NO 158
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any hydrocarbon stapled amino acid
<220> FEATURE:
<221> NAME/KEY: MOD_RES
<222> LOCATION: (15)..(15)
<223> OTHER INFORMATION: Any hydrocarbon stapled amino acid

<400> SEQUENCE: 158

Thr Trp Glu Thr Val Thr Asp Phe Val Ala Xaa Cys Leu Thr Xaa Ser
1               5                   10                  15

Leu Thr Ile Trp Lys Lys
            20

<210> SEQ ID NO 159
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any hydrocarbon stapled amino acid
<220> FEATURE:
<221> NAME/KEY: MOD_RES
<222> LOCATION: (15)..(15)
<223> OTHER INFORMATION: Any hydrocarbon stapled amino acid

<400> SEQUENCE: 159

Thr Trp Glu Thr Val Thr Asp Phe Val Ala Xaa Val Leu Thr Xaa Ser
1               5                   10                  15

Leu Arg Ile Trp Lys Lys
            20

<210> SEQ ID NO 160
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
```

<223> OTHER INFORMATION: Any hydrocarbon stapled amino acid

<400> SEQUENCE: 160

Thr Trp Gln Thr Val Thr Xaa Phe Val Ala Xaa Val Leu Thr Ala Ser
1               5                   10                  15

Leu Thr Ile Trp Lys Lys
            20

<210> SEQ ID NO 161
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 161

Thr Trp Gln Thr Val Thr Xaa Phe Val Ala Xaa Val Leu Thr Asp Ser
1               5                   10                  15

Leu Thr Ile Trp Lys Lys
            20

<210> SEQ ID NO 162
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 162

Thr Trp Glu Thr Val Thr Xaa Phe Val Ala Xaa Val Leu Thr Asp Ser
1               5                   10                  15

Leu Thr Ile Trp
            20

<210> SEQ ID NO 163
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any hydrocarbon stapled amino acid
<220> FEATURE:
<221> NAME/KEY: MOD_RES
<222> LOCATION: (11)..(11)
<223> OTHER INFORMATION: Any hydrocarbon stapled amino acid

<400> SEQUENCE: 163

-continued

```
Thr Trp Glu Thr Val Thr Xaa Phe Val Ala Xaa Val Leu Thr Asp Ser
1               5                   10                  15

Leu Arg Ile Trp Lys Lys
            20

<210> SEQ ID NO 164
<211> LENGTH: 27
<212> TYPE: PRT
<213> ORGANISM: Homo sapiens

<400> SEQUENCE: 164

Gln Asp Ala Ser Thr Lys Lys Leu Ser Glu Cys Leu Lys Arg Ile Gly
1               5                   10                  15

Asp Glu Leu Asp Ser Asn Met Glu Leu Gln Arg
            20                  25
```